(12) United States Patent
Koerber et al.

(10) Patent No.: US 8,722,673 B2
(45) Date of Patent: May 13, 2014

(54) IMINE COMPOUNDS FOR COMBATING INVERTEBRATE PESTS

(75) Inventors: Karsten Koerber, Eppelheim (DE); Florian Kaiser, Mannheim (DE); Matthias Pohlman, Freinsheim (DE); Steffen Gross, Ludwigshafen (DE); Prashant Deshmukh, Mannheim (DE); Joachim Dickhaut, Heidelberg (DE); Nina Gertrud Bandur, Mannheim (DE); Wolfgang von Deyn, Neustadt (DE); Deborah L. Culberston, Fuquay Varina, NC (US); Cecille Ebuenga, Los Banos (PH); Douglas D. Anspaugh, Apex, NC (US); Franz-Josef Braun, Durham, NC (US)

(73) Assignee: BASF SE, Ludwigshafen (DE)

( * ) Notice: Subject to any disclaimer, the term of this patent is extended or adjusted under 35 U.S.C. 154(b) by 207 days.

(21) Appl. No.: 13/140,989

(22) PCT Filed: Dec. 22, 2009

(86) PCT No.: PCT/EP2009/067777
§ 371 (c)(1),
(2), (4) Date: Jun. 20, 2011

(87) PCT Pub. No.: WO2010/072781
PCT Pub. Date: Jul. 1, 2010

(65) Prior Publication Data
US 2011/0263603 A1    Oct. 27, 2011

Related U.S. Application Data

(60) Provisional application No. 61/140,378, filed on Dec. 23, 2008.

(51) Int. Cl.
*A61K 31/535*    (2006.01)
*C07D 261/02*    (2006.01)

(52) U.S. Cl.
USPC ..................................... 514/236.8; 548/240

(58) Field of Classification Search
USPC ..................................... 514/236.8; 548/240
See application file for complete search history.

(56) References Cited

U.S. PATENT DOCUMENTS

| | | | |
|---|---|---|---|
| 3,917,698 | A | 11/1975 | Breslow |
| 6,313,344 | B1 | 11/2001 | Trah et al. |
| 6,521,643 | B1 | 2/2003 | Tomishima et al. |
| 2003/0119806 | A1 | 6/2003 | Lindell et al. |
| 2004/0014801 | A1 | 1/2004 | Cohen et al. |
| 2004/0110637 | A1 | 6/2004 | Ziemer et al. |
| 2007/0066617 | A1 | 3/2007 | Mita et al. |
| 2008/0262057 | A1 | 10/2008 | Tisdell et al. |
| 2009/0023923 | A1 | 1/2009 | Mizukoshi et al. |
| 2009/0156643 | A1 | 6/2009 | Mita et al. |
| 2010/0144797 | A1 | 6/2010 | Mita et al. |
| 2010/0144808 | A1 | 6/2010 | Mita et al. |
| 2010/0160683 | A1 | 6/2010 | Matoba et al. |
| 2010/0286175 | A1 | 11/2010 | Grammenos et al. |
| 2011/0172414 | A1 | 7/2011 | Mita et al. |

FOREIGN PATENT DOCUMENTS

| | | |
|---|---|---|
| CA | 2 547 744 | 12/2006 |
| CH | 577487 | 7/1976 |
| CH | 595365 | 2/1978 |
| CH | 608011 | 12/1978 |
| CN | 1 927 860 | 3/2007 |
| DE | 10 2004 010 086 | 9/2004 |
| EP | 0 539 676 | 5/1993 |
| EP | 1 538 138 | 6/2005 |
| EP | 1 731 512 | 12/2006 |
| EP | 1 932 836 | 6/2008 |
| EP | 1 997 813 | 12/2008 |
| EP | 2 151 437 | 2/2010 |
| EP | 2 186 804 | 5/2010 |
| EP | 2199287 | 6/2010 |
| JP | 2007-016017 | 1/2007 |
| JP | 2007-106756 | 4/2007 |
| JP | 2008-239611 | 10/2008 |
| JP | 2009 108046 | 5/2009 |
| WO | WO 01/17964 | 3/2001 |
| WO | WO 02/068392 | 9/2002 |
| WO | WO 03/022808 | 3/2003 |
| WO | WO 03/062222 | 7/2003 |
| WO | WO 03/067987 | 8/2003 |
| WO | WO 2004/018410 | 3/2004 |
| WO | WO 2004/060371 | 7/2004 |
| WO | WO 2004/060865 | 7/2004 |
| WO | WO 2005/036961 | 4/2005 |
| WO | WO 2005/085216 | 9/2005 |
| WO | WO 2006/010570 | 2/2006 |
| WO | WO 2006/021833 | 3/2006 |
| WO | WO 2006/065659 | 6/2006 |

(Continued)

OTHER PUBLICATIONS

International Search Report prepared in International Application No. PCT/EP2009/067777, filed Dec. 22, 2009.
International Preliminary Report on Patentability from corresponding International Application No. PCT/EP2009/067777, filed Dec. 22, 2009.
Belen'Kii et al, Database: Beilstein, XP002580907 database accession No. 1988095, Russian Chem. Bull., (1997), pp. 101-104, vol. 46, No. 1.
Wierenga, J. et al., "Insecticidal activity of N-arylalkyl-benzhydrolpiperidines", Pest Management Science, (2002), pp. 1266-1272, vol. 58.

(Continued)

*Primary Examiner* — Marcos Sznaidman
(74) *Attorney, Agent, or Firm* — Brinks Gilson & Lione

(57) ABSTRACT

The present invention relates to imine compounds which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

32 Claims, No Drawings

(56) References Cited

FOREIGN PATENT DOCUMENTS

| | | |
|---|---|---|
| WO | WO 2007/026965 | 3/2007 |
| WO | WO 2007/070606 | 6/2007 |
| WO | WO 2007/074789 | 7/2007 |
| WO | WO 2007/075459 | 7/2007 |
| WO | WO2007/075459 * | 7/2007 |
| WO | WO 2007/079162 | 7/2007 |
| WO | WO 2007/081019 | 7/2007 |
| WO | WO 2007/093599 | 8/2007 |
| WO | WO 2007/094313 | 8/2007 |
| WO | WO 2007/105814 | 9/2007 |
| WO | WO 2007/125984 | 11/2007 |
| WO | WO 2008/012027 | 1/2008 |
| WO | WO 2008/019760 | 2/2008 |
| WO | WO 2008/022937 | 2/2008 |
| WO | WO 2008/070831 | 6/2008 |
| WO | WO 2008/108448 | 9/2008 |
| WO | WO 2008/122375 | 10/2008 |
| WO | WO 2008/126665 | 10/2008 |
| WO | WO 2008/130651 | 10/2008 |
| WO | WO 2008/154528 | 12/2008 |
| WO | WO 2009/002809 | 12/2008 |
| WO | WO 2009/005015 | 1/2009 |
| WO | WO 2009/022746 | 2/2009 |
| WO | WO 2009/025983 | 2/2009 |
| WO | WO 2009/035004 | 3/2009 |
| WO | WO 2009/045999 | 4/2009 |
| WO | WO 2009/049846 | 4/2009 |
| WO | WO 2009/077197 | 6/2009 |
| WO | WO 2009/112275 | 9/2009 |
| WO | WO 2009/126668 | 10/2009 |
| WO | WO 2010/003877 | 1/2010 |
| WO | WO 2010/003923 | 1/2010 |
| WO | WO 2010/020521 | 2/2010 |
| WO | WO 2010/020522 | 2/2010 |
| WO | WO 2010/072602 | 4/2010 |
| WO | WO 2010/112545 | 10/2010 |
| WO | WO 2011/073444 | 4/2011 |

OTHER PUBLICATIONS

Walters, Matthew J. et al., "The preparation of 5-Aryl-5-methyl-4,5-dihydroisoxazoles from dilithiated C($\alpha$), O-oximes and Select Acetyl Ketones", Synthetic Communications, 2003, p. 4163-4171, vol. 33, No. 23.
Office Action dated Dec. 5, 2012, from U.S. Appl. No. 13/003,037.
Office Action dated Oct. 24, 2012, from U.S. Appl. No. 13/003,032.
Office Action dated Jan. 29, 2013, from U.S. Appl. No. 13/141,264.
"DMP 754 Roxifiban Acetate", Drugs of the Future, (1998), pp. 707-711, vol. 23(7).
Hosking, M., et al., "Roxifiban DuPont", Current Opinion in Cardiovascular, Pulmonary & Renal Investigational Drugs, (2000), pp. 165-171, vol. 2(2).
Kaugars, G. et al., "Miticidal activity of benzoyl chloride phenylhydrazones", Journal of Agriculture and Food Chem., (1973), pp. 647-650, vol. 21, No. 4.
Kiriyama, K. et al., "Insecticidal and Neuroblocking Activities of Acetamiprid and Related Compounds", Journal of Pesticide Science, (2003), pp. 8-17, vol. 28.

* cited by examiner

IMINE COMPOUNDS FOR COMBATING INVERTEBRATE PESTS

This application is a National Stage application of International Application No. PCT/EP2009/067777, filed Dec. 22, 2009, which claims the benefit of U.S. Provisional Application No. 61/140,378, filed Dec. 23, 2008, the entire contents of which are hereby incorporated herein by reference.

The present invention relates to imine compounds which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating invertebrate pests, in particular insects, arachnids and nematodes.

WO 2005/085216 describes compounds of the formula

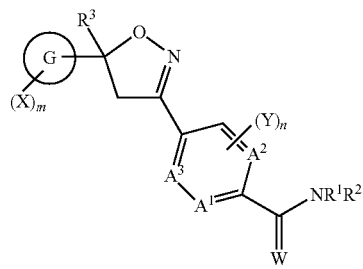

wherein, inter alia, $A^1$, $A^2$ and $A^3$ are independently carbon or nitrogen atoms, G is a benzene ring and W is O or S.

Related insecticidal aryl isoxazolines are further described in JP 2007-016017, WO 2007/026965, JP 2007-106756, WO 2007/070606, WO 2007/075459, WO 2007/079162, WO 2007/105814, WO 2007/125984, WO 2008/012027, WO 2008/019760, WO 2008/108448, JP 2008-239611, WO 2008/122375, WO 2008/130651. None of these documents discloses isoxazolines incorporating a substituted aryl imine group according to the present invention.

Substituted imines, oximes and hydrazones used as insecticides are for example described in WO 2008/122375, WO 2008/070831, WO 2008/022937, WO 2008/019760, WO 2007/105814, WO 2007/093599, WO 2007/081019, US 2007/066617, JP 2007-016017, CA 2,547,744, WO 2006/065659, WO 2006/021833, WO 2006/010570, WO 2005/085216, WO 2005/036961, DE 102004010086, WO 2004/060865, WO 2004/060371, US 2004/014801, WO 2003/067987, WO 2003/062222, WO 2003/022808, Pest Management Science (2002), 58 (12), 1266-1272, WO 02/068392, U.S. Pat. No. 6,313,344, WO 01/017964, WO 00/078739, WO 00/031034, WO 99/55668, WO 99/37603, WO 98/55448, WO 98/54125, WO 97/47592, WO 96/36228, WO 96/33168, U.S. Pat. No. 5,569,664, WO 96/22283, JP 08-092224, CH 608011, CH 595365, CH 577487 and DE 2329295. However, these documents do not describe compounds having the characteristic substituents' arrangement as claimed in the present invention.

Therefore it is an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by imine compounds of the formula I below, by their steroisomers and by their salts, in particular their agriculturally or veterinarily acceptable salts.

Therefore, in a first aspect, the invention relates to imine compounds of formula I

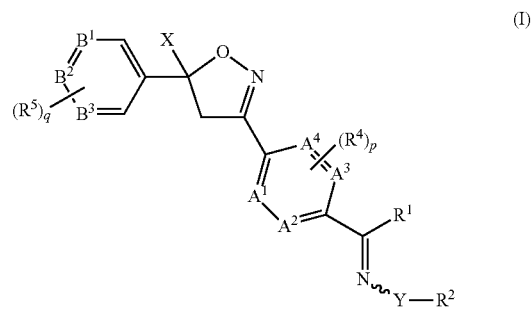

wherein $A^1$, $A^2$, $A^3$ and $A^4$ are N or CH, with the proviso that at most three of $A^1$, $A^2$, $A^3$ and $A^4$ are N;

$B^1$, $B^2$ and $B^3$ are N or CH, with the proviso that at most two of $B^1$, $B^2$ and $B^3$ are N;

X is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl and $C_3$-$C_6$-halocycloalkyl;

Y is O, N—$R^3$, S(O)$_n$ or a chemical bond;

$R^1$ is selected from the group consisting of hydrogen; cyano; $C_1$-$C_{10}$-alkyl which may be partially or fully halogenated and/or may be substituted by one or more, e.g. 1, 2, 3 or 4, radicals $R^6$; $C_1$-$C_{10}$-alkoxy; $C_1$-$C_{10}$-haloalkoxy; $C_1$-$C_{10}$-alkylthio; $C_1$-$C_{10}$-haloalkylthio; $C_1$-$C_{10}$-alkylsulfinyl; $C_1$-$C_{10}$-haloalkylsulfinyl; $C_1$-$C_{10}$-alkylsulfonyl; $C_1$-$C_{10}$-haloalkylsulfonyl; $C_3$-$C_8$-cycloalkyl which may be partially or fully halogenated and/or may be substituted by one or more, e.g. 1, 2, 3 or 4, radicals $R^6$; $C_2$-$C_{10}$-alkenyl which may be partially or fully halogenated and/or may be substituted by one or more, e.g. 1, 2, 3 or 4, radicals $R^6$; $C_2$-$C_{10}$-alkynyl which may be partially or fully halogenated and/or may be substituted by one or more, e.g. 1, 2, 3 or 4, radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; phenyl which may be substituted by 1, 2, 3, 4 or 5 radicals $R^{10}$; and a C-bound 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, radicals $R^{10}$;

$R^2$ is selected from the group consisting of hydrogen; cyano; $C_1$-$C_{10}$-alkyl which may be partially or fully halogenated and/or may be substituted by one or more, e.g. 1, 2, 3 or 4, radicals $R^6$; $C_3$-$C_8$-cycloalkyl which may be partially or fully halogenated and/or may be substituted by one or more, e.g. 1, 2, 3 or 4, radicals $R^6$; $C_2$-$C_{10}$-alkenyl which may be partially or fully halogenated and/or may be substituted by one or more, e.g. 1, 2, 3 or 4, radicals $R^6$; $C_2$-$C_{10}$-alkynyl which may be partially or fully halogenated and/or may be substituted by one or more, e.g. 1, 2, 3 or 4, radicals $R^6$; —N($R^8$)$R^9$; —N($R^8$)C(=O)$R^6$; —Si($R^{14}$)$_2R^{13}$; —O$R^7$; —S$R^7$; —S(O)$_mR^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, radicals $R^{10}$;

with the proviso that $R^2$ is not —O$R^7$ if Y is O;

or $R^1$ and $R^2$, together with the atoms to which they are bound, form a partially unsaturated or aromatic 5- or 6-membered heterocyclic ring which, apart from the nitrogen atom of the imine group and the group Y if this is different from a chemical bond, optionally contains 1 or 2 further heteroatoms or heteroatom groups selected from N, O, S, NO, SO and SO$_2$, as ring members, where the heterocyclic ring may carry 1, 2 or 3 substituents $R^6$;

$R^3$ is selected from the group consisting of hydrogen; cyano; $C_1$-$C_{10}$-alkyl which may be partially or fully halogenated and/or may be substituted by one or more, e.g. 1, 2, 3 or 4, radicals $R^6$; $C_3$-$C_8$-cycloalkyl which may be partially or fully halogenated and/or may be substituted by one or more, e.g. 1, 2, 3 or 4, radicals $R^6$; $C_2$-$C_{10}$-alkenyl which may be partially or fully halogenated and/or may be substituted by one or more, e.g. 1, 2, 3 or 4, radicals $R^6$; $C_2$-$C_{10}$-alkynyl which may be partially or fully halogenated and/or may be substituted by one or more, e.g. 1, 2, 3 or 4, radicals $R^6$; —N($R^8$)$R^9$; —Si($R^{14}$)$_2R^{13}$; —O$R^7$; —S$R^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, radicals $R^{10}$;

or $R^2$ and $R^3$ together form a group =C$R^{11}R^{12}$; =S(O)$_mR^7$; =S(O)$_m$N($R^8$)$R^9$; =N$R^8$; or =NO$R^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or N$R^{18}$ and/or 1 or 2 of the CH$_2$ groups of the alkylene chain may be replaced by a group C=O, C=S and/or C=N$R^{18}$; and/or the alkylene chain may be substituted by one or more, e.g. 1, 2, 3 or 4, radicals selected from the group consisting of halogen, $C_1$-$C_6$-haloalkyl, $C_1$-$C_6$-alkoxy, $C_1$-$C_6$-haloalkoxy, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, radicals $R^{10}$;

each $R^4$ is independently selected from the group consisting of halogen; cyano; azido; nitro; —SCN; SF$_5$; $C_1$-$C_6$-alkyl which may be partially or fully halogenated and/or may be substituted by one or more, e.g. 1, 2, 3 or 4, radicals $R^6$; $C_3$-$C_8$-cycloalkyl which may be partially or fully halogenated and/or may be substituted by one or more, e.g. 1, 2, 3 or 4, radicals $R^6$; $C_2$-$C_6$-alkenyl which may be partially or fully halogenated and/or may be substituted by one or more, e.g. 1, 2, 3 or 4, radicals $R^6$; $C_2$-$C_6$-alkynyl which may be partially or fully halogenated and/or may be substituted by one or more, e.g. 1, 2, 3 or 4, radicals $R^6$; —Si($R^{14}$)$_2R^{13}$; —O$R^7$; —OS(O)$_nR^7$; —S$R^7$; —S(O)$_n$N($R^8$)$R^9$; —N($R^8$)$R^9$; —N($R^8$)C(=O)$R^6$; C(=O)$R^6$; —C(=O)O$R^7$; —C(=N$R^8$)H; —C(=N$R^8$)$R^6$; —C(=O)N($R^8$)$R^9$; C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, radicals $R^{10}$;

or two radicals $R^4$ bound on adjacent carbon atoms may be together a group selected from —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$N$R^8$—, —CH$_2$CH=N—, —CH=CH—N$R^8$—, —OCH=N— and —SCH=N—, thus forming, together with the carbon atoms to which they are bound, a 5- or 6-membered ring, where the hydrogen atoms of the above groups may be replaced by one or more, e.g. 1, 2, 3 or 4, substituents selected from halogen, methyl, halomethyl, hydroxyl, methoxy and halomethoxy or one or more, e.g. 1 or 2, CH$_2$ groups of the above groups may be replaced by a C=O group;

each $R^5$ is independently selected from the group consisting of halogen, cyano, azido, nitro, —SCN, SF$_5$, $C_1$-$C_6$-alkyl which may be partially or fully halogenated and/or may be substituted by one or more, e.g. 1, 2, 3 or 4, radicals $R^6$, $C_3$-$C_8$-cycloalkyl which may be partially or fully halogenated and/or may be substituted by one or more, e.g. 1, 2, 3 or 4, radicals $R^6$, $C_2$-$C_6$-alkenyl which may be partially or fully halogenated and/or may be substituted by one or more, e.g. 1, 2, 3 or 4, radicals $R^6$, $C_2$-$C_6$-alkynyl which may be partially or fully halogenated and/or may be substituted by one or more, e.g. 1, 2, 3 or 4, radicals $R^6$, —Si($R^{14}$)$_2R^{13}$, —OS(O)$_nR^7$, —S(O)$_n$N($R^8$)$R^9$, —N($R^8$)$R^9$, N($R^8$)C(=O)$R^6$, —C(=O)$R^6$, —C(=O)O$R^7$, —C(=S)$R^6$, —C(=S)O$R^7$, —C(=N$R^8$)$R^6$, —C(=O)N($R^8$)$R^9$, —C(=S)N($R^8$)$R^9$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, radicals $R^{10}$;

each $R^6$ is independently selected from the group consisting of cyano, azido, nitro, SCN, SF$_5$, $C_3$-$C_8$-cycloalkyl, $C_3$-$C_8$-halocycloalkyl, —Si($R^{14}$)$_2R^{13}$, —OSO$_2R^7$, —S$R^7$, —S(O)$_mR^7$, —S(O)$_n$N($R^8$)$R^9$, —N($R^8$)$R^9$, —C(=O)N($R^8$)$R^9$, —C(=S)N($R^8$)$R^9$, —C(=O)O$R^7$, —C(=O)$R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, radicals $R^{10}$;

and, in case $R^6$ is bound to a cycloalkyl group or to a heterocyclic ring formed by $R^1$ and $R^2$ together with the atoms to which they are bound, $R^6$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

and in groups —C(=O)$R^6$, —C(=S)$R^6$, —C(=N$R^8$)$R^6$ and —N($R^8$)C(=O)$R^6$, $R^6$ may additionally be selected from hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

or two geminally bound radicals $R^6$ together form a group selected from =$CR^{11}R^{12}$, =S(O)$_m R^7$, =S(O)$_m$N($R^8$)$R^9$, =N$R^8$, =NO$R^7$ and =NN$R^8$;

or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

each $R^7$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, $C_3$-$C_8$-cycloalkyl, $C_3$-$C_8$-cycloalkyl $C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2 R^{13}$, —$SR^8$, —S(O)$_m R^7$, —S(O)$_n$N($R^8$)$R^9$, —N($R^8$)$R^9$, —N=$CR^{15}R^{16}$, —C(=O)$R^{17}$, —C(=O)N($R^8$)$R^9$, —C(=S)N($R^8$)$R^9$, —C(=O)O$R^{17}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, radicals $R^{10}$;

with the proviso that $R^7$ is not $C_1$-$C_6$-alkoxy or $C_1$-$C_6$-haloalkoxy if it is bound to an oxygen atom (like in a group O$R^7$);

each $R^8$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —S(O)$_m R^{20}$, —S(O)$_n$N($R^{21}$)$R^{22}$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, radicals $R^{10}$;

each $R^9$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —S(O)$_m R^{20}$, —S(O)$_n$N($R^{21}$)$R^{22}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, radicals $R^{10}$;

or $R^8$ and $R^9$ together form a group =$CR^{11}R^{12}$;

or $R^8$ and $R^9$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$;

each $R^{10}$ is independently selected from the group consisting of halogen, cyano, azido, nitro, —SCN, $SF_5$, $C_1$-$C_{10}$-alkyl which may be partially or fully halogenated and/or may be substituted by one or more, e.g. 1, 2, 3 or 4, radicals $R^{19}$, $C_3$-$C_8$-cycloalkyl which may be partially or fully halogenated and/or may be substituted by one or more, e.g. 1, 2, 3 or 4, radicals $R^{19}$, $C_2$-$C_{10}$-alkenyl which may be partially or fully halogenated and/or may be substituted by one or more, e.g. 1, 2, 3 or 4, radicals $R^{19}$, $C_2$-$C_{10}$-alkynyl which may be partially or fully halogenated and/or may be substituted by one or more, e.g. 1, 2, 3 or 4, radicals $R^{19}$, —Si($R^{14}$)$_2 R^{13}$, —O$R^{20}$, —OS(O)$_n R^{20}$, —S$R^{20}$, —S(O)$_n$N($R^{21}$)$R^{22}$, —N($R^{21}$)$R^{22}$, C(=O)$R^{19}$, —C(=O)O$R^{20}$, —C(=N$R^{21}$)$R^{19}$, —C(=O)N($R^{21}$)$R^{22}$, —C(=S)N($R^{21}$)$R^{22}$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more, e.g. 1, 2, 3 or 4, radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —O$CH_2CH_2CH_2$—, —OCH=CH$CH_2$—, —$CH_2$ $OCH_2CH_2$—, —$OCH_2CH_2O$—, —$OCH_2OCH_2$—, —$CH_2CH_2CH_2$—, —$CH=CHCH_2$—, —$CH_2CH_2O$—, —$CH=CHO$—, —$CH_2OCH_2$—, —$CH_2C(=O)O$—, —$C(=O)OCH_2$—, —$O(CH_2)O$—, —$SCH_2CH_2CH_2$—, —$SCH=CHCH_2$—, —$CH_2SCH_2CH_2$—, —$SCH_2CH_2S$—, —$SCH_2SCH_2$—, —$CH_2CH_2S$—, —$CH=CHS$—, —$CH_2SCH_2$—, —$CH_2C(=S)S$—, —$C(=S)SCH_2$—, —$S(CH_2)S$—, —$CH_2CH_2NR^{21}$—, —$CH_2CH=N$—, —$CH=CH-NR^{21}$—, —$OCH=N$— and —$SCH=N$—, thus forming, together with the atoms to which they are bound, a 5- or 6-membered ring, where the hydrogen atoms of the above groups may be replaced by one or more, e.g. 1, 2, 3 or 4, substituents selected from halogen, methyl, halomethyl, hydroxyl, methoxy and halomethoxy or one or more, e.g. 1 or 2, $CH_2$ groups of the above groups may be replaced by a $C=O$ group;

$R^{11}$, $R^{12}$ are, independently of each other and independently of each occurrence, selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy $C_1$-$C_6$-alkyl, $C_1$-$C_6$-haloalkoxy $C_1$-$C_6$-alkyl, $C_1$-$C_6$-alkoxy, $C_1$-$C_6$-haloalkoxy, —$C(=O)R^{19}$, —$C(=O)OR^{20}$, —$C(=NR^{21})R^{22}$; —$C(=O)N(R^{21})R^{22}$; —$C(=S)N(R^{21})R^{22}$; phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, which may be substituted by one or more, e.g. 1, 2, 3 or 4, radicals $R^{10}$;

$R^{13}$, $R^{14}$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^{15}$, $R^{16}$ are, independently of each other and independently of each occurrence, selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-haloalkoxy-$C_1$-$C_6$-alkyl, phenyl which may be substituted by 1, 2, 3, 4, or 5 radicals $R^{19}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, which may be substituted by one or more, e.g. 1, 2, 3 or 4, radicals $R^{10}$;

each $R^{17}$ is independently selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl and benzyl;

each $R^{18}$ is independently defined like $R^3$;

each $R^{19}$ is independently selected from the group consisting of cyano, azido, nitro, —SCN, $SF_5$, $C_3$-$C_8$-cycloalkyl, $C_3$-$C_8$-halocycloalkyl, —$Si(R^{14})_2R^{13}$, —$OR^{20}$, —$OSO_2R^{20}$, —$SR^{20}$, —$S(O)_nN(R^{21})R^{22}$, —$N(R^{21})R^{22}$, —$C(O)N(R^{21})R^{22}$, —$C(=S)N(R^{21})R^{22}$, —$C(=O)OR^{20}$, —$C(=O)R^{20}$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

and, in case $R^{19}$ is bound to a cycloalkyl group, $R^{19}$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl and $C_2$-$C_6$-haloalkynyl;

and in groups —$C(=O)R^{19}$, $R^{19}$ may additionally be selected from hydrogen, halogen, $C_1$-$C_6$-alkyl, $C_2$-$C_6$-alkenyl, $C_2$-$C_6$-haloalkenyl, $C_2$-$C_6$-alkynyl, and $C_2$-$C_6$-haloalkynyl;

or two geminally bound radicals $R^{19}$ together form a group selected from =$CR^{11}R^{12}$, =$S(O)_mR^{20}$, =$S(O)_mN(R^{21})R^{22}$, =$NR^{21}$, =$NOR^{20}$ and =$NNR^{21}$;

or two radicals $R^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

each $R^{20}$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl $C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$Si(R^{14})_2R^{13}$, $C_1$-$C_6$-alkylaminosulfonyl, amino, $C_1$-$C_6$-alkylamino, di-($C_1$-$C_6$-alkyl)-amino, $C_1$-$C_6$-alkylcarbonyl, $C_1$-$C_6$-haloalkylcarbonyl, aminocarbonyl, $C_1$-$C_6$-alkylaminocarbonyl, di-($C_1$-$C_6$-alkyl)-aminocarbonyl, $C_1$-$C_6$-alkoxycarbonyl, $C_1$-$C_6$-haloalkoxycarbonyl, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

with the proviso that $R^{20}$ is not $C_1$-$C_6$-alkoxy or $C_1$-$C_6$-haloalkoxy if it is bound to an oxygen atom;

$R^{21}$ and $R^{22}$ are independently of each other and independently of each occurrence selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl $C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals selected from halogen, $C_1$-$C_6$-alkyl, $C_1$-$C_6$-haloalkyl, $C_1$-$C_6$-alkoxy and $C_1$-$C_6$-haloalkoxy;

each m is independently 1 or 2;
each n is independently 0, 1 or 2;
p is 0, 1, 2, 3 or 4; and
q is 0, 1, 2, 3, 4 or 5;
and the stereoisomers and agriculturally or veterinarily acceptable salts thereof.

The present invention also provides an agricultural composition comprising at least one compound of the formula I as defined herein and/or an agriculturally acceptable salt thereof and at least one liquid or solid carrier.

The present invention also provides a veterinary composition comprising at least one compound of the formula I as defined herein and/or a veterinarily acceptable salt thereof and at least one liquid or solid carrier.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt thereof as defined herein.

The present invention also relates to plant propagation material, in particular seed, comprising at least one compound of formula I and/or an agriculturally acceptable salt thereof as defined herein.

The present invention further relates to a method for treating or protecting an animal from infestation or infection by parasites which comprises bringing the animal in contact with a parasiticidally effective amount of a compound of the formula I or a veterinarily acceptable salt thereof as defined herein. Bringing the animal in contact with the compound I, its salt or the veterinary composition of the invention means applying or administering it to the animal.

The term "steroisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isoxazoline ring carrying radical X. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof. Cis/trans isomers may be present with respect to the imine group.

The compounds of the present invention may be amorphous or may exist in one or more different crystalline states (polymorphs) which may have a different macroscopic properties such as stability or show different biological properties such as activities.

The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_6$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" as used herein includes all the generative parts of the plant such as seeds and vegetative plant material such as cuttings and tubers (e.g.

potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat. Protoc. 2007; 2(5):1225-35. Curr. Opin. Chem. Biol. 2006 October; 10(5): 487-91. Epub 2006 Aug. 28, Biomaterials. 2001 March; 22(5):405-17, Bioconjug Chem. 2005 January-February; 16(1):113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus *bacillus*, particularly from *bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora* infestans derived from the mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "$C_1$-$C_{10}$-alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 4 ("$C_1$-$C_4$-alkyl"), 1 to 6 ("$C_1$-$C_6$-alkyl"), 1 to 8 ("$C_1$-$C_8$-alkyl") or 1 to 10 ("$C_1$-$C_{10}$-alkyl") carbon atoms. $C_1$-$C_2$-Alkyl is methyl or ethyl. $C_1$-$C_4$-Alkyl is additionally propyl, isopropyl, butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof.

The term "$C_1$-$C_{10}$-haloalkyl" as used herein, which is also expressed as "$C_1$-$C_{10}$-alkyl which is partially or fully halogenated", refers to straight-chain or branched alkyl groups having 1 to 2 ("$C_1$-$C_2$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "$C_2$-$C_{10}$-alkenyl" as used herein and in the alkenyl moiety of alkenyloxy and the like refers to monounsaturated straight-chain or branched hydrocarbon radicals having 2 to 4 ("$C_2$-$C_4$-alkenyl"), 2 to 6 ("$C_2$-$C_6$-alkenyl"), 2 to 8 ("$C_2$-$C_8$-alkenyl"), 3 to 8 ("$C_3$-$C_8$-alkenyl"), 2 to 10 ("$C_2$-$C_{10}$-alkenyl") or 3 to 10 ("$C_3$-$C_{10}$-alkenyl") carbon atoms and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_8$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "$C_2$-$C_{10}$-haloalkenyl" as used herein, which is also expressed as "$C_1$-$C_{10}$-alkenyl which is partially or fully halogenated", and the haloalkenyl moieties in haloalkenyloxy, haloalkenylcarbonyl and the like refers to unsaturated straight-chain or branched hydrocarbon radicals having 2 to 4 ("$C_2$-$C_4$-haloalkenyl"), 2 to 6 ("$C_2$-$C_6$-haloalkenyl"), 2 to 8 ("$C_2$-$C_6$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "$C_2$-$C_{10}$-alkynyl" as used herein and the alkynyl moieties in alkynyloxy, alkynylcarbonyl and the like refers to straight-chain or branched hydrocarbon groups having 2 to 4 ("$C_2$-$C_4$-alkynyl"), 2 to 6 ("$C_2$-$C_6$-alkynyl"), 2 to 8 ("$C_2$-$C_8$-alkynyl"), 3 to 8 ("$C_3$-$C_8$-alkynyl"), 2 to 10 ("$C_2$-$C_{10}$-alkynyl") or 3 to 10 ("$C_3$-$C_8$-alkynyl") carbon atoms and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "$C_2$-$C_{10}$-haloalkynyl" as used herein, which is also expressed as "$C_1$-$C_{10}$-alkynyl which is partially or fully halogenated", and the haloalkynyl moieties in haloalkynyloxy, haloalkynylcarbonyl and the like refers to unsaturated straight-chain or branched hydrocarbon radicals having 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 3 to 6 ("$C_3$-$C_6$-haloalkynyl"), 2 to 8 ("$C_2$-$C_8$-haloalkynyl"), 3 to 8 ("$C_3$-$C_8$-haloalkynyl"), 2 to 10 ("$C_2$-$C_{10}$-haloalkynyl") or 3 to 10 ("$C_3$-$C_{10}$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "$C_3$-$C_8$-cycloalkyl" as used herein refers to mono- or bi- or polycyclic saturated hydrocarbon radicals having 3 to 8, in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl.

The term "$C_3$-$C_8$-halocycloalkyl" as used herein, which is also expressed as "$C_3$-$C_8$-cycloalkyl which is partially or fully halogenated", and the halocycloalkyl moieties in halocycloalkoxy, halocycloalkylcarbonyl and the like refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") carbon ring members (as mentioned above) in which some or all of the hydrogen atoms are replaced by halogen atoms as mentioned above, in particular fluorine, chlorine and bromine.

The term "$C_3$-$C_8$-cycloalkyl-$C_1$-$C_4$-alkyl" refers to a $C_3$-$C_8$-cycloalkyl group as defined above which is bound to the remainder of the molecule via a $C_1$-$C_4$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cycloppentylethyl, cyclopentylpropyl, cyclohexylmethyl, cyclohexylethyl, cyclohexylpropyl, and the like.

The term "$C_1$-$C_2$-alkoxy" is a $C_1$-$C_2$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_4$-Alkoxy is additionally, for example, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_2$-alkylthio" is a $C_1$-$C_2$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_4$-Alkylthio is additionally, for example, n-propylthio, 1-methylethylthio (isopropylthio), butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $S(O)C_2F_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [$S(O)_2$] group. The term "$C_1$-$C_4$-alkylsulfonyl" is a $C_1$-$C_4$-alkyl group, as defined above, attached via a sulfonyl [$S(O)_2$] group. The term "$C_1$-$C_6$-alkylsulfonyl" is a $C_1$-$C_6$-alkyl group, as defined above, attached via a sulfonyl [$S(O)_2$] group. The term "$C_1$-$C_{10}$-alkylsulfonyl" is a $C_1$-$C_{10}$-alkyl group, as defined above, attached via a sulfonyl [$S(O)_2$] group. $C_1$-$C_2$-Alkylsulfonyl is methylsulfonyl or ethylsulfonyl. $C_1$-$C_4$-Alkylsulfonyl is additionally, for example, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl [$S(O)_2$] group. The term "$C_1$-$C_4$-haloalkylsulfonyl" is a $C_1$-$C_4$-haloalkyl group, as defined above, attached via a sulfonyl [$S(O)_2$] group. The term "$C_1$-$C_6$-haloalkylsulfonyl" is a $C_1$-$C_6$-haloalkyl group, as defined above, attached via a sulfonyl [$S(O)_2$] group. The term "$C_1$-$C_{10}$-haloalkylsulfonyl" is a $C_1$-$C_{10}$-haloalkyl group, as defined above, attached via a sulfonyl [$S(O)_2$] group. $C_1$-$C_2$-Haloalkylsulfonyl is, for example, $S(O)_2CH_2F$, $S(O)_2CHF_2$, $S(O)_2CF_3$, $S(O)_2CH_2Cl$, $S(O)_2CHCl_2$, $S(O)_2CCl_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or $S(O)_2C_2F_5$. $C_1$-$C_4$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $S(O)_2CH_2$—$C_2F_5$, $S(O)_2CF_2$—$C_2F_5$, 1-($CH_2F$)-2-fluoroethylsulfonyl, 1-($CH_2Cl$)-2-chloroethylsulfonyl, 1-($CH_2Br$)-2-bromoethylsulfonyl, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The term "3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members" as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl include:

Oxiranyl, aziridinyl, oxetidinyl (radical of trimethylene oxide), thietidinyl (radical of trimethylene sulfide), azetidinyl, 2-tetrahydrofuranyl, 3-tetrahydrofuranyl, 1,3-dioxolane-2-yl, 1,3-dioxolane-4-yl, 2-tetrahydrothienyl, 3-tetrahydrothienyl, 1,3-thiolane-2-yl, 1,3-dithiolane-4-yl, 1-thia-3-oxolan-2-yl, 1-thia-3-oxolan-4-yl, 1-thia-3-oxolan-5-yl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 3-tetrahydropyranyl, 4-tetrahydropyranyl, 1,3-dioxan-2-yl, 1,3-dioxan-4-yl, 1,3-dioxan-5-yl, 1,4-dioxan-2-yl, 2-thianyl, 3-thianyl, 4-thianyl, 1,3-dithian-2-yl, 1,3-dithian-4-yl, 1,3-dithian-5-yl, 1,4-dithian-2-yl, 1-oxa-3-thian-2-yl, 1-oxa-3-thian-4-yl, 1-oxa-3-thian-5-yl, 1-oxa-3-thian-6-yl, 1-oxa-4-thian-2-yl, 1-oxa-4-thian-3-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, 2- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-1-, -2-, -3-, -4-, -5-, -6- or -7-yl, 2,3,4,7-tetrahydro[1H]oxepin-1-, -2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclyl is 5- or 6-membered aromatic heterocyclyl (hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

$C_2$-$C_7$-alkylene is divalent branched or preferably unbranched saturated aliphatic chain having 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$ The remarks made below concerning preferred embodiments of the variables of the compounds of formula I, especially with respect to their substituents X, Y, $A^1$, $A^2$, $A^3$, $A^4$, $B^1$, $B^2$, $B^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, m, n, p and q, the features of the use and method according to the invention and of the composition of the invention are valid both on their own and, in particular, in every possible combination with each other.

As a matter of course, the q radicals $R^5$ replace a hydrogen atom on a carbon ring atom. For instance, if $B^1$, $B^2$ or $B^3$ is defined to be CH and if this position is to be substituted by a radical $R^5$, then $B^1$, $B^2$ or $B^3$ is of course C—$R^5$. If there is more than one radical $R^5$, these can be the same or different.

As a matter of course, the p radicals $R^4$ replace a hydrogen atom on a carbon ring atom. For instance, if $A^1$, $A^2$, $A^3$ or $A^4$ is defined to be CH and if this position is to be substituted by a radical $R^4$, then $A^1$, $A^2$, $A^3$ or $A^4$ is of course C—$R^4$. If there is more than one radical $R^4$, these can be the same or different.

Preferably, at most two of $A^1$, $A^2$, $A^3$ and $A^4$ are N. In one embodiment, $A^1$, $A^2$, $A^3$ and $A^4$ are CH. In an alternative embodiment, $A^1$, $A^3$ and $A^4$ are CH and $A^2$ is N. In an alternative embodiment, $A^1$ and $A^4$ are CH and $A^2$ and $A^3$ are N. In an alternative embodiment, $A^1$ and $A^2$ are CH and $A^3$ and $A^4$ are N. In an alternative embodiment, $A^2$ and $A^4$ are CH and $A^1$ and $A^3$ are N.

More preferably, $A^4$ is CH.

More preferably, $A^1$ and $A^3$ are CH.

Even more preferably, $A^1$, $A^3$ and $A^4$ are CH and $A^2$ is CH or N and in particular CH.

In a preferred embodiment, the ring comprising the groups $A^1$, $A^2$, $A^3$ or $A^4$ as ring members carries 0, 1 or 2, preferably 0 or 1 and in particular 1 substituent $R^4$. In other words, p is preferably 0, 1 or 2, more preferably 0 or 1 and in particular 1. In case $A^2$ is CH and p is 1, the substituent $R^4$ is preferably bound on the position of $A^2$ (or $A^3$, which is interchangeable with $A^2$ in case all of $A^1$, $A^2$, $A^3$ and $A^4$ are CH). In other words, $A^2$ is in this case preferably C—$R^4$. In case $A^2$ is N and p is 1, the substituent $R^4$ is preferably bound on the position of $A^3$. In other words, $A^3$ is in this case preferably C—$R^4$.

In case p is 2, two substituents $R^4$ bound on adjacent carbon atoms preferably form together a group selected from —$CH_2CH_2CH_2CH_2$— and —CH=CH—CH=CH— and more preferably —CH=CH—CH=CH—, thus yielding a fused phenyl ring.

Preferably, at most one of $B^1$, $B^2$ and $B^3$ is N. More preferably, $B^1$, $B^2$ and $B^3$ are CH or $B^1$ and $B^2$ are CH and $B^3$ is N.

q is preferably 0, 1, 2 or 3, more preferably 1, 2 or 3, even more preferably 2 or 3 and in particular 2. If q is 3 and $B^1$, $B^2$ and $B^3$ are CH, then the three substituents $R^5$ are preferably bound in the positions of $B^1$, $B^2$ and $B^3$; $B^1$, $B^2$ and $B^3$ thus being C—$R^5$. If q is 2 and $B^1$, $B^2$ and $B^3$ are CH, then the two substituents $R^5$ are preferably bound in the positions of $B^1$ and $B^3$; $B^1$ and $B^3$ thus being C—$R^5$. $B^2$ in this case is preferably CH. In case $B^1$ and $B^2$ are CH and $B^3$ is N, q is preferably 1. In this case, $R^5$ is preferably bound in the position of $B^1$, $B^1$ thus being C—$R^5$.

X is preferably selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl and $C_3$-$C_6$-halocycloalkyl. More preferably, X is selected from the group consisting of $C_1$-$C_4$-alkyl, $C_1$-$C_4$-haloalkyl, $C_3$-$C_6$-cycloalkyl and $C_3$-$C_6$-halocycloalkyl. Even more preferably, X is selected from the group consisting of $C_1$-$C_4$-alkyl and $C_1$-$C_4$-haloalkyl. In particular, X is $C_1$-$C_4$-haloalkyl, specifically $C_1$-$C_2$-haloalkyl and more specifically halomethyl, in particular fluoromethyl, such as fluoromethyl, difluoromethyl and trifluoromethyl, and is very specifically trifluoromethyl.

Y is preferably O, $NR^3$ or a chemical bond.

In one preferred embodiment, Y is O.

In an alternatively preferred embodiment, Y is $NR^3$. $R^3$ has one of the meanings given above or preferably one of the preferred meanings given below.

In an alternatively preferred embodiment, Y is a chemical bond.

More preferably, Y is O or $NR^3$. $R^3$ has one of the meanings given above or preferably one of the preferred meanings given below.

Preferably, $R^1$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; —C(=O)$OR^7$; —C(=O)N($R^8$)$R^9$; —C(=S)$R^6$; —C(=S)$OR^7$; —C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$; or $R^1$ and $R^2$ together are —$CH_2CH_2$—, —$CH_2CH_2CH_2$— or —$CR^{61}$=$CR^{61}$—, where $R^7$, $R^8$, $R^9$ and $R^{10}$ have one of the meanings given above or in particular one of the preferred meanings given below and $R^{61}$ is hydrogen or has one of the meanings given above or in particular is hydrogen or has one of the preferred meanings given below for $R^6$.

More preferably, $R^1$ is selected from the group consisting of hydrogen; cyano; alkyl which may be partially or fully halogenated and/or may be substituted by one or more, e.g. 1, 2, 3 or 4, preferably 1 or 2, more preferably 1, radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$ and $R^{10}$ have one of the meanings given above or in particular one of the preferred meanings given below.

Even more preferably, $R^1$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more, e.g. 1, 2, 3 or 4, preferably 1 or 2, more preferably 1, radicals $R^6$, and —C(=O)$R^6$; where $R^6$ has one of the meanings given above or in particular one of the preferred meanings given below.

In particular, $R^1$ is selected from the group consisting of hydrogen, cyano, $C_1$-$C_{10}$-alkyl, preferably $C_1$-$C_6$-alkyl, more preferably $C_1$-$C_4$-alkyl, which may be partially or fully halogenated and/or may be substituted by one or more, e.g. 1, 2, 3 or 4, preferably 1 or 2, more preferably 1, radicals $R^6$; cyclopropyl; $C_1$-$C_4$-alkoxy; $C_1$-$C_4$-haloalkoxy, and —C(=O)$R^6$; where $R^6$ has one of the meanings given above or in particular one of the preferred meanings given below.

Specifically, $R^1$ is selected from the group consisting of hydrogen; cyano; $C_1$-$C_6$-alkyl; $C_1$-$C_4$-haloalkyl, specifically $C_1$-$C_4$-fluoroalkyl; $C_1$-$C_4$-alkyl which is substituted by one radical $R^6$; cyclopropyl; $C_1$-$C_4$-alkoxy; $C_1$-$C_4$-haloalkoxy, specifically $C_1$-$C_4$-fluoroalkoxy; and —C(=O)$R^6$; where $R^6$ has one of the meanings given above or preferably one of the preferred meanings given below. More specifically, $R^1$ is selected from the group consisting of hydrogen; cyano; $C_1$-$C_6$-alkyl; cyclopropyl; $C_1$-$C_4$-alkoxy; and $C_1$-$C_4$-alkyl-carbonyl.

In case $R^1$ is selected from $C_1$-$C_{10}$-alkyl, preferably $C_1$-$C_6$-alkyl, more preferably $C_1$-$C_4$-alkyl, which is substituted by one or more, e.g. 1, 2, 3 or 4, preferably 1 or 2, more preferably 1, radicals $R^6$, $R^6$ is more preferably selected from $C_3$-$C_6$-cycloalkyl, $C_3$-$C_6$-halocycloalkyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, more preferably from a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, even more preferably from a 5- or 6-membered saturated, partially unsaturated or aromatic heterocyclic ring containing 1, 2 or 3 heteroatoms selected from N, O and S, as ring members, where the heterocyclic ring may be substituted by one or more, e.g. 1, 2 or 3, preferably 1 or 2, more preferably 1, radicals $R^{10}$, in particular from a 5- or 6-membered heteroaromatic ring containing 1 heteroatom selected from N, O and S and optionally 1 or two further N atoms, as ring members, where the heteroaromatic ring may be substituted by one or more, e.g. 1, 2 or 3, preferably 1 or 2, more preferably 1, radicals $R^{10}$, and is specifically 6-membered heteroaromatic ring selected from pyridinyl, pyridazinyl, pyrimidinyl, pyrazinyl and 1,3,5-triazinyl, preferably from pyridyl and pyrimidinyl, where the heteroaromatic ring may be substituted by one or more, e.g. 1, 2 or 3, preferably 1 or 2, more preferably 1, radicals $R^{10}$, where $R^{10}$ has one of the meanings given above or in particular one of the preferred meanings given below.

Preferably, $R^2$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —N($R^8$)$R^9$; —N($R^8$)C(=O)$R^6$; —Si($R^{14}$)$_2$$R^{13}$; —O$R^7$; —S$R^7$; —S(O)$_n$N($R^8$)$R^9$; —C(=O)$R^6$; —C(=O)O$R^7$;
—C(=O)N($R^8$)$R^9$; —C(=S)$R^6$; —C(=S)O$R^7$, —C(=S)N($R^8$)$R^9$; —C(=N$R^8$)$R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$;

with the proviso that $R^2$ is not —O$R^7$ if Y is O;

or $R^1$ and $R^2$ together are —$CH_2CH_2$—, —$CH_2CH_2CH_2$— or —$CR^{61}$=$CR^{61}$—;

or $R^2$ and $R^3$ together form a group =$CR^{11}R^{12}$; =S(O)$_m$$R^7$; =S(O)$_m$N($R^8$)$R^9$; =N$R^8$; or =NO$R^7$;

or $R^2$ and $R^3$ together form a $C_2$-$C_7$-alkylene chain, thus forming, together with the nitrogen atom to which they are bound, a 3-, 4-, 5-, 6-, 7- or 8-membered ring, where the alkylene chain may be interrupted by 1 or two O, S and/or $NR^{18}$ and/or 1 or 2 of the $CH_2$ groups of the alkylene chain may be replaced by a group C=O, C=S and/or C=$NR^{18}$; and/or the alkylene chain may be substituted by one or more, e.g. 1, 2, 3 or 4, preferably 1 or 2, more preferably 1, radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^7$, $R^8$, $R^9$, $R^{10}$, $R^{11}$, $R^{12}$, $R^{13}$, $R^{14}$ and $R^{18}$ have one of the meanings given above or in particular one of the preferred meanings given below and $R^{61}$ is hydrogen or has one of the meanings given above or in particular is hydrogen or has one of the preferred meanings given below for $R^6$.

In case Y is a chemical bond, $R^2$ is more preferably selected from a substituent bound via a heteroatom, such as —N($R^8$)$R^9$; —N($R^8$)C(=O)$R^6$; —O$R^7$; —S$R^7$; —S(O)$_m$$R^7$; —S(O)$_n$N($R^8$)$R^9$ and an N-bound 3-, 4-, 5-, 6- or 7-membered saturated, partially unsaturated or aromatic heterocyclic ring containing 1 N atom as ring member and optionally 1 or 2 further heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

In case Y is a chemical bond, $R^2$ is even more preferably selected from —N($R^8$)$R^9$; —N($R^8$)C(=O)$R^6$; —O$R^7$; —S$R^7$; —S(O)$_m$$R^7$ and S(O)$_n$N($R^8$)$R^9$, in particular from —N($R^8$)$R^9$; —N($R^8$)C(=O)$R^6$; —O$R^7$ and —S$R^7$, and specifically from —N($R^8$)$R^9$; —N($R^8$)C(=O)$R^6$ and —O$R^7$, where $R^6$, $R^7$, $R^8$ and $R^9$ have one of the meanings given above or in particular one of the preferred meanings given below.

In case Y is not a chemical bond, $R^2$ is more preferably selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$, —C(=S)N($R^8$)$R^9$; —C(=N$R^8$)$R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

In case Y is not a chemical bond, $R^2$ is even more preferably selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$, —C(=S)N($R^8$)$R^9$; —C(=N$R^8$)$R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$,
where $R^6$, $R^7$, $R^8$, $R^9$ and $R^{10}$ have one of the meanings given above or in particular one of the preferred meanings given below.

In case Y is not a chemical bond, $R^2$ is in particular selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=N$R^8$)$R^6$, phenyl which may be substituted by 1, 2, 3, 4 or 5, preferably 1 or 2 and in particular 1, radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$,
where $R^6$, $R^7$, $R^8$, $R^9$ and $R^{10}$ have one of the meanings given above or in particular one of the preferred meanings given below.

In case Y is not a chemical bond, $R^2$ is more particularly selected from the group consisting of hydrogen; $C_1$-$C_{10}$-alkyl, preferably $C_1$-$C_4$-alkyl, which may be partially or fully halogenated and/or may be substituted by one or more, e.g. 1, 2, 3 or 4, preferably 1 or 2, more preferably 1, radicals $R^6$; —C(=O)$R^6$, —C(=O)O$R^7$; —C(=O)N($R^8$)$R^9$; and —C(=N$R^8$)$R^6$, where $R^6$, $R^7$, $R^8$ and $R^9$ have one of the meanings given above or in particular one of the preferred meanings given below.

In case Y is not a chemical bond, $R^2$ is specifically selected from the group consisting of hydrogen; $C_1$-$C_4$-alkyl, $C_1$-$C_4$-haloalkyl, in particular $C_1$-$C_4$-fluoroalkyl, $C_1$-$C_4$-alkyl which is substituted by one or more, e.g. 1, 2, 3 or 4, preferably 1 or 2, more preferably 1, radicals $R^{6a}$; —C(=O)$R^{6b}$, —C(=O)O$R^7$, —C(=O)N($R^8$)$R^9$ and —C(=N$R^8$)$R^6$, where
$R^{6a}$ is selected from CN, —C(=O)$R^{6b}$; —C(=O)N($R^8$)$R^9$, —C(=O)O$R^7$; phenyl which may be substituted by 1, 2, 3, 4 or 5 radicals $R^{10}$, a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, preferably from a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, more preferably from a 5- or 6-membered saturated, partially unsaturated or aromatic heterocyclic ring containing 1, 2 or 3 heteroatoms selected from N, O and S, as ring members, where the heterocyclic ring may be substituted by one or more, e.g. 1, 2 or 3, preferably 1 or 2, more preferably 1, radicals $R^{10}$, in particular from a 5- or 6-membered heteroaromatic ring containing 1 heteroatom selected from N, O and S and optionally 1 or two further N atoms, as ring members, where the heteroaromatic ring may be substituted by one or more, e.g. 1, 2 or 3, preferably 1 or 2, more preferably 1, radicals $R^{10}$, and is specifically 6-membered heteroaromatic ring selected from pyridinyl, pyridazinyl, pyrimidinyl, pyrazinyl and 1,3,5-triazinyl, preferably from pyridyl and pyrimidinyl, where the heteroaromatic ring may be substituted by one or more, e.g. 1, 2 or 3, preferably 1 or 2, more preferably 1, radicals $R^{10}$, where $R^{10}$ has one of the meanings given above or in particular one of the preferred meanings given below; and
$R^{6b}$ is selected from hydrogen, $C_1$-$C_6$-alkyl, $C_1$-$C_6$-haloalkyl or has one of the meanings given for $R^{6a}$;
where $R^6$, $R^7$, $R^8$ and $R^9$ have one of the meanings given above or in particular one of the preferred meanings given below.

More specifically, $R^2$ is selected from the group consisting of hydrogen; $C_1$-$C_4$-alkyl; $C_1$-$C_4$-haloalkyl; a methyl group substituted by a radical $R^{6a}$ selected from CN, phenyl, which may carry 1, 2 or 3 substituents $R^{10a}$, —C(=O)$R^{6b}$; —C(=O)N($R^{8a}$)$R^{9a}$ and —C(=O)O$R^{7a}$; —C(=O)$R^{6c}$; —C(=O)N($R^{8a}$)$R^{9a}$; and —C(=N$R^{8a}$)$R^{6d}$,
where
$R^{6b}$ and $R^{6c}$ are independently selected from $C_1$-$C_4$-alkyl, $C_1$-$C_4$-haloalkyl, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy;
$R^{6d}$ is selected from N($R^{8a}$)$R^{9a}$;
$R^{7a}$ is selected from hydrogen, $C_1$-$C_4$-alkyl, $C_1$-$C_4$-haloalkyl, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy;
each $R^{8a}$ is independently selected from hydrogen, cyano, $C_1$-$C_6$-alkyl which may be partially or fully halogenated and/or may be substituted by one or more radicals $R^{19}$, $C_2$-$C_4$-alkenyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl $C_1$-$C_4$-alkyl, $C_3$-$C_6$-halocycloalkyl-$C_1$-$C_4$-alkyl, —S(O)$_n$N($R^{21}$)$R^{22}$, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$ haloalkyl, $C_1$-$C_4$-alkoxy and $C_1$-$C_4$-haloalkoxy;
each $R^{9a}$ is independently selected from hydrogen, cyano, $C_1$-$C_6$-alkyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl $C_1$-$C_4$-alkyl, $C_3$-$C_6$-halocycloalkyl-$C_1$-$C_4$-alkyl, —S(O)$_m$$R^{20}$, —S(O)$_n$N($R^{21}$)$R^{22}$, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy; or
$R^{8a}$ and $R^{9a}$ together form a group =C$R^{11}R^{12}$; or $R^{8a}$ and $R^{9a}$, together with the nitrogen atom to which they are bound, form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$; and $R^{10a}$ is selected from halogen, CN, $C_1$-$C_4$-alkyl, $C_1$-$C_4$-haloalkyl, $C_1$-$C_4$-alkoxy and $C_1$-$C_4$-haloalkoxy;

where $R^{10}$, $R^{11}$, $R^{12}$ and $R^{19}$ have one of the general meanings given above or in particular one of the preferred meanings given below.

In the above preferred embodiment of $R^2$, $R^{11}$ is preferably hydrogen or methyl and $R^{12}$ is preferably $C_1$-$C_6$-alkoxy, $C_1$-$C_6$-haloalkoxy, —C(=O)$R^{19}$, —C(=O)O$R^{20}$, or —C(=O)N($R^{21}$)$R^{22}$.

In the above preferred embodiment of $R^2$, $R^{9a}$, if it does not form together with $R^{8a}$ a group =C$R^{11}R^{12}$ or together with $R^{8a}$ and the N atom to which they are bound a heterocyclic ring, is preferably selected from hydrogen, cyano, $C_1$-$C_4$-alkyl, $C_1$-$C_4$-haloalkyl, cyclopropyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl and is more preferably hydrogen or $C_1$-$C_4$-alkyl.

In the above preferred embodiment of $R^2$, $R^{8a}$, if it does not form together with $R^{9a}$ a group =C$R^{11}R^{12}$ or together with $R^{9a}$ and the N atom to which they are bound a heterocyclic ring, is preferably selected from CN, $C_1$-$C_6$-alkyl; $C_1$-$C_6$-haloalkyl; $C_1$-$C_4$-alkyl which carries one radical $R^{19}$; $C_2$-$C_6$-alkenyl; $C_2$-$C_6$-haloalkenyl; $C_2$-$C_4$-alkenyl which is substituted by one radical $R^{19}$; $C_3$-$C_6$-cycloalkyl; $C_3$-$C_6$-halocycloalkyl; $C_3$-$C_6$-cycloalkyl-$C_1$-$C_4$-alkyl; $C_3$-$C_6$-halocycloalkyl-$C_1$-$C_4$-alkyl; —S(O)$_m R^{20}$; —S(O)$_n$N($R^{21}$)$R^{22}$; phenyl; benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy.

If $R^{8a}$ and $R^{9a}$, together with the nitrogen atom to which they are bound, form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, this is preferably a 3, 5 or 6-membered saturated heterocyclic ring which may additionally containing 1 further heteroatom or heteroatom group selected from N, O, S, NO, SO and $SO_2$, as ring member.

In a particularly preferred embodiment of the invention, the combination of Y and $R^2$ is $NR^3$—CO—N($R^8$)$R^9$. In this case, $R^3$ is preferably selected from hydrogen, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl and is more preferably H or $C_1$-$C_4$-alkyl, and $R^8$ and $R^9$ have preferably one of the preferred meanings given below for $R^8$ and $R^9$ or have more preferably one of the general or preferred meanings given above for $R^{8a}$ and $R^{9a}$. Preferably $R^3$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —N($R^8$)$R^9$; —Si($R^{14}$)$_2 R^{13}$; —O$R^7$; —S$R^7$; —S(O)$_m R^7$; —S(O)$_n$N($R^8 R^9$); —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$;

or $R^2$ and $R^3$ together form a group =C$R^{11}R^{12}$; =S(O)$_m R^7$; =S(O)$_m$N($R^8$)$R^9$; =N$R^8$; or =NO$R^7$;

or $R^2$ and $R^3$ together form a $C_2$-$C_7$-alkylene chain, thus forming, together with the nitrogen atom to which they are bound, a 3-, 4-, 5-, 6-, 7- or 8-membered ring, where the alkylene chain may be interrupted by 1 or two O, S and/or $NR^{18}$ and/or 1 or 2 of the $CH_2$ groups of the alkylene chain may be replaced by a group C=O, C=S and/or C=$NR^{18}$; and/or the alkylene chain may be substituted by one or more, e.g. 1, 2, 3 or 4, preferably 1 or 2, more preferably 1, radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$, $R^{10}$, $R^{11}$, $R^{12}$, $R^{13}$, $R^{14}$ and $R^{18}$ have one of the meanings given above or in particular one of the preferred meanings given below.

More preferably, $R^3$ is selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

Even more preferably, $R^3$ is selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$ and —C(=N$R^8$)$R^6$; where $R^6$, $R^7$, $R^8$ and $R^9$ have one of the meanings given above and in particular one of the preferred meanings given below.

In particular, $R^3$ is selected from the group consisting of hydrogen; $C_1$-$C_6$-alkyl which may be partially or fully halogenated and/or may be substituted by one or more, e.g. 1, 2, 3 or 4, preferably 1 or 2, more preferably 1, radicals $R^6$; —C(=O)$R^6$ and —C(=O)N($R^8$)$R^9$; where $R^6$, $R^8$ and $R^9$ have one of the meanings given above and in particular one of the preferred meanings given below. Preferably, in this case, $R^6$ as a $C_1$-$C_6$-alkyl substituent, is selected from CN, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio and a 5- or 6-membered hetaryl ring containing 1, 2 or 3 heteroatoms selected from N, O and S as ring members and being optionally substituted by 1, 2 or 3 radicals $R^{10}$. In this case, $R^6$ as a CO substituent, is preferably selected from $C_1$-$C_6$-alkyl, $C_1$-$C_6$-haloalkyl, $C_1$-$C_6$-alkoxy and $C_1$-$C_6$-haloalkoxy. In this case, $R^8$ and $R^9$ are preferably selected from hydrogen and $C_1$-$C_6$-alkyl.

More particularly, $R^3$ is selected from the group consisting of hydrogen, $C_1$-$C_4$-alkyl, $C_1$-$C_4$-haloalkyl and —C(=O)$R^6$, and is specifically selected from the group consisting of hydrogen, $C_1$-$C_4$-alkyl and $C_1$-$C_4$-haloalkyl, where $R^6$ has one of the meanings given above or in particular one of the preferred meanings given below and is specifically $C_1$-$C_4$-alkyl.

Preferably, each $R^4$ is independently selected from halogen; cyano; nitro; —SCN; $SF_5$; $C_1$-$C_6$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_6$-alkenyl which may be partially or fully halogenated and/or may be substituted by one or more, e.g. 1, 2, 3 or 4, preferably 1 or 2, more preferably 1, radicals $R^6$; $C_2$-$C_6$-alkynyl which may be partially or fully halogenated and/or may be substituted by one or more, e.g. 1, 2, 3 or 4, preferably 1 or 2, more preferably 1, radicals $R^6$; —Si($R^{14}$)$_2R^{13}$; —O$R^7$; —OS(O)$_nR^7$; —S$R^7$; —S(O)$_nR^7$; —S(O)$_n$N($R^8$)$R^9$; —N($R^8$)$R^9$; —N($R^8$)C(=O)$R^6$; C(=O)$R^6$; —C(=O)O$R^7$; —C(=N$R^8$)H; —C(=N$R^8$)$R^6$; —C(=O)N($R^8$)$R^9$; C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$;

or two radicals $R^4$ bound on adjacent carbon atoms may be together a group selected from —$CH_2CH_2CH_2CH_2$—, —CH=CH—CH=CH—, —N=CH—CH=CH—, —CH=N—CH=CH—, —N=CH—N=CH—, —O$CH_2CH_2CH_2$—, —OCH=CH$CH_2$—, —$CH_2$O$CH_2CH_2$—, —O$CH_2CH_2$O—, —O$CH_2$O$CH_2$—, —$CH_2CH_2CH_2$—, —CH=CH$CH_2$—, —$CH_2CH_2$O—, —CH=CHO—, —$CH_2$O$CH_2$—, —$CH_2$C(=O)O—, —C(=O)O$CH_2$—, —O($CH_2$)O—, —S$CH_2CH_2$—, —SCH=CH$CH_2$—, —$CH_2$S$CH_2CH_2$—, —$CH_2$S—, —CH=CHS—, —$CH_2$S$CH_2$—, —$CH_2C$(=S)S—, —C(=S)S$CH_2$—, —S($CH_2$)S—, —$CH_2CH_2$N$R^8$—, —$CH_2$CH=N—, —CH=CH—N$R^8$—, —OCH=N—, and —SCH=N—, thus forming, together with the carbon atoms to which they are bound, a 5- or 6-membered ring, where the hydrogen atoms of the above groups may be replaced by one or more, e.g. 1, 2, 3 or 4, preferably 1 or 2, more preferably 1, substituents selected from halogen, methyl, halomethyl, hydroxyl, methoxy and halo-methoxy or one or more, e.g. 1 or 2, $CH_2$ groups of the above groups may be replaced by a C=O group, where $R^6$, $R^7$, $R^8$, $R^9$, $R^{10}$, $R^{13}$ and $R^{14}$ have one of the meanings given above or in particular one of the preferred meanings given below.

More preferably, each $R^4$ is independently selected from halogen; cyano; nitro; —SCN; $C_1$-$C_6$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; —O$R^7$; —OS(O)$_nR^7$; —S$R^7$; —S(O)$_nR^7$; —S(O)$_n$N($R^8$)$R^9$; —N($R^8$)$R^9$; —N($R^8$)C(=O)$R^6$; C(=O)$R^6$; —C(=O)O$R^7$; —C(=N$R^8$)$R^6$; —C(=O)N($R^8$)$R^9$; —C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$;

or two radicals $R^4$ bound on adjacent carbon atoms may be together a group selected from —$CH_2CH_2CH_2CH_2$—, —CH=CH—CH=CH—, —N=CH—CH=CH—, —CH=N—CH=CH—, —N=CH—N=CH—, —O$CH_2CH_2CH_2$—, —OCH=CH$CH_2$—, —$CH_2$O$CH_2CH_2$—, —O$CH_2CH_2$O—, —O$CH_2$O$CH_2$—, —$CH_2CH_2CH_2$—, —CH=CH$CH_2$—, —$CH_2CH_2$O—, —CH=CHO—, —$CH_2$O$CH_2$—, —$CH_2$C(=O)O—, —C(=O)O$CH_2$—, —O($CH_2$)O—, —S$CH_2CH_2$—, —SCH=CH$CH_2$—, —$CH_2$S$CH_2CH_2$—, —$CH_2$S—, —S$CH_2$S—, —$CH_2CH_2$N$R^8$—, —$CH_2$CH=N—, —OCH=N—, and —SCH=N—, thus forming, together with the carbon atoms to which they are bound, a 5- or 6-membered ring, where the hydrogen atoms of the above groups may be replaced by one or more, e.g. 1, 2, 3 or 4, preferably 1 or 2, more preferably 1, substituents selected from halogen, methyl, halomethyl, hydroxyl, methoxy and halo-methoxy or one or more, e.g. 1 or 2, $CH_2$ groups of the above groups may be replaced by a C=O group, where $R^6$, $R^7$, $R^8$, $R^9$ and $R^{10}$ have one of the meanings given above or in particular one of the preferred meanings given below.

Even more preferably, each $R^4$ is independently selected from halogen; cyano; nitro; —SCN; $C_1$-$C_6$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; —O$R^7$; —OS(O)$_nR^7$; —S$R^7$; —S(O)$_mR^7$; —S(O)$_n$N($R^8$)$R^9$; —N($R^8$)$R^9$; C(=O)$R^6$; —C(=O)O$R^7$; —C(=N$R^8$)$R^6$; —C(=O)N($R^8$)$R^9$; —C(=S)N($R^8$)$R^9$ and phenyl which may be substituted by 1, 2, 3, 4 or 5 radicals $R^{10}$ where $R^6$, $R^7$, $R^8$, $R^9$ and $R^{10}$ have one of the meanings given above or in particular one of the preferred meanings given below.

In particular, each $R^4$ is independently selected from halogen; cyano; nitro; $C_1$-$C_6$-alkyl; $C_1$-$C_6$-haloalkyl; $C_1$-$C_6$-alkoxy; $C_1$-$C_6$-haloalkoxy; and phenyl which may be substituted by 1, 2, 3, 4 or 5 radicals $R^{10}$;

or two radicals $R^4$ bound on adjacent carbon atoms may be together a group selected from —$CH_2CH_2CH_2CH_2$— and —CH=CH—CH=CH— and preferably —CH=CH—CH=CH—, where $R^{10}$ has one of the meanings given above or in particular one of the preferred meanings given below.

More particularly, each $R^4$ is independently selected from halogen, cyano, $C_1$-$C_6$-alkyl, preferably $C_1$-$C_4$-alkyl, more preferably methyl, and $C_1$-$C_4$-haloalkyl, preferably $C_1$-$C_2$-haloalkyl.

Preferably, each $R^5$ is independently selected from the group consisting of halogen, cyano, nitro, —SCN, $SF_5$, $C_1$-$C_6$-alkyl, $C_1$-$C_6$-alkyl which may be partially or fully halogenated and/or may be substituted by one or more, e.g. 1, 2, 3 or 4, preferably 1 or 2, more preferably 1, radicals $R^6$, $C_3$-$C_8$-cycloalkyl which may be partially or fully halogenated and/or may be substituted by one or more, e.g. 1, 2, 3 or 4, preferably 1 or 2, more preferably 1, radicals $R^6$, $C_2$-$C_6$-alkenyl which may be partially or fully halogenated and/or may be substituted by one or more, e.g. 1, 2, 3 or 4, preferably 1 or 2, more preferably 1, radicals $R^6$, $C_2$-$C_6$-alkynyl which may be partially or fully halogenated and/or may be substituted by one or more, e.g. 1, 2, 3 or 4, preferably 1 or 2, more preferably 1, radicals $R^6$, $Si(R^{14})_2R^{13}$, $OR^7$, $OS(O)_nR^7$, $S(O)_mR^7$, $NR^8R^9$, $N(R^8)C(=O)R^6$, $C(=O)R^6$, $C(=O)OR^7$, $C(=NR^8)R^6$, $C(=S)NR^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$, $R^{10}$, $R^{13}$ and $R^{14}$ have one of the meanings given above or in particular one of the preferred meanings given below.

More preferably, each $R^5$ is independently selected from the group consisting of halogen, cyano, nitro, $C_1$-$C_6$-alkyl, $C_1$-$C_6$-alkyl which may be partially or fully halogenated and/or may be substituted by one or more, e.g. 1, 2, 3 or 4, preferably 1 or 2, more preferably 1, radicals $R^6$, $OR^7$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$ and $R^{10}$ have one of the meanings given above or in particular one of the preferred meanings given below.

Even more preferably, each $R^5$ is independently selected from the group consisting of halogen, $C_1$-$C_6$-alkyl, $C_1$-$C_6$-haloalkyl, $C_1$-$C_6$-alkoxy and $C_1$-$C_6$-haloalkoxy, in particular from halogen, $C_1$-$C_4$-alkyl and $C_1$-$C_2$-haloalkyl and is specifically halogen, more specifically chlorine, or $C_1$-$C_2$-haloalkyl, specifically $CF_3$.

In case $R^6$ is a substituent on an alkyl, alkenyl or alkynyl group, it is preferably selected from the group consisting of cyano, azido, nitro, —SCN, $SF_5$, $C_3$-$C_8$-cycloalkyl, $C_3$-$C_8$-halocycloalkyl, —$Si(R^{14})_2R^{13}$, —$OR^7$, —$OSO_2R^7$, —$S(O)_mR^7$, —$S(O)_nN(R^8)R^9$, —$N(R^8)R^9$, —$C(=O)N(R^8)R^9$, —$C(=S)N(R^8)R^9$, —$C(=O)OR^7$, —$C(=O)R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$; or two geminally bound radicals $R^6$ together form a group selected from =$CR^{11}R^{12}$, =$S(O)_mR^7$, =$S(O)_nN(R^8)R^9$, =$NR^8$, =$NOR^7$ and =$NNR^8$; or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members, where $R^7$, $R^8$, $R^9$, $R^{10}$, $R^{11}$, $R^{12}$, $R^{13}$, $R^{14}$ and $R^{19}$ have one of the meanings given above or in particular one of the preferred meanings given below.

In case $R^6$ is a substituent on an alkyl, alkenyl or alkynyl group, it is more preferably selected from the group consisting of cyano, $C_3$-$C_8$-cycloalkyl, $C_3$-$C_8$-halocycloalkyl, —$OR^7$, —$SR^7$, —$C(=O)N(R^8)R^9$, —$C(=S)N(R^8)R^9$, —$C(=O)OR^7$, —$C(=O)R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

where $R^7$, $R^8$, $R^9$ and $R^{10}$ have one of the meanings given above or in particular one of the preferred meanings given below.

In case $R^6$ is a substituent on an alkyl, alkenyl or alkynyl group, it is even more preferably selected from the group consisting of cyano, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-haloalkylthio, —$C(=O)N(R^8)R^9$, —$C(=S)N(R^8)R^9$, —$C(=O)OR^7$, —$C(=O)R^{19}$, phenyl which may be substituted by 1, 2, 3, 4 or 5 radicals $R^{10}$, and a 5- or 6-membered heteroaromatic ring containing 1, 2 or 3 heteroatoms selected from N, O and S, as ring members, where the heteroaromatic ring may be substituted by one or more radicals $R^{10}$;

where $R^{10}$ has one of the meanings given above or in particular one of the preferred meanings given below.

In case $R^6$ is a substituent on an alkyl, alkenyl or alkynyl group, it is in particular selected from the group consisting of cyano, $C_3$-$C_6$-cycloalkyl, $C_3$-$C_6$-halocycloalkyl, —$C(=O)N(R^8)R^9$, —$C(=S)N(R^8)R^9$, —$C(=O)OR^7$, —$C(=O)R^{19}$, phenyl which may be substituted by 1, 2, 3, 4 or 5 radicals $R^{10}$, and a 5- or 6-membered heteroaromatic ring containing 1, 2 or 3 heteroatoms selected from N, O and S, as ring members, where the heteroaromatic ring may be substituted by one or more radicals $R^{10}$;

where $R^{10}$ has one of the meanings given above or in particular one of the preferred meanings given below.

In case $R^6$ is a substituent on a cycloalkyl group, it is preferably selected from the group consisting of cyano, azido, nitro, —SCN, $SF_5$, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$Si(R^{14})_2R^{13}$, —$OR^7$, —$OSO_2R^7$, —$SR^7$, —$S(O)_mR^7$, —$S(O)_nN(R^8)R^9$, —$N(R^8)R^9$, —$C(=O)N(R^8)R^9$, —$C(=S)N(R^8)R^9$, —$C(=O)OR^7$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

or two geminally bound radicals $R^6$ together form a group selected from $=CR^{11}R^{12}$, $=S(O)_mR^7$, $=S(O)_mN(R^8)R^9$, $=NR^8$, $=NOR^7$ and $=NNR^8$;

or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members, where $R^7$, $R^8$, $R^9$, $R^{10}$, $R^{11}$, $R^{12}$, $R^{13}$ and $R^{14}$ have one of the meanings given above or in particular one of the preferred meanings given below.

In case $R^6$ is a substituent on a cycloalkyl group, it is more preferably selected from the group consisting of halogen, cyano, $C_1$-$C_6$-alkyl, $C_1$-$C_6$-haloalkyl, $C_1$-$C_6$-alkoxy-$C_1$-$C_6$alkyl, $-OR^7$, $-OSO_2R^7$, $-SR^7$, $-S(O)_mR^7$, $-S(O)_nN(R^8)R^9$, $-N(R^8)R^9$, $-C(=O)N(R^8)R^9$, $-C(=S)N(R^8)R^9$, $-C(=O)OR^7$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

where $R^7$, $R^8$, $R^9$ and $R^{10}$ have one of the meanings given above or in particular one of the preferred meanings given below.

In case $R^6$ is a substituent on a cycloalkyl group, it is even more preferably selected from the group consisting of halogen, $C_1$-$C_4$-alkyl, $C_1$-$C_3$-haloalkyl, $C_1$-$C_4$-alkoxy and $C_1$-$C_3$-haloalkoxy. In particular, $R^6$ as a substituent on a cycloalkyl group is selected from halogen, $C_1$-$C_4$-alkyl and $C_1$-$C_3$-haloalkyl.

In case $R^6$ is a substituent on $C(=O)$, $C(=S)$ or $C(=NR^8)$, it is preferably selected from the group consisting of hydrogen, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, $-OR^7$, $-SR^7$, $-N(R^8)R^9$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

where $R^7$, $R^8$, $R^9$ and $R^{10}$ have one of the meanings given above or in particular one of the preferred meanings given below.

In case $R^6$ is a substituent on $C(=O)$, $C(=S)$ or $C(=NR^8)$, it is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

where $R^{10}$ has one of the meanings given above or in particular one of the preferred meanings given below.

In case $R^6$ is a substituent on $C(=O)$, $C(=S)$ or $C(=NR^8)$, it is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

where $R^{10}$ has one of the meanings given above or in particular one of the preferred meanings given below.

In case $R^6$ is a substituent on $C(=O)$, $C(=S)$ or $C(=NR^8)$, it is even more preferably selected from the group consisting of $C_1$-$C_4$-alkyl, $C_1$-$C_3$-haloalkyl, $C_3$-$C_6$-cycloalkyl, $C_3$-$C_6$-halocycloalkyl, $C_1$-$C_4$-alkoxy, $C_1$-$C_3$-haloalkoxy, phenyl which may be substituted by 1, 2, 3, 4 or 5 radicals $R^{10}$, and a 5- or 6-membered heteroaromatic ring containing 1, 2 or 3 heteroatoms selected from N, O and S, as ring members, where the heteroaromatic ring may be substituted by one or more radicals $R^{10}$;

where $R^{10}$ has one of the meanings given above or in particular one of the preferred meanings given below.

Preferably, each $R^7$ is independently selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^{10}$ has one of the meanings given above or in particular one of the preferred meanings given below.

More preferably, each $R^7$ is independently selected from the group consisting of hydrogen, $C_1$-$C_6$-alkyl, $C_1$-$C_6$-haloalkyl, phenyl which may be substituted by 1, 2, 3, 4 or 5 radicals $R^{10}$; and a 5- or 6-membered heteroaromatic ring containing 1, 2 or 3 heteroatoms selected from N, O and S, as ring members, where the heteroaromatic ring may be substituted by one or more radicals $R^{10}$; where $R^{10}$ has one of the meanings given above or in particular one of the preferred meanings given below.

$R^8$ and $R^9$ are independently of each other and independently of each occurrence preferably selected from the group consisting of hydrogen, cyano, $C_1$-$C_6$-alkyl which may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, $C_3$-$C_8$-cycloalkyl, $C_3$-$C_8$-halocycloalkyl, $C_3$-$C_8$-cycloalkyl-$C_1$-$C_6$-alkyl, $S(O)_mR^{20}$, $S(O)_nNR^{21}R^{22}$, phenyl which may be substituted by 1, 2, 3, 4 or 5 radicals $R^{10}$, benzyl wherein the phenyl moiety may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$; where $R^{10}$ has one of the meanings given above or in particular one of the preferred meanings given below; or $R^8$ and $R^9$ together form a group $=CR^{11}R^{12}$; or $R^8$ and $R^9$, together with the nitrogen atom to which they are bound, form a 3-, 4-, 5-, 6- or 7-membered saturated, partially unsaturated or aromatic, preferably a saturated, heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$.

In the above preferred embodiment of $R^8$ and $R^8$, $R^{11}$ is preferably hydrogen or methyl and $R^{12}$ is preferably $C_1$-$C_6$-alkoxy, $C_1$-$C_6$-haloalkoxy, —C(=O)$R^{19}$, —C(=O)O$R^{20}$, or —C(=O)N($R^{21}$)$R^{22}$.

In the above preferred embodiment of $R^8$ and $R^8$, $R^9$, if it does not form together with $R^8$ a group =C$R^{11}R^{12}$ or together with $R^8$ and the N atom to which they are bound a heterocyclic ring, is preferably selected from hydrogen, cyano, $C_1$-$C_4$-alkyl, $C_1$-$C_4$-haloalkyl, cyclopropyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl and is more preferably hydrogen or $C_1$-$C_4$-alkyl.

In the above preferred embodiment of $R^8$ and $R^8$, $R^8$, if it does not form together with $R^9$ a group =C$R^{11}R^{12}$ or together with $R^9$ and the N atom to which they are bound a heterocyclic ring, is preferably selected from CN, $C_1$-$C_6$-alkyl, $C_1$-$C_6$-haloalkyl; $C_1$-$C_4$-alkyl which carries one radical $R^{19}$; $C_2$-$C_6$-alkenyl; $C_2$-$C_6$-haloalkenyl; $C_2$-$C_4$-alkenyl which is substituted by one radical $R^{19}$; $C_3$-$C_6$-cycloalkyl; $C_3$-$C_6$-halocycloalkyl; $C_3$-$C_6$-cycloalkyl-$C_1$-$C_4$-alkyl; $C_3$-$C_6$-halocycloalkyl-$C_1$-$C_4$-alkyl; —S(O)$_m$$R^{20}$; —S(O)$_n$N($R^{21}$)$R^{22}$; phenyl; benzyl and a 5- or 6-membered saturated, partially unsaturated or aromatic heterocyclic ring containing 1, 2 or 3 heteroatoms or heteroatom groups selected from N, O, S, NO, SO and SO$_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy.

If $R^8$ and $R^9$, together with the nitrogen atom to which they are bound, form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and SO$_2$, as ring members, this is preferably a 3, 5 or 6-membered saturated heterocyclic ring which may additionally containing 1 further heteroatom or heteroatom group selected from N, O, S, NO, SO and SO$_2$, as ring member.

Specifically, $R^8$ and $R^9$ are independently of each other and independently of each occurrence selected from the group consisting of hydrogen, $C_1$-$C_6$-alkyl, $C_1$-$C_6$-haloalkyl, $C_2$-$C_6$-alkynyl, $C_3$-$C_8$-cycloalkyl-$C_1$-$C_6$-alkyl, benzyl wherein the phenyl moiety may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$. More specifically, $R^9$ is hydrogen or $C_1$-$C_4$-alkyl and $R^8$ has one of the meanings specified above.

Preferably, each $R^{10}$ is independently selected from the group consisting of halogen, cyano, $C_1$-$C_{10}$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, —O$R^7$, —OS(O)$_n$$R^7$, —S$R^7$, —S(O)$_m$$R^7$, —S(O)$_n$N($R^8$)$R^9$, —N($R^8$)$R^9$, C(=O)$R^6$, —C(=O)O$R^7$, —C(=O)N($R^8$)$R^9$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and SO$_2$, as ring members, which may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; or two radicals $R^{10}$ bound on adjacent atoms together form a group selected from —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, and —O(CH$_2$)O—, thus forming, together with the atoms to which they are bound, a 5- or 6-membered ring, where the hydrogen atoms of the above groups may be replaced by one or more substituents selected from halogen, methyl, halomethyl, hydroxyl, methoxy and halomethoxy or one or more CH$_2$ groups of the above groups may be replaced by a C=O group, where $R^6$, $R^7$, $R^8$ and $R^9$ have one of the general or in particular one of the preferred meanings given above.

More preferably, each $R^{10}$ is independently selected from the group consisting of halogen, cyano, $C_1$-$C_{10}$-alkyl which may be partially or fully halogenated and/or may be substituted by one or more radicals $R^6$, —O$R^7$, —N($R^8$)$R^9$, C(=O)$R^6$, —C(=O)O$R^7$, —C(=O)N($R^8$)$R^9$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and SO$_2$, as ring members, which may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; where $R^6$, $R^7$, $R^8$ and $R^9$ have one of the general or in particular one of the preferred meanings given above.

Even more preferably, each $R^{10}$ is independently selected from the group consisting of halogen, $C_1$-$C_4$-alkyl, $C_1$-$C_4$-haloalkyl, $C_1$-$C_4$-alkoxy and $C_1$-$C_4$-haloalkoxy. In particular, each $R^{10}$ is independently selected from the group consisting of halogen, $C_1$-$C_4$-alkyl and $C_1$-$C_4$-haloalkyl and is specifically halogen, more specifically chlorine.

Preferably, $R^{11}$ and $R^{12}$ are, independently of each other and independently of each occurrence, selected from the group consisting of hydrogen, halogen, $C_1$-$C_6$-alkyl and $C_1$-$C_6$-haloalkyl. More preferably, $R^{11}$ and $R^{12}$ are, independently of each other and independently of each occurrence, selected from the group consisting of hydrogen, halogen and $C_1$-$C_6$-alkyl and in particular from the group consisting of hydrogen and halogen. Specifically, they are hydrogen.

Preferably, $R^{13}$ and $R^{14}$ are, independently of each other and independently of each occurrence, selected from $C_1$-$C_4$-alkyl and are in particular methyl.

Preferably, $R^{15}$ and $R^{16}$ are, independently of each other and independently of each occurrence, selected from the group consisting of $C_1$-$C_6$-alkyl, $C_1$-$C_6$-haloalkyl and phenyl which may be substituted by 1, 2, 3, 4, or 5 radicals $R^{10}$; where $R^{10}$ has one of the general or in particular one of the preferred meanings given above.

Preferably, each $R^{17}$ is independently selected from the group consisting of $C_1$-$C_6$-alkyl, $C_1$-$C_6$-haloalkyl, $C_3$-$C_8$-cycloalkyl, $C_3$-$C_8$-halocycloalkyl, phenyl and benzyl. More preferably, each $R^{17}$ is independently selected from the group consisting of $C_1$-$C_6$-alkyl, $C_1$-$C_6$-haloalkyl and phenyl and is in particular $C_1$-$C_4$-alkyl or $C_1$-$C_3$-haloalkyl.

Preferably, each $R^{18}$ is independently selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$ and —C(=N$R^8$)$R^6$; where $R^6$, $R^7$, $R^8$ and $R^9$ have one of the general or in particular one of the preferred meanings given above.

More preferably, each $R^{18}$ is selected from the group consisting of hydrogen; $C_1$-$C_6$-alkyl which may be partially or fully halogenated and/or may be substituted by one or more, e.g. 1, 2, 3 or 4, preferably 1 or 2, more preferably 1, radicals $R^6$; —C(=O)$R^6$ and —C(=O)N($R^8$)$R^9$; where $R^6$, $R^8$ and $R^9$ have one of the general or in particular one of the preferred meanings given above. Preferably, in this case, $R^6$ as a $C_1$-$C_6$-alkyl substituent, is selected from CN, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio and a 5- or 6-membered hetaryl ring containing 1, 2 or 3 heteroatoms selected from N, O and S as ring members and being optionally substituted by 1, 2 or 3 radicals $R^{10}$. In this case, $R^6$ as a CO substituent, is preferably selected from $C_1$-$C_6$-alkyl, $C_1$-$C_6$-haloalkyl, $C_1$-$C_6$-alkoxy and $C_1$-$C_6$-haloalkoxy. In this case, $R^8$ and $R^9$ are preferably selected from hydrogen and $C_1$-$C_6$-alkyl.

In particular, each $R^{18}$ is selected from the group consisting of hydrogen, $C_1$-$C_4$-alkyl, $C_1$-$C_4$-haloalkyl and —C(=O)$R^6$, and is specifically selected from the group consisting of hydrogen, $C_1$-$C_4$-alkyl and —C(=O)$R^6$, where $R^6$ has one of the general or in particular one of the preferred meanings given above and is specifically $C_1$-$C_4$-alkyl.

In case $R^{19}$ is a substituent on an alkyl, alkenyl or alkynyl group, it is preferably selected from the group consisting of cyano, $C_3$-$C_6$-cycloalkyl, $C_3$-$C_6$-halocycloalkyl, —O$R^{20}$, —C(=O)N($R^{21}$)$R^{22}$, —C(=S)N($R^{21}$)$R^{22}$, —C(=O)O$R^{20}$, —C(=O)$R^{20}$, phenyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$;
where
$R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy;
$R^{20}$ is selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; and
$R^{21}$ and $R^{22}$, independently of each other and independently of each occurrence, are selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$.

In case $R^{19}$ is a substituent on a cycloalkyl group, it is preferably selected from the group consisting of cyano, $C_1$-$C_4$-alkyl, $C_1$-$C_4$-haloalkyl, $C_3$-$C_6$-cycloalkyl, $C_3$-$C_6$-halocycloalkyl, —C(=O)N($R^{21}$)$R^{22}$, —C(=S)N($R^{21}$)$R^{22}$, —C(=O)O$R^{20}$, —C(=O)$R^{20}$, phenyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$;
where
$R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy;
$R^{20}$ is selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; and
$R^{21}$ and $R^{22}$, independently of each other and independently of each occurrence, are selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$.

In case $R^{19}$ is a substituent on a C(=O) group, it is preferably selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_3$-$C_6$-cycloalkyl-$C_1$-$C_4$-alkyl, phenyl which may be substituted by 1, 2, 3, 4 or 5 radicals $R^{10}$, benzyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy.

$R^{20}$ is preferably selected from the group consisting of hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_6$-cycloalkyl-$C_1$-$C_4$-alkyl, phenyl which may be substituted by 1, 2, 3, 4 or 5 radicals $R^{10}$, benzyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy.

$R^{21}$ and $R^{22}$, independently of each other and independently of each occurrence, are preferably selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, benzyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy;
or $R^{21}$ and $R^{22}$, together with the nitrogen atom to which they are bound, may form a 5- or 6-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals selected from halogen, $C_1$-$C_6$-alkyl, $C_1$-$C_6$ haloalkyl, $C_1$-$C_6$-alkoxy and $C_1$-$C_6$-haloalkoxy.

One particularly preferred embodiment of the invention refers to compounds of the formula I-1

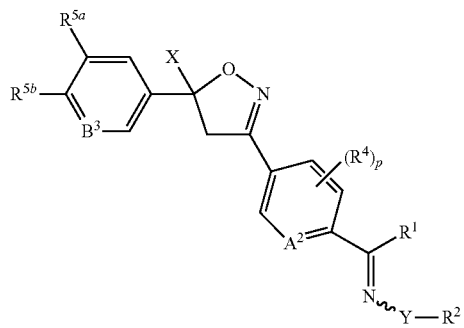

(I-1)

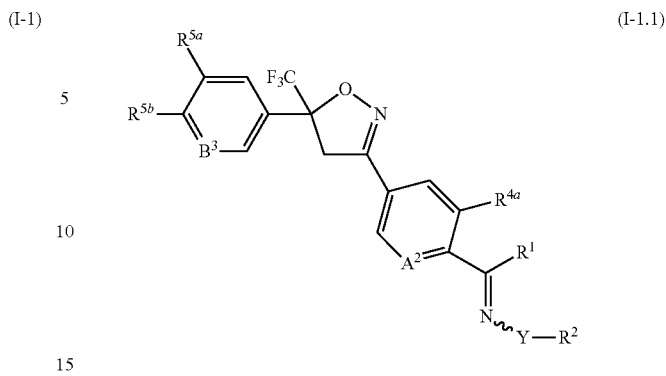

(I-1.1)

wherein
$B^3$ is $CR^{5c}$ or N;
X, Y, $R^1$, $R^2$, $R^4$, $A^2$ and p have one of the general or in particular one of the preferred meanings given above; and $R^{5a}$, $R^{5b}$, $R^{5c}$ are hydrogen or have one of the general or in particular one of the preferred meanings given above for $R^5$.

Preferably, in compounds I-1, $R^{5a}$, $R^{5c}$ are, independently of each other, selected from the group consisting of hydrogen, halogen, cyano, nitro, SCN, $SF_5$, $C_1$-$C_6$-alkyl which may be partially or fully halogenated and/or may be substituted by one or more, e.g. 1, 2, 3 or 4, preferably 1 or 2, more preferably 1, radicals $R^6$, $C_3$-$C_8$-cycloalkyl which may be partially or fully halogenated and/or may be substituted by one or more, e.g. 1, 2, 3 or 4, preferably 1 or 2, more preferably 1, radicals $R^6$, $OR^7$, $SR^7$, $S(O)_mR^7$, $NR^8R^9$, $C(=O)R^6$, $-C(=O)OR^7$, $C(=NR^8)R^6$, $C(=S)NR^6$; and $R^{5b}$ is selected from the group consisting of hydrogen, halogen, cyano, nitro, —SCN, $SF_5$, $C_1$-$C_6$-alkyl which may be partially or fully halogenated and/or may be substituted by one or more, e.g. 1, 2, 3 or 4, preferably 1 or 2, more preferably 1, radicals $R^6$, $C_3$-$C_8$-cycloalkyl which may be partially or fully halogenated and/or may be substituted by one or more, e.g. 1, 2, 3 or 4, preferably 1 or 2, more preferably 1, radicals $R^6$, $C_2$-$C_6$-alkenyl which may be partially or fully halogenated and/or may be substituted by one or more, e.g. 1, 2, 3 or 4, preferably 1 or 2, more preferably 1, radicals $R^6$, $C_2$-$C_6$-alkynyl which may be partially or fully halogenated and/or may be substituted by one or more, e.g. 1, 2, 3 or 4, preferably 1 or 2, more preferably 1, radicals $R^6$, $Si(R^{14})_2R^{13}$, $OR^7$, $SR^7$, $OS(O)_nR^7$, $S(O)_mR^7$, $NR^8R^9$, $N(R^8)C(=O)R^6$, $C(=O)R^6$, $C(=O)OR^7$, $C(=NR^8)R^6$, $C(=S)NR^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$,
where $R^6$, $R^7$, $R^8$, $R^9$, $R^{10}$, $R^{13}$ and $R^{14}$ have one of the general or in particular one of the preferred meanings given above.

More preferably, in compounds I-1,
$R^{5a}$, $R^{5b}$ and $R^{5c}$ are, independently of each other, selected from the group consisting of hydrogen, halogen, cyano, $C_1$-$C_4$-alkyl, $C_3$-$C_8$-cycloalkyl, $C_3$-$C_8$-halocycloalkyl, $C_1$-$C_4$-alkoxy and $C_1$-$C_4$-haloalkoxy.

Preferred compounds I-1 are compounds of the formula I-1.1 wherein
$B^3$ is $CR^{5c}$ or N;
Y, $R^1$, $R^2$ and $A^2$ have one of the general or in particular one of the preferred meanings given above $R^{5a}$, $R^{5b}$ and $R^{5c}$ have one of the general or in particular one of the preferred meanings given above; and $R^{4a}$ is selected from the group consisting of hydrogen, halogen, cyano, nitro, —SCN, $C_1$-$C_6$-alkyl which may be partially or fully halogenated and/or may be substituted by one or more, e.g. 1, 2, 3 or 4, preferably 1 or 2, more preferably 1, radicals $R^6$, $C_3$-$C_8$-cycloalkyl which may be partially or fully halogenated and/or may be substituted by one or more, e.g. 1, 2, 3 or 4, preferably 1 or 2, more preferably 1, radicals $R^6$, $-OR^7$, $-OS(O)_nR^7$, $-SR^7$, $-S(O)_mR^7$, $-S(O)_nN(R^8)R^9$, $-N(R^8)R^9$, $-N(R^8)C(=O)R^6$, $C(=O)R^6$, $-C(=O)OR^7$, $-C(=NR^8)R^6$, $-C(=O)N(R^8)R^9$, $-C(=S)N(R^8)R^9$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, preferably from hydrogen, halogen; cyano; nitro; —SCN; $C_1$-$C_6$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $-OR^7$; $-OS(O)_nR^7$; $-SR^7$; $-S(O)_mR^7$; $-S(O)_nN(R^8)R^9$; $-N(R^8)R^9$; $C(=O)R^6$; $-C(=O)OR^7$; $-C(=NR^8)R^6$; $-C(=O)N(R^8)R^9$; $-C(=S)N(R^8)R^9$ and phenyl which may be substituted by 1, 2, 3, 4 or 5 radicals $R^{10}$, more preferably from hydrogen, halogen; cyano; nitro; $C_1$-$C_6$-alkyl; $C_1$-$C_6$-haloalkyl; $C_1$-$C_6$-alkoxy; $C_1$-$C_6$-haloalkoxy; and phenyl which may be substituted by 1, 2, 3, 4 or 5 radicals $R^{10}$, even more preferably from hydrogen, halogen, cyano, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy, in particular from hydrogen and $C_1$-$C_6$-alkyl, preferably $C_1$-$C_4$-alkyl, and is specifically methyl, where $R^6$, $R^7$, $R^8$, $R^9$ and $R^{10}$ have one of the general or in particular one of the preferred meanings given above.

Preferably, in compounds I-1.1,
$R^{5a}$, $R^{5c}$ are, independently of each other, selected from the group consisting of hydrogen, halogen, cyano, nitro, SCN, SF$_5$, C$_1$-C$_6$-alkyl which may be partially or fully halogenated and/or may be substituted by one or more, e.g. 1, 2, 3 or 4, preferably 1 or 2, more preferably 1, radicals R$^6$, C$_3$-C$_8$-cycloalkyl which may be partially or fully halogenated and/or may be substituted by one or more, e.g. 1, 2, 3 or 4, preferably 1 or 2, more preferably 1, radicals R$^6$, OR$^7$, SR$^7$, S(O)$_m$R$^7$, NR$^8$R$^9$, C(=O)R$^6$, —C(=O)OR$^7$, C(=NR$^8$)R$^6$, C(=S)NR$^6$; and R$^{5b}$ is selected from the group consisting of hydrogen, halogen, cyano, nitro, —SCN, SF$_5$, C$_1$-C$_6$-alkyl which may be partially or fully halogenated and/or may be substituted by one or more, e.g. 1, 2, 3 or 4, preferably 1 or 2, more preferably 1, radicals R$^6$, C$_3$-C$_8$-cycloalkyl which may be partially or fully halogenated and/or may be substituted by one or more, e.g. 1, 2, 3 or 4, preferably 1 or 2, more preferably 1, radicals R$^6$, C$_2$-C$_6$-alkenyl which may be partially or fully halogenated and/or may be substituted by one or more, e.g. 1, 2, 3 or 4, preferably 1 or 2, more preferably 1, radicals R$^6$, C$_2$-C$_6$-alkynyl which may be partially or fully halogenated and/or may be substituted by one or more, e.g. 1, 2, 3 or 4, preferably 1 or 2, more preferably 1, radicals R$^6$, Si(R$^{14}$)$_2$R$^{13}$, OR$^7$, SR$^7$, OS(O)$_n$R$^7$, S(O)$_m$R$^7$, NR$^8$R$^9$, N(R$^8$)C(=O)R$^6$, C(=O)R$^6$, C(=O)OR$^7$, C(=NR$^8$)R$^6$, C(=S)NR$^6$, phenyl which may be substituted by 1, 2, 3, 4 or 5 radicals R$^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, preferably 1 or 2, more preferably 1, radicals R$^{10}$, where R$^6$, R$^7$, R$^8$, R$^9$, R$^{10}$, R$^{13}$ and R$^{14}$ have one of the general or in particular one of the preferred meanings given above.

More preferably, in compounds I-1.1,
R$^{5a}$, R$^{5b}$ and R$^{5c}$ are, independently of each other, selected from the group consisting of hydrogen, halogen, cyano, C$_1$-C$_4$-alkyl, C$_1$-C$_4$-haloalkyl, C$_3$-C$_8$-cycloalkyl, C$_3$-C$_8$-halocycloalkyl, C$_1$-C$_4$-alkoxy and C$_1$-C$_4$-haloalkoxy, even more preferably from hydrogen, halogen, C$_1$-C$_4$-alkyl and C$_1$-C$_4$-haloalkyl, in particular from hydrogen, halogen, and C$_1$-C$_3$-haloalkyl, and, specifically hydrogen, chlorine and CF$_3$.

Preferred compounds I-1.1 are compounds of the formula I-1.1.1

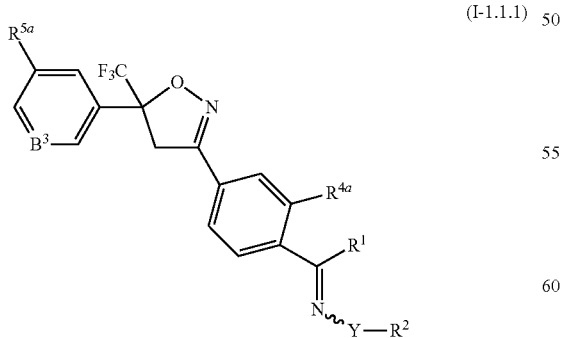

(I-1.1.1)

wherein
B$^3$ is CR$^{5c}$ or N;
Y, R$^1$ and R$^2$ have one of the general or in particular one of the preferred meanings given above;

R$^{5a}$ and R$^{5c}$ have one of the general or in particular one of the preferred meanings given above; and
R$^{4a}$ is selected from the group consisting of hydrogen, halogen, cyano, nitro, —SCN, C$_1$-C$_6$-alkyl which may be partially or fully halogenated and/or may be substituted by one or more, e.g. 1, 2, 3 or 4, preferably 1 or 2, more preferably 1, radicals R$^6$, C$_3$-C$_8$-cycloalkyl which may be partially or fully halogenated and/or may be substituted by one or more, e.g. 1, 2, 3 or 4, preferably 1 or 2, more preferably 1, radicals R$^6$, —OR$^7$, —OS(O)$_n$R$^7$, —SR$^7$, S(O)$_m$R$^7$, —S(O)$_n$N(R$^8$)R$^9$, —N(R$^8$)R$^9$, —N(R$^8$)C(=O)R$^6$, C(=O)R$^6$, —C(=O)OR$^7$, —C(=NR$^8$)R$^6$, —C(=O)N(R$^8$)R$^9$, —C(=S)N(R$^8$)R$^9$, phenyl which may be substituted by 1, 2, 3, 4 or 5 radicals R$^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, preferably 1 or 2, more preferably 1, radicals R$^{10}$, preferably from hydrogen, halogen; cyano; nitro; —SCN; C$_1$-C$_6$-alkyl which may be partially or fully halogenated and/or may be substituted by one or more, e.g. 1, 2, 3 or 4, preferably 1 or 2, more preferably 1, radicals R$^6$; C$_3$-C$_8$-cycloalkyl which may be partially or fully halogenated and/or may be substituted by one or more, e.g. 1, 2, 3 or 4, preferably 1 or 2, more preferably 1, radicals R$^6$; —OR$^7$; —OS(O)$_n$R$^7$; —SR$^7$; —S(O)$_m$R$^7$, —S(O)$_n$N(R$^8$)R$^9$; —N(R$^8$)R$^9$; C(=O)R$^6$; —C(=O)OR$^7$; —C(=NR$^8$)R$^6$; —C(=O)N(R$^8$)R$^9$; —C(=S)N(R$^8$)R$^9$ and phenyl which may be substituted by 1, 2, 3, 4 or 5 radicals R$^{10}$, more preferably from hydrogen, halogen; cyano; nitro; C$_1$-C$_6$-alkyl; C$_1$-C$_6$-haloalkyl; C$_1$-C$_6$-alkoxy; C$_1$-C$_6$-haloalkoxy; and phenyl which may be substituted by 1, 2, 3, 4 or 5 radicals R$^{10}$, even more preferably from hydrogen, halogen, cyano, C$_1$-C$_4$-alkyl, C$_1$-C$_4$-haloalkyl, C$_3$-C$_8$-cycloalkyl, C$_3$-C$_8$-halocycloalkyl, C$_1$-C$_4$-alkoxy and C$_1$-C$_4$-haloalkoxy, in particular from hydrogen and C$_1$-C$_6$-alkyl, preferably C$_1$-C$_4$-alkyl, and is specifically methyl, where R$^6$, R$^7$, R$^8$, R$^9$ and R$^{10}$ have one of the general or in particular one of the preferred meanings given above.

Preferably, in compounds I-1.1.1,
R$^{5a}$ and R$^{5c}$ are, independently of each other, selected from the group consisting of hydrogen, halogen, cyano, nitro, SCN, SF$_5$, C$_1$-C$_6$-alkyl which may be partially or fully halogenated and/or may be substituted by one or more, e.g. 1, 2, 3 or 4, preferably 1 or 2, more preferably 1, radicals R$^6$, C$_3$-C$_8$-cycloalkyl which may be partially or fully halogenated and/or may be substituted by one or more, e.g. 1, 2, 3 or 4, preferably 1 or 2, more preferably 1, radicals R$^6$, OR$^7$, SR$^7$, S(O)$_m$R$^7$, NR$^8$R$^9$, C(=O)R$^6$, —C(=O)OR$^7$, C(=NR$^8$)R$^6$, C(=S)NR$^6$; and
where R$^6$, R$^7$, R$^8$ and R$^9$ have one of the general or in particular one of the preferred meanings given above.

More preferably, in compounds I-1.1.1,
R$^{5a}$ and R$^{5c}$ are, independently of each other, selected from the group consisting of hydrogen, halogen, cyano, C$_1$-C$_4$-alkyl, C$_1$-C$_4$-haloalkyl, C$_3$-C$_8$-cycloalkyl, C$_3$-C$_8$-halocycloalkyl, C$_1$-C$_4$-alkoxy and C$_1$-C$_4$-haloalkoxy, even more preferably from hydrogen, halogen, C$_1$-C$_4$-alkyl and C$_1$-C$_4$-haloalkyl, in particular from hydrogen, halogen, and C$_1$-C$_3$-haloalkyl, and more particularly from halogen and C$_1$-C$_2$-haloalkyl and, specifically chlorine and CF$_3$.

Specifically, in compounds I-1, I-1.1 and I-1.1.1, $A^2$ is N or (in compounds I-1 and I-1.1) preferably CH;

$R^1$ is selected from the group consisting of hydrogen; cyano, $C_1$-$C_4$-alkyl, $C_1$-$C_4$-haloalkyl, specifically $C_1$-$C_4$-fluoroalkyl, $C_1$-$C_4$-alkyl which is substituted by one radical $R^6$; where $R^6$ has one of the meanings given above or preferably one of the preferred meanings given above, $C_1$-$C_4$-oxy $C_1$-$C_4$-haloalkoxy, $C_1$-$C_4$-alkylcarbonyl, and $C_1$-$C_4$-haloalkylcarbonyl;

Y is O or $NR^3$;

$R^2$ is selected from hydrogen; $C_1$-$C_4$-alkyl; $C_1$-$C_4$-haloalkyl; a methyl group substituted by a radical $R^{6a}$ selected from CN, phenyl which may carry 1, 2 or 3 substituents $R^{10a}$, —C(=O)$R^{6b}$; —C(=O)N($R^{8a}$)$R^{9a}$ and —C(=O)O$R^{7a}$; —C(=O)$R^{6c}$; —C(=O)N($R^{8a}$)$R^{9a}$; and —C(=N$R^{8a}$)$R^{6d}$, where $R^{6b}$ and $R^{6c}$ are independently selected from $C_1$-$C_4$-alkyl, $C_1$-$C_4$-haloalkyl, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkoxy and $C_1$-$C_4$-haloalkoxy;

$R^{6d}$ is selected from N($R^{8a}$)$R^{9a}$;

$R^{7a}$ is selected from hydrogen, $C_1$-$C_4$-alkyl, $C_1$-$C_4$-haloalkyl, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy;

each $R^{8a}$ is independently selected from hydrogen, $C_1$-$C_4$-alkyl, $C_1$-$C_4$-haloalkyl, phenyl and benzyl;

each $R^{9a}$ is independently selected from hydrogen, $C_1$-$C_4$-alkyl, $C_1$-$C_4$-haloalkyl, $C_3$-$C_6$-cycloalkyl, $C_3$-$C_6$-halocycloalkyl, $C_3$-$C_6$-cycloalkyl-$C_1$-$C_4$-alkyl, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy; and $R^{10a}$ is selected from halogen, CN, $C_1$-$C_4$-alkyl, $C_1$-$C_4$-haloalkyl, $C_1$-$C_4$-alkoxy and $C_1$-$C_4$-haloalkoxy;

$R^3$ is selected from the group consisting of hydrogen, $C_1$-$C_4$-alkyl, $C_1$-$C_4$-haloalkyl, and —C(=O)$R^6$, where $R^6$ has one of the meanings given above or in particular one of the preferred meanings given above and is specifically $C_1$-$C_4$-alkyl;

$R^{4(a)}$ is selected from the group consisting of hydrogen, halogen, cyano, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy, in particular from hydrogen, halogen, cyano and $C_1$-$C_4$-alkyl, and is specifically halogen, cyano or methyl;

p in formula I-1 is 0 or 1, preferably 1;

$R^{5a}$, $R^{5b}$ and $R^{5c}$ are, independently of each other, selected from the group consisting of hydrogen, halogen, cyano, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy, even more preferably from hydrogen, halogen, $C_1$-$C_4$-alkyl and $C_1$-$C_4$-haloalkyl, in particular from hydrogen, halogen, and $C_1$-$C_3$-haloalkyl, and specifically hydrogen, chlorine and $CF_3$; and X in formula I-1 is $C_1$-$C_2$-haloalkyl and preferably halomethyl, specifically $CF_3$.

Examples of preferred compounds are compounds of the following formulae I-a to I-z, I-aa to I-zz and I-α to I-β, where the variables have one of the general or preferred meanings given above. Examples of preferred compounds which are represented by the formulae Ia, Ib and Ic are the individual compounds compiled in the tables 1 to 53850 below, where the variables Y and $R^2$ have the meanings given in one row of table A. Moreover, the meanings mentioned for the individual variables in the tables are per se, independently of the combination in which they are mentioned, a particularly preferred embodiment of the substituents in question.

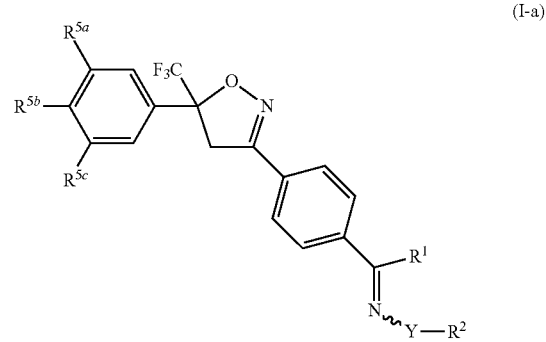

(I-a)

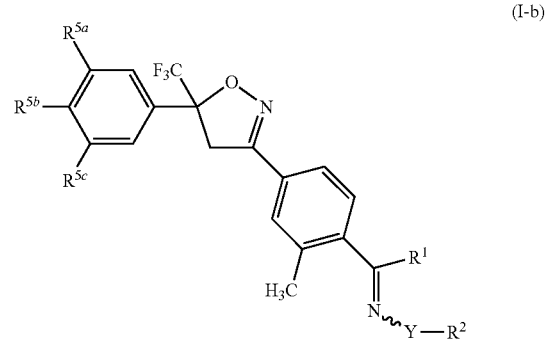

(I-b)

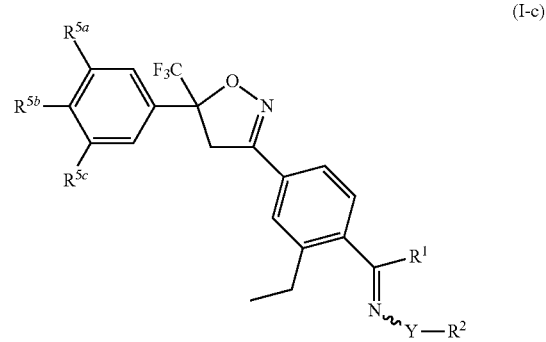

(I-c)

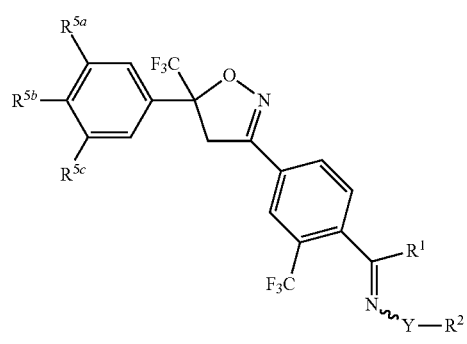 (I-d)
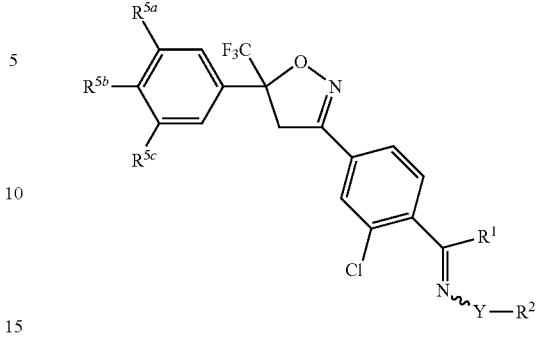 (I-h)
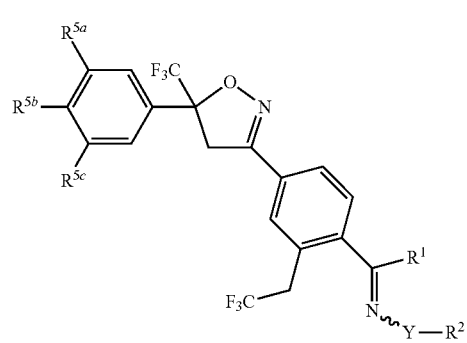 (I-e)
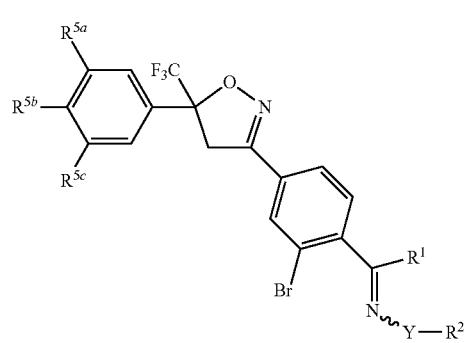 (I-i)
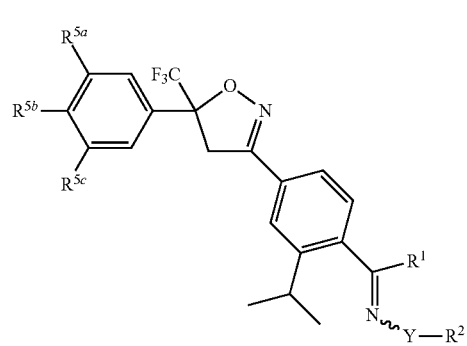 (I-f)
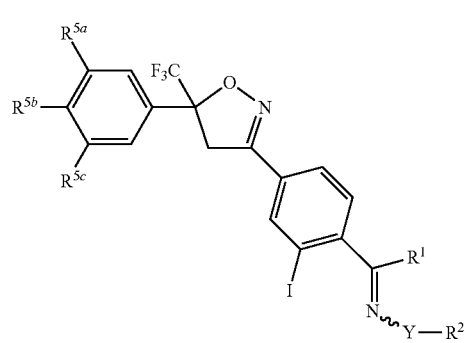 (I-j)
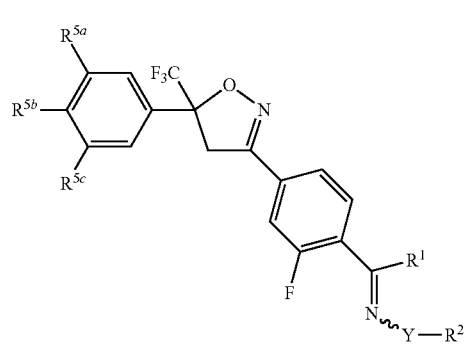 (I-g)
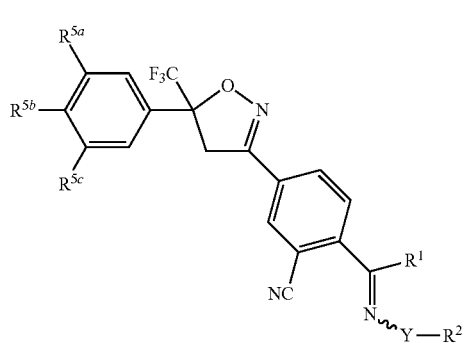 (I-k)

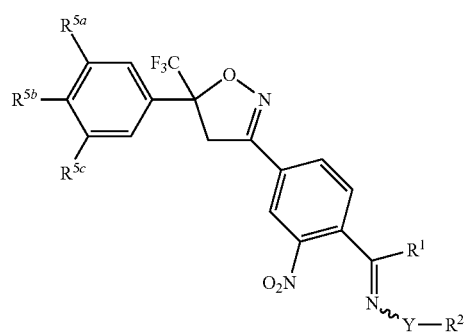
(I-l)
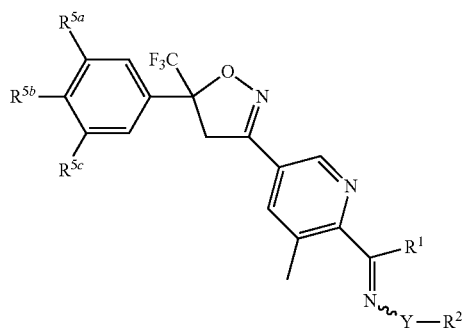
(I-p)
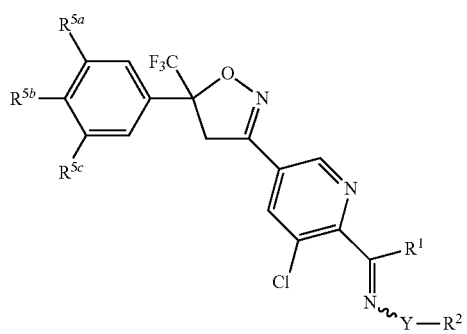
(I-m)
(I-q)
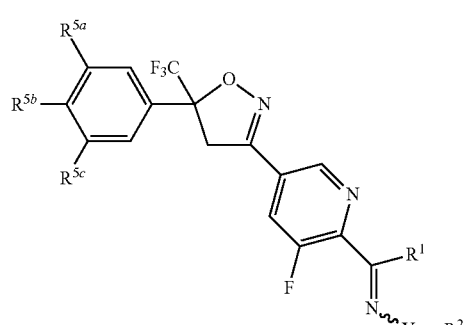
(I-n)
(I-r)
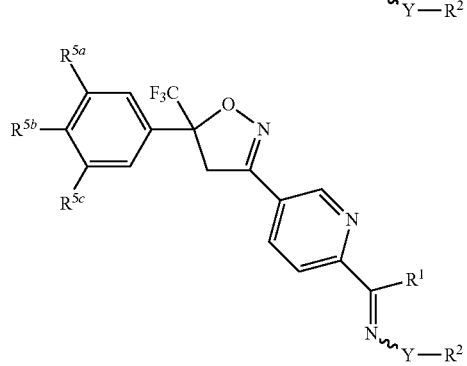
(I-o)
(I-s)
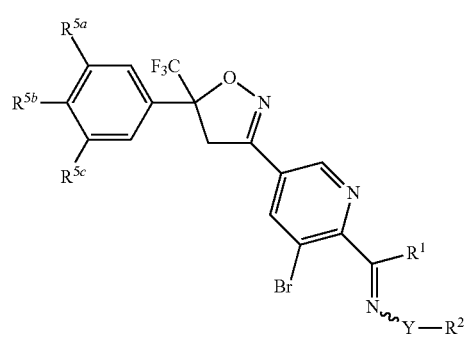
(I-t)

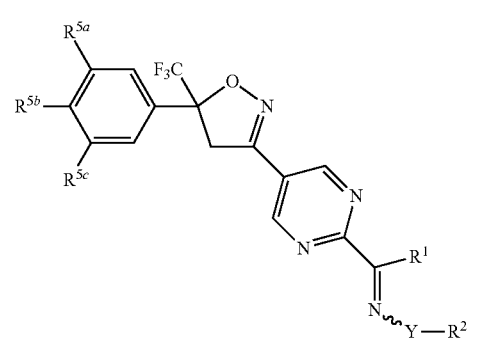
(I-u)
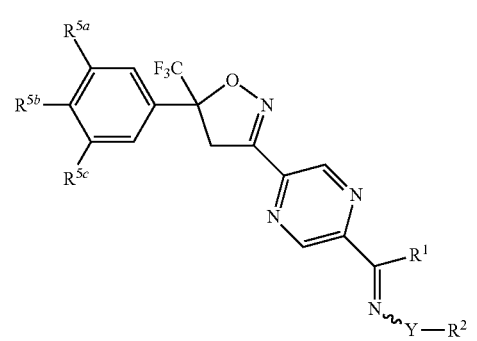
(I-v)
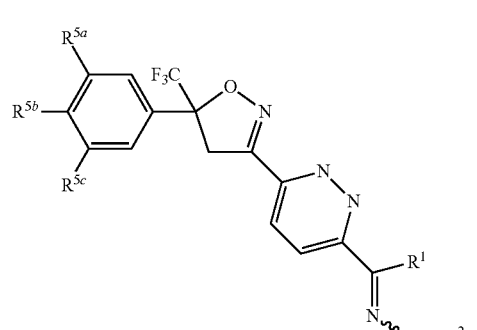
(I-w)
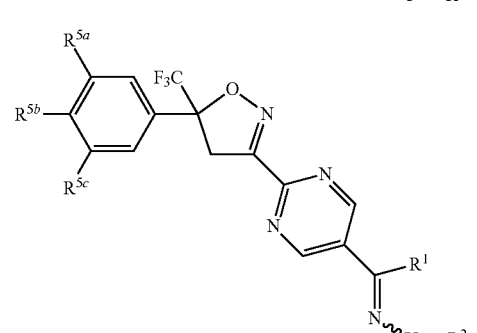
(I-x)
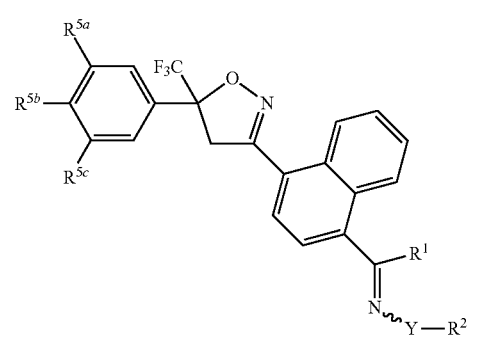
(I-y)
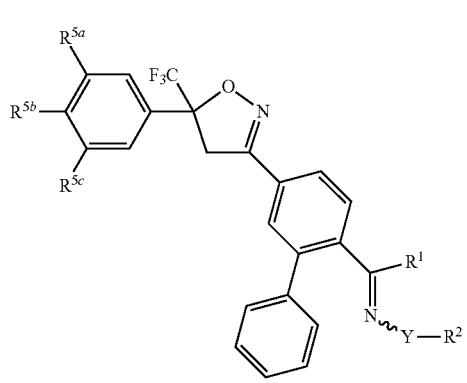
(I-z)
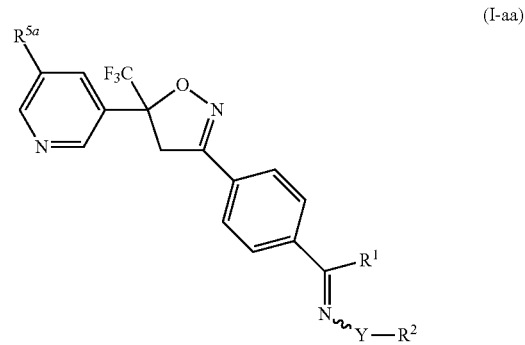
(I-aa)
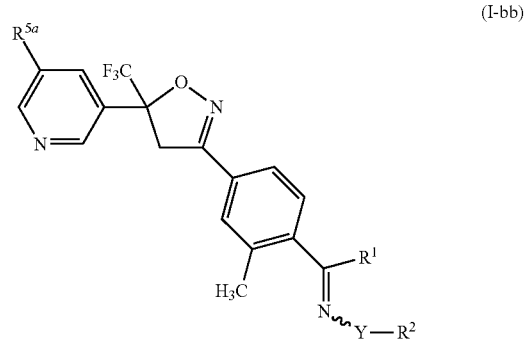
(I-bb)
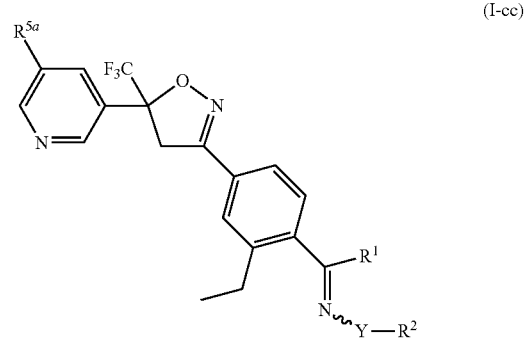
(I-cc)

-continued
(I-dd)
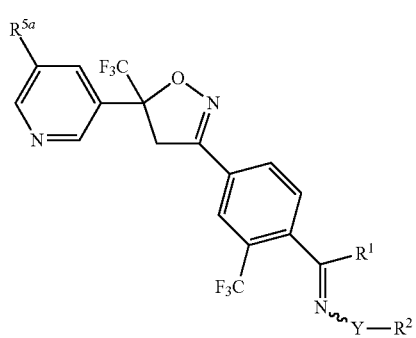
(I-ee)
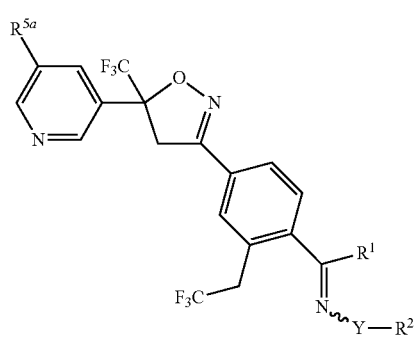
(I-ff)
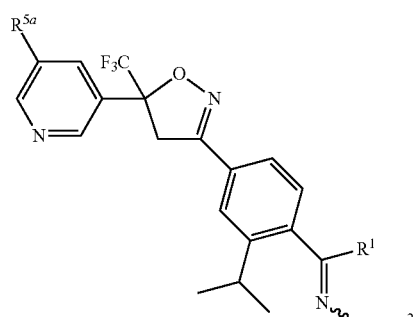
(I-gg)
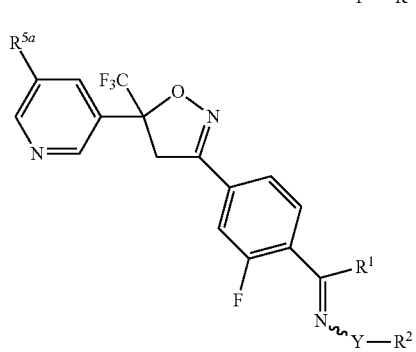
(I-hh)
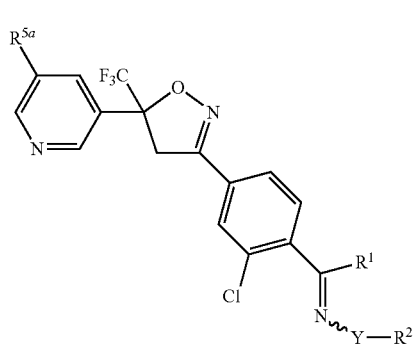
-continued
(I-ii)
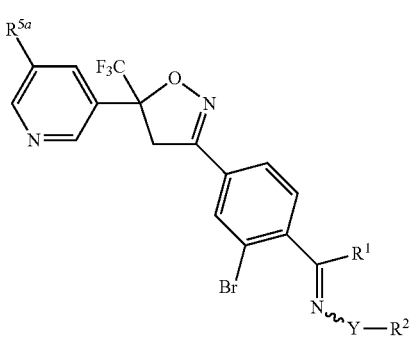
(I-jj)
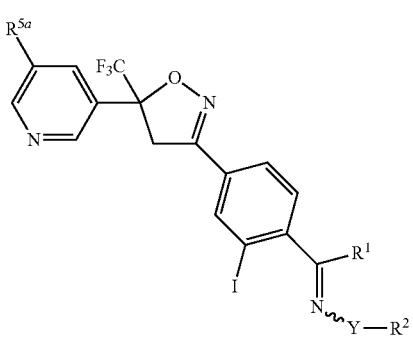
(I-kk)
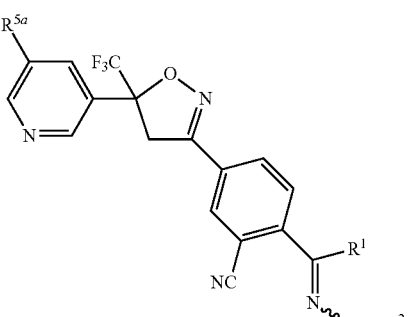
(I-ll)
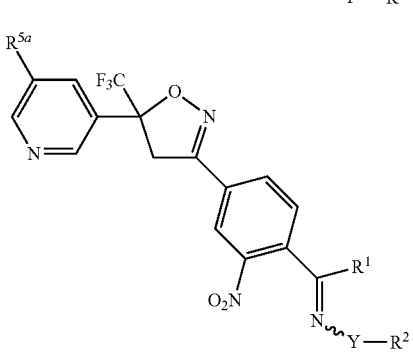
(I-mm)
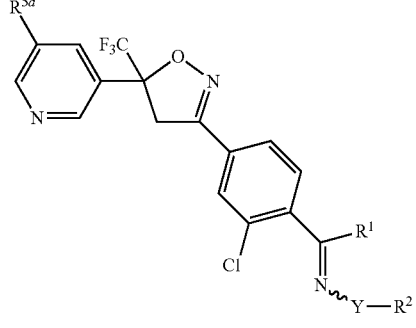

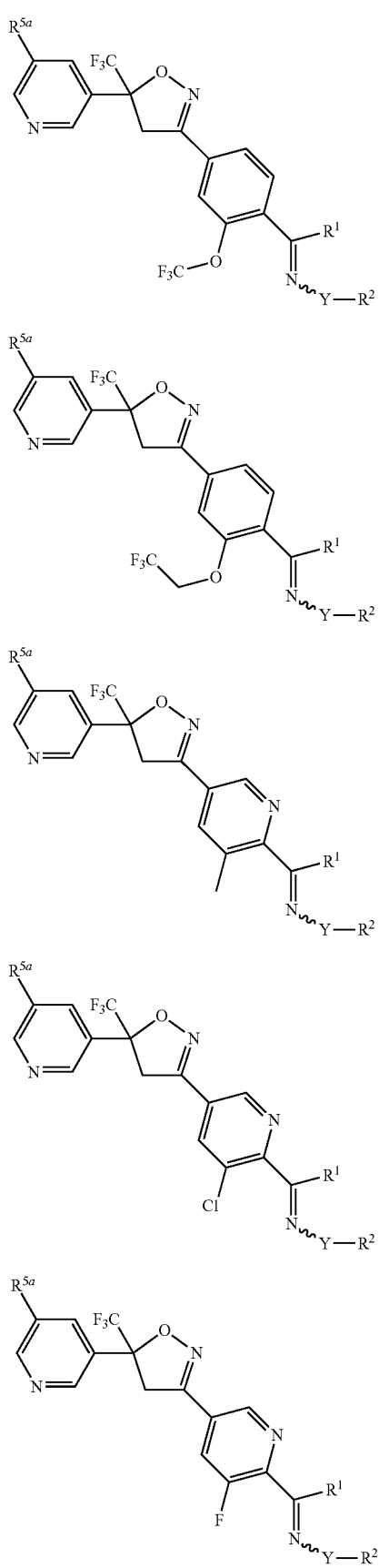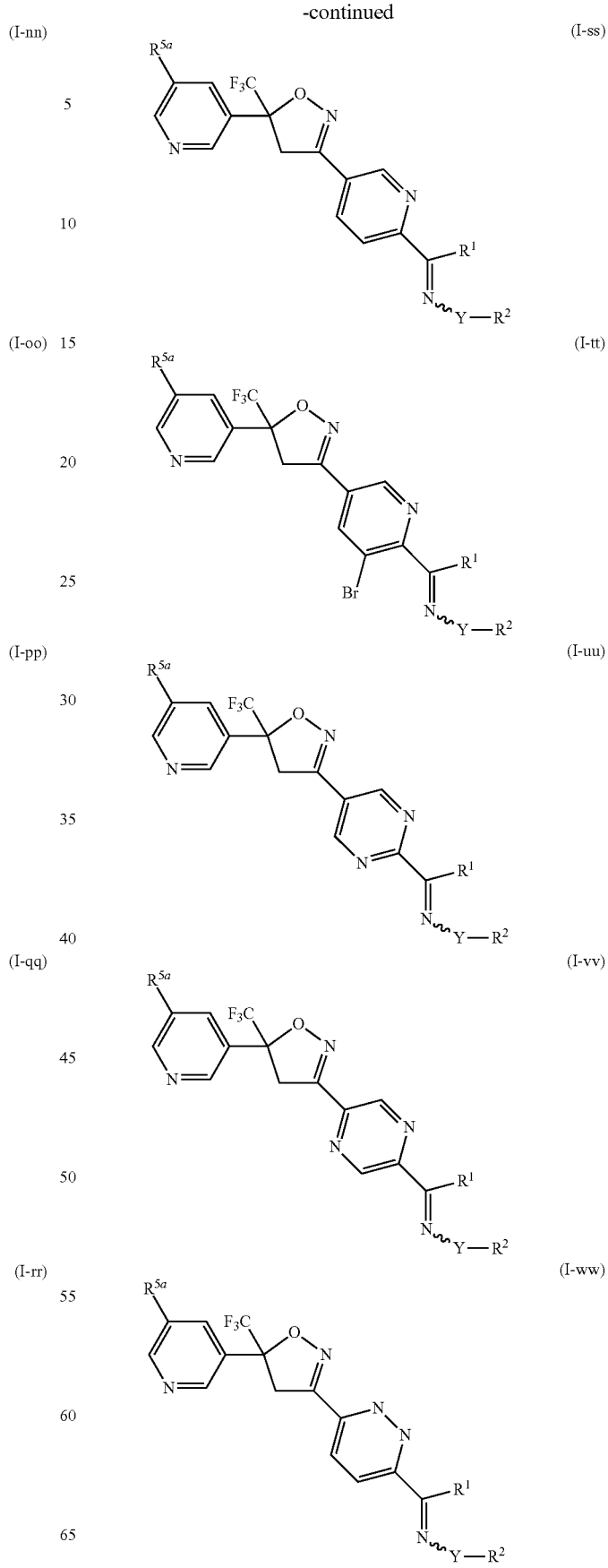

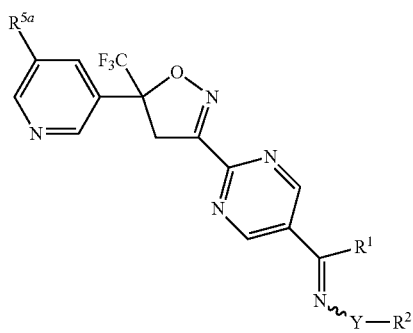
(I-xx)

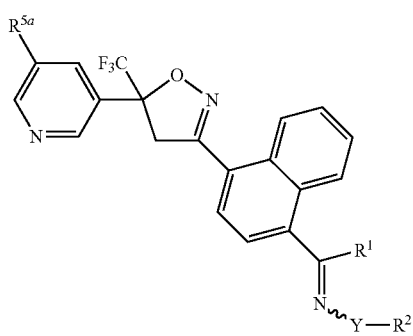
(I-yy)

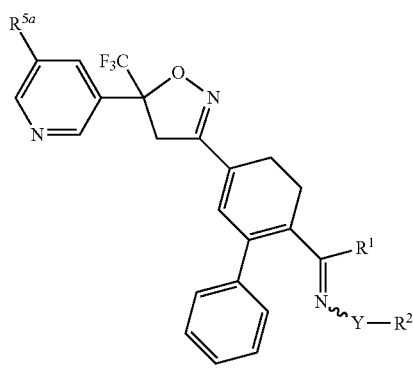
(I-zz)

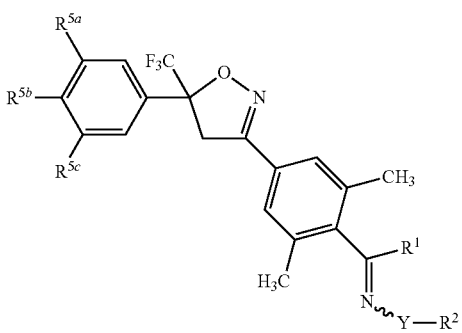
(I-α)

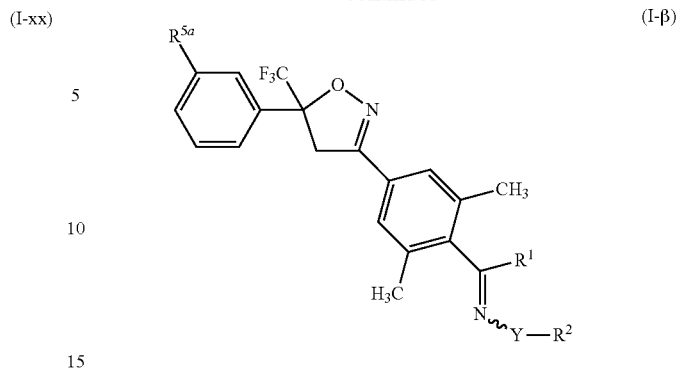
(I-β)

Table 1
Compounds of the formula I-a in which $R^{5a}$ and $R^{5c}$ are chlorine, $R^{5b}$ is H, $R^1$ is H and the combination of Y and $R^2$ for a compound corresponds in each case to one row of Table A.

Table 2
Compounds of the formula I-a in which $R^{5a}$ and $R^{5c}$ are bromine, $R^{5b}$ is H, $R^1$ is H and the combination of Y and $R^2$ for a compound corresponds in each case to one row of Table A.

Table 3
Compounds of the formula I-a in which $R^{5a}$ and $R^{5c}$ are fluorine, $R^{5b}$ is H, $R^1$ is H and the combination of Y and $R^2$ for a compound corresponds in each case to one row of Table A.

Table 4
Compounds of the formula I-a in which $R^{5a}$ and $R^{5c}$ are methyl, $R^{5b}$ is H, $R^1$ is H and the combination of Y and $R^2$ for a compound corresponds in each case to one row of Table A.

Table 5
Compounds of the formula I-a in which $R^{5a}$ and $R^{5c}$ are $CF_3$, $R^{5b}$ is H, $R^1$ is H and the combination of Y and $R^2$ for a compound corresponds in each case to one row of Table A.

Table 6
Compounds of the formula I-a in which $R^{5a}$ is chlorine and $R^{5b}$ and $R^{5c}$ are H, $R^1$ is H and the combination of Y and $R^2$ for a compound corresponds in each case to one row of Table A.

Table 7
Compounds of the formula I-a in which $R^{5a}$ is $CF_3$ and $R^{5b}$ and $R^{5c}$ are H, $R^1$ is H and the combination of Y and $R^2$ for a compound corresponds in each case to one row of Table A.

Table 8
Compounds of the formula I-a in which $R^{5a}$, $R^{5b}$ and $R^{5c}$ are chlorine, $R^1$ is H and the combination of Y and $R^2$ for a compound corresponds in each case to one row of Table A.

Table 9
Compounds of the formula I-a in which $R^{5a}$, $R^{5b}$ and $R^{5c}$ are fluorine, $R^1$ is H and the combination of Y and $R^2$ for a compound corresponds in each case to one row of Table A.

Table 10
Compounds of the formula I-a in which $R^{5a}$, $R^{5b}$ and $R^{5c}$ are methyl, $R^1$ is H and the combination of Y and $R^2$ for a compound corresponds in each case to one row of Table A.

Table 11
Compounds of the formula I-b in which $R^{5a}$ and $R^{5c}$ are chlorine, $R^{5b}$ is H, $R^1$ is H and the combination of Y and $R^2$ for a compound corresponds in each case to one row of Table A.

Table 12
Compounds of the formula I-b in which $R^{5a}$ and $R^{5c}$ are bromine, $R^{5b}$ is H, $R^1$ is H and the combination of Y and $R^2$ for a compound corresponds in each case to one row of Table A.

Table 13
Compounds of the formula I-b in which $R^{5a}$ and $R^{5c}$ are fluorine, $R^{5b}$ is H, $R^1$ is H and the combination of Y and $R^2$ for a compound corresponds in each case to one row of Table A.

Table 14

Compounds of the formula I-b in which $R^{5a}$ and $R^{5c}$ are methyl, $R^{5b}$ is H, $R^1$ is H and the combination of Y and $R^2$ for a compound corresponds in each case to one row of Table A.

Table 15

Compounds of the formula I-b in which $R^{5a}$ and $R^{5c}$ are $CF_3$, $R^{5b}$ is H, $R^1$ is H and the combination of Y and $R^2$ for a compound corresponds in each case to one row of Table A.

Table 16

Compounds of the formula I-b in which $R^{5a}$ is chlorine and $R^{5b}$ and $R^{5c}$ are H, $R^1$ is H and the combination of Y and $R^2$ for a compound corresponds in each case to one row of Table A.

Table 17

Compounds of the formula I-b in which $R^{5a}$ is $CF_3$ and $R^{5b}$ and $R^{5c}$ are H, $R^1$ is H and the combination of Y and $R^2$ for a compound corresponds in each case to one row of Table A.

Table 18

Compounds of the formula I-b in which $R^{5a}$, $R^{5b}$ and $R^{5c}$ are chlorine, $R^1$ is H and the combination of Y and $R^2$ for a compound corresponds in each case to one row of Table A.

Table 19

Compounds of the formula I-b in which $R^{5a}$, $R^{5b}$ and $R^{5c}$ are fluorine, $R^1$ is H and the combination of Y and $R^2$ for a compound corresponds in each case to one row of Table A.

Table 20

Compounds of the formula I-b in which $R^{5a}$, $R^{5b}$ and $R^{5c}$ are methyl, $R^1$ is H and the combination of Y and $R^2$ for a compound corresponds in each case to one row of Table A.

Table 21

Compounds of the formula I-c in which $R^{5a}$ and $R^{5c}$ are chlorine, $R^{5b}$ is H, $R^1$ is H and the combination of Y and $R^2$ for a compound corresponds in each case to one row of Table A.

Table 22

Compounds of the formula I-c in which $R^{5a}$ and $R^{5c}$ are bromine, $R^{5b}$ is H, $R^1$ is H and the combination of Y and $R^2$ for a compound corresponds in each case to one row of Table A.

Table 23

Compounds of the formula I-c in which $R^{5a}$ and $R^{5c}$ are fluorine, $R^{5b}$ is H, $R^1$ is H and the combination of Y and $R^2$ for a compound corresponds in each case to one row of Table A.

Table 24

Compounds of the formula I-c in which $R^{5a}$ and $R^{5c}$ are methyl, $R^{5b}$ is H, $R^1$ is H and the combination of Y and $R^2$ for a compound corresponds in each case to one row of Table A.

Table 25

Compounds of the formula I-c in which $R^{5a}$ and $R^{5c}$ are $CF_3$, $R^{5b}$ is H, $R^1$ is H and the combination of Y and $R^2$ for a compound corresponds in each case to one row of Table A.

Table 26

Compounds of the formula I-c in which $R^{5a}$ is chlorine and $R^{5b}$ and $R^{5c}$ are H, $R^1$ is H and the combination of Y and $R^2$ for a compound corresponds in each case to one row of Table A.

Table 27

Compounds of the formula I-c in which $R^{5a}$ is $CF_3$ and $R^{5b}$ and $R^{5c}$ are H, $R^1$ is H and the combination of Y and $R^2$ for a compound corresponds in each case to one row of Table A.

Table 28

Compounds of the formula I-c in which $R^{5a}$, $R^{5b}$ and $R^{5c}$ are chlorine, $R^1$ is H and the combination of Y and $R^2$ for a compound corresponds in each case to one row of Table A.

Table 29

Compounds of the formula I-c in which $R^{5a}$, $R^{5b}$ and $R^{5c}$ are fluorine, $R^1$ is H and the combination of Y and $R^2$ for a compound corresponds in each case to one row of Table A.

Table 30

Compounds of the formula I-c in which $R^{5a}$, $R^{5b}$ and $R^{5c}$ are methyl, $R^1$ is H and the combination of Y and $R^2$ for a compound corresponds in each case to one row of Table A.

Table 31

Compounds of the formula I-d in which $R^{5a}$ and $R^{5c}$ are chlorine, $R^{5b}$ is H, $R^1$ is H and the combination of Y and $R^2$ for a compound corresponds in each case to one row of Table A.

Table 32

Compounds of the formula I-d in which $R^{5a}$ and $R^{5c}$ are bromine, $R^{5b}$ is H, $R^1$ is H and the combination of Y and $R^2$ for a compound corresponds in each case to one row of Table A.

Table 33

Compounds of the formula I-d in which $R^{5a}$ and $R^{5c}$ are fluorine, $R^{5b}$ is H, $R^1$ is H and the combination of Y and $R^2$ for a compound corresponds in each case to one row of Table A.

Table 34

Compounds of the formula I-d in which $R^{5a}$ and $R^{5c}$ are methyl, $R^{5b}$ is H, $R^1$ is H and the combination of Y and $R^2$ for a compound corresponds in each case to one row of Table A.

Table 35

Compounds of the formula I-d in which $R^{5a}$ and $R^{5c}$ are $CF_3$, $R^{5b}$ is H, $R^1$ is H and the combination of Y and $R^2$ for a compound corresponds in each case to one row of Table A.

Table 36

Compounds of the formula I-d in which $R^{5a}$ is chlorine and $R^{5b}$ and $R^{5c}$ are H, $R^1$ is H and the combination of Y and $R^2$ for a compound corresponds in each case to one row of Table A.

Table 37

Compounds of the formula I-d in which $R^{5a}$ is $CF_3$ and $R^{5b}$ and $R^{5c}$ are H, $R^1$ is H and the combination of Y and $R^2$ for a compound corresponds in each case to one row of Table A.

Table 38

Compounds of the formula I-d in which $R^{5a}$, $R^{5b}$ and $R^{5c}$ are chlorine, $R^1$ is H and the combination of Y and $R^2$ for a compound corresponds in each case to one row of Table A.

Table 39

Compounds of the formula I-d in which $R^{5a}$, $R^{5b}$ and $R^{5c}$ are fluorine, $R^1$ is H and the combination of Y and $R^2$ for a compound corresponds in each case to one row of Table A.

Table 40

Compounds of the formula I-d in which $R^{5a}$, $R^{5b}$ and $R^{5c}$ are methyl, $R^1$ is H and the combination of Y and $R^2$ for a compound corresponds in each case to one row of Table A.

Table 41

Compounds of the formula I-e in which $R^{5a}$ and $R^{5c}$ are chlorine, $R^{5b}$ is H, $R^1$ is H and the combination of Y and $R^2$ for a compound corresponds in each case to one row of Table A.

Table 42

Compounds of the formula I-e in which $R^{5a}$ and $R^{5c}$ are bromine, $R^{5b}$ is H, $R^1$ is H and the combination of Y and $R^2$ for a compound corresponds in each case to one row of Table A.

Table 43

Compounds of the formula I-e in which $R^{5a}$ and $R^{5c}$ are fluorine, $R^{5b}$ is H, $R^1$ is H and the combination of Y and $R^2$ for a compound corresponds in each case to one row of Table A.

Table 44

Compounds of the formula I-e in which $R^{5a}$ and $R^{5c}$ are methyl, $R^{5b}$ is H, $R^1$ is H and the combination of Y and $R^2$ for a compound corresponds in each case to one row of Table A.

Table 45

Compounds of the formula I-e in which $R^{5a}$ and $R^{5c}$ are $CF_3$, $R^{5b}$ is H, $R^1$ is H and the combination of Y and $R^2$ for a compound corresponds in each case to one row of Table A.

Table 46
Compounds of the formula I-e in which $R^{5a}$ is chlorine and $R^{5b}$ and $R^{5c}$ are H, $R^1$ is H and the combination of Y and $R^2$ for a compound corresponds in each case to one row of Table A.

Table 47
Compounds of the formula I-e in which $R^{5a}$ is $CF_3$ and $R^{5b}$ and $R^{5c}$ are H, $R^1$ is H and the combination of Y and $R^2$ for a compound corresponds in each case to one row of Table A.

Table 48
Compounds of the formula I-e in which $R^{5a}$, $R^{5b}$ and $R^{5c}$ are chlorine, $R^1$ is H and the combination of Y and $R^2$ for a compound corresponds in each case to one row of Table A.

Table 49
Compounds of the formula I-e in which $R^{5a}$, $R^{5b}$ and $R^{5c}$ are fluorine, $R^1$ is H and the combination of Y and $R^2$ for a compound corresponds in each case to one row of Table A.

Table 50
Compounds of the formula I-e in which $R^{5a}$, $R^{5b}$ and $R^{5c}$ are methyl, $R^1$ is H and the combination of Y and $R^2$ for a compound corresponds in each case to one row of Table A.

Table 51
Compounds of the formula I-f in which $R^{5a}$ and $R^{5c}$ are chlorine, $R^{5b}$ is H, $R^1$ is H and the combination of Y and $R^2$ for a compound corresponds in each case to one row of Table A.

Table 52
Compounds of the formula I-f in which $R^{5a}$ and $R^{5c}$ are bromine, $R^{5b}$ is H, $R^1$ is H and the combination of Y and $R^2$ for a compound corresponds in each case to one row of Table A.

Table 53
Compounds of the formula I-f in which $R^{5a}$ and $R^{5c}$ are fluorine, $R^{5b}$ is H, $R^1$ is H and the combination of Y and $R^2$ for a compound corresponds in each case to one row of Table A.

Table 54
Compounds of the formula I-f in which $R^{5a}$ and $R^{5c}$ are methyl, $R^{5b}$ is H, $R^1$ is H and the combination of Y and $R^2$ for a compound corresponds in each case to one row of Table A.

Table 55
Compounds of the formula I-f in which $R^{5a}$ and $R^{5c}$ are $CF_3$, $R^{5b}$ is H, $R^1$ is H and the combination of Y and $R^2$ for a compound corresponds in each case to one row of Table A.

Table 56
Compounds of the formula I-f in which $R^{5a}$ is chlorine and $R^{5b}$ and $R^{5c}$ are H, $R^1$ is H and the combination of Y and $R^2$ for a compound corresponds in each case to one row of Table A.

Table 57
Compounds of the formula I-f in which $R^{5a}$ is $CF_3$ and $R^{5b}$ and $R^{5c}$ are H, $R^1$ is H and the combination of Y and $R^2$ for a compound corresponds in each case to one row of Table A.

Table 58
Compounds of the formula I-f in which $R^{5a}$, $R^{5b}$ and $R^{5c}$ are chlorine, $R^1$ is H and the combination of Y and $R^2$ for a compound corresponds in each case to one row of Table A.

Table 59
Compounds of the formula I-f in which $R^{5a}$, $R^{5b}$ and $R^{5c}$ are fluorine, $R^1$ is H and the combination of Y and $R^2$ for a compound corresponds in each case to one row of Table A.

Table 60
Compounds of the formula I-f in which $R^{5a}$, $R^{5b}$ and $R^{5c}$ are methyl, $R^1$ is H and the combination of Y and $R^2$ for a compound corresponds in each case to one row of Table A.

Table 61
Compounds of the formula I-g in which $R^{5a}$ and $R^{5c}$ are chlorine, $R^{5b}$ is H, $R^1$ is H and the combination of Y and $R^2$ for a compound corresponds in each case to one row of Table A.

Table 62
Compounds of the formula I-g in which $R^{5a}$ and $R^{5c}$ are bromine, $R^{5b}$ is H, $R^1$ is H and the combination of Y and $R^2$ for a compound corresponds in each case to one row of Table A.

Table 63
Compounds of the formula I-g in which $R^{5a}$ and $R^{5c}$ are fluorine, $R^{5b}$ is H, $R^1$ is H and the combination of Y and $R^2$ for a compound corresponds in each case to one row of Table A.

Table 64
Compounds of the formula I-g in which $R^{5a}$ and $R^{5c}$ are methyl, $R^{5b}$ is H, $R^1$ is H and the combination of Y and $R^2$ for a compound corresponds in each case to one row of Table A.

Table 65
Compounds of the formula I-g in which $R^{5a}$ and $R^{5c}$ are $CF_3$, $R^{5b}$ is H, $R^1$ is H and the combination of Y and $R^2$ for a compound corresponds in each case to one row of Table A.

Table 66
Compounds of the formula I-g in which $R^{5a}$ is chlorine and $R^{5b}$ and $R^{5c}$ are H, $R^1$ is H and the combination of Y and $R^2$ for a compound corresponds in each case to one row of Table A.

Table 67
Compounds of the formula I-g in which $R^{5a}$ is $CF_3$ and $R^{5b}$ and $R^{5c}$ are H, $R^1$ is H and the combination of Y and $R^2$ for a compound corresponds in each case to one row of Table A.

Table 68
Compounds of the formula I-g in which $R^{5a}$, $R^{5b}$ and $R^{5c}$ are chlorine, $R^1$ is H and the combination of Y and $R^2$ for a compound corresponds in each case to one row of Table A.

Table 69
Compounds of the formula I-g in which $R^{5a}$, $R^{5b}$ and $R^{5c}$ are fluorine, $R^1$ is H and the combination of Y and $R^2$ for a compound corresponds in each case to one row of Table A.

Table 70
Compounds of the formula I-g in which $R^{5a}$, $R^{5b}$ and $R^{5c}$ are methyl, $R^1$ is H and the combination of Y and $R^2$ for a compound corresponds in each case to one row of Table A.

Table 71
Compounds of the formula I-h in which $R^{5a}$ and $R^{5c}$ are chlorine, $R^{5b}$ is H, $R^1$ is H and the combination of Y and $R^2$ for a compound corresponds in each case to one row of Table A.

Table 72
Compounds of the formula I-h in which $R^{5a}$ and $R^{5c}$ are bromine, $R^{5b}$ is H, $R^1$ is H and the combination of Y and $R^2$ for a compound corresponds in each case to one row of Table A.

Table 73
Compounds of the formula I-h in which $R^{5a}$ and $R^{5c}$ are fluorine, $R^{5b}$ is H, $R^1$ is H and the combination of Y and $R^2$ for a compound corresponds in each case to one row of Table A.

Table 74
Compounds of the formula I-h in which $R^{5a}$ and $R^{5c}$ are methyl, $R^{5b}$ is H, $R^1$ is H and the combination of Y and $R^2$ for a compound corresponds in each case to one row of Table A.

Table 75
Compounds of the formula I-h in which $R^{5a}$ and $R^{5c}$ are $CF_3$, $R^{5b}$ is H, $R^1$ is H and the combination of Y and $R^2$ for a compound corresponds in each case to one row of Table A.

Table 76
Compounds of the formula I-h in which $R^{5a}$ is chlorine and $R^{5b}$ and $R^{5c}$ are H, $R^1$ is H and the combination of Y and $R^2$ for a compound corresponds in each case to one row of Table A.

Table 77
Compounds of the formula I-h in which $R^{5a}$ is $CF_3$ and $R^{5b}$ and $R^{5c}$ are H, $R^1$ is H and the combination of Y and $R^2$ for a compound corresponds in each case to one row of Table A.

Table 78
Compounds of the formula I-h in which $R^{5a}$, $R^{5b}$ and $R^{5c}$ are chlorine, $R^1$ is H and the combination of Y and $R^2$ for a compound corresponds in each case to one row of Table A.

Table 79
Compounds of the formula I-h in which $R^{5a}$, $R^{5b}$ and $R^{5c}$ are fluorine, $R^1$ is H and the combination of Y and $R^2$ for a compound corresponds in each case to one row of Table A.

Table 80
Compounds of the formula I-h in which $R^{5a}$, $R^{5b}$ and $R^{5c}$ are methyl, $R^1$ is H and the combination of Y and $R^2$ for a compound corresponds in each case to one row of Table A.

Table 81
Compounds of the formula I-i in which $R^{5a}$ and $R^{5c}$ are chlorine, $R^{5b}$ is H, $R^1$ is H and the combination of Y and $R^2$ for a compound corresponds in each case to one row of Table A.

Table 82
Compounds of the formula I-i in which $R^{5a}$ and $R^{5c}$ are bromine, $R^{5b}$ is H, $R^1$ is H and the combination of Y and $R^2$ for a compound corresponds in each case to one row of Table A.

Table 83
Compounds of the formula I-i in which $R^{5a}$ and $R^{5c}$ are fluorine, $R^{5b}$ is H, $R^1$ is H and the combination of Y and $R^2$ for a compound corresponds in each case to one row of Table A.

Table 84
Compounds of the formula I-i in which $R^{5a}$ and $R^{5c}$ are methyl, $R^{5b}$ is H, $R^1$ is H and the combination of Y and $R^2$ for a compound corresponds in each case to one row of Table A.

Table 85
Compounds of the formula I-i in which $R^{5a}$ and $R^{5c}$ are $CF_3$, $R^{5b}$ is H, $R^1$ is H and the combination of Y and $R^2$ for a compound corresponds in each case to one row of Table A.

Table 86
Compounds of the formula I-i in which $R^{5a}$ is chlorine and $R^{5b}$ and $R^{5c}$ are H, $R^1$ is H and the combination of Y and $R^2$ for a compound corresponds in each case to one row of Table A.

Table 87
Compounds of the formula I-i in which $R^{5a}$ is $CF_3$ and $R^{5b}$ and $R^{5c}$ are H, $R^1$ is H and the combination of Y and $R^2$ for a compound corresponds in each case to one row of Table A.

Table 88
Compounds of the formula I-i in which $R^{5a}$, $R^{5b}$ and $R^{5c}$ are chlorine, $R^1$ is H and the combination of Y and $R^2$ for a compound corresponds in each case to one row of Table A.

Table 89
Compounds of the formula I-i in which $R^{5a}$, $R^{5b}$ and $R^{5c}$ are fluorine, $R^1$ is H and the combination of Y and $R^2$ for a compound corresponds in each case to one row of Table A.

Table 90
Compounds of the formula I-i in which $R^{5a}$, $R^{5b}$ and $R^{5c}$ are methyl, $R^1$ is H and the combination of Y and $R^2$ for a compound corresponds in each case to one row of Table A.

Table 91
Compounds of the formula I-j in which $R^{5a}$ and $R^{5c}$ are chlorine, $R^{5b}$ is H, $R^1$ is H and the combination of Y and $R^2$ for a compound corresponds in each case to one row of Table A.

Table 92
Compounds of the formula I-j in which $R^{5a}$ and $R^{5c}$ are bromine, $R^{5b}$ is H, $R^1$ is H and the combination of Y and $R^2$ for a compound corresponds in each case to one row of Table A.

Table 93
Compounds of the formula I-j in which $R^{5a}$ and $R^{5c}$ are fluorine, $R^{5b}$ is H, $R^1$ is H and the combination of Y and $R^2$ for a compound corresponds in each case to one row of Table A.

Table 94
Compounds of the formula I-j in which $R^{5a}$ and $R^{5c}$ are methyl, $R^{5b}$ is H, $R^1$ is H and the combination of Y and $R^2$ for a compound corresponds in each case to one row of Table A.

Table 95
Compounds of the formula I-j in which $R^{5a}$ and $R^{5c}$ are $CF_3$, $R^{5b}$ is H, $R^1$ is H and the combination of Y and $R^2$ for a compound corresponds in each case to one row of Table A.

Table 96
Compounds of the formula I-j in which $R^{5a}$ is chlorine and $R^{5b}$ and $R^{5c}$ are H, $R^1$ is H and the combination of Y and $R^2$ for a compound corresponds in each case to one row of Table A.

Table 97
Compounds of the formula I-j in which $R^{5a}$ is $CF_3$ and $R^{5b}$ and $R^{5c}$ are H, $R^1$ is H and the combination of Y and $R^2$ for a compound corresponds in each case to one row of Table A.

Table 98
Compounds of the formula I-j in which $R^{5a}$, $R^{5b}$ and $R^{5c}$ are chlorine, $R^1$ is H and the combination of Y and $R^2$ for a compound corresponds in each case to one row of Table A.

Table 99
Compounds of the formula I-j in which $R^{5a}$, $R^{5b}$ and $R^{5c}$ are fluorine, $R^1$ is H and the combination of Y and $R^2$ for a compound corresponds in each case to one row of Table A.

Table 100
Compounds of the formula I-j in which $R^{5a}$, $R^{5b}$ and $R^{5c}$ are methyl, $R^1$ is H and the combination of Y and $R^2$ for a compound corresponds in each case to one row of Table A.

Table 101
Compounds of the formula I-k in which $R^{5a}$ and $R^{5c}$ are chlorine, $R^{5b}$ is H, $R^1$ is H and the combination of Y and $R^2$ for a compound corresponds in each case to one row of Table A.

Table 102
Compounds of the formula I-k in which $R^{5a}$ and $R^{5c}$ are bromine, $R^{5b}$ is H, $R^1$ is H and the combination of Y and $R^2$ for a compound corresponds in each case to one row of Table A.

Table 103
Compounds of the formula I-k in which $R^{5a}$ and $R^{5c}$ are fluorine, $R^{5b}$ is H, $R^1$ is H and the combination of Y and $R^2$ for a compound corresponds in each case to one row of Table A.

Table 104
Compounds of the formula I-k in which $R^{5a}$ and $R^{5c}$ are methyl, $R^{5b}$ is H, $R^1$ is H and the combination of Y and $R^2$ for a compound corresponds in each case to one row of Table A.

Table 105
Compounds of the formula I-k in which $R^{5a}$ and $R^{5c}$ are $CF_3$, $R^{5b}$ is H, $R^1$ is H and the combination of Y and $R^2$ for a compound corresponds in each case to one row of Table A.

Table 106
Compounds of the formula I-k in which $R^{5a}$ is chlorine and $R^{5b}$ and $R^{5c}$ are H, $R^1$ is H and the combination of Y and $R^2$ for a compound corresponds in each case to one row of Table A.

Table 107
Compounds of the formula I-k in which $R^{5a}$ is $CF_3$ and $R^{5b}$ and $R^{5c}$ are H, $R^1$ is H and the combination of Y and $R^2$ for a compound corresponds in each case to one row of Table A.

Table 108
Compounds of the formula I-k in which $R^{5a}$, $R^{5b}$ and $R^{5c}$ are chlorine, $R^1$ is H and the combination of Y and $R^2$ for a compound corresponds in each case to one row of Table A.

Table 109
Compounds of the formula I-k in which $R^{5a}$, $R^{5b}$ and $R^{5c}$ are fluorine, $R^1$ is H and the combination of Y and $R^2$ for a compound corresponds in each case to one row of Table A.

Table 110
Compounds of the formula I-k in which $R^{5a}$, $R^{5b}$ and $R^{5c}$ are methyl, $R^1$ is H and the combination of Y and $R^2$ for a compound corresponds in each case to one row of Table A.

Table 111
Compounds of the formula I-l in which $R^{5a}$ and $R^{5c}$ are chlorine, $R^{5b}$ is H, $R^1$ is H and the combination of Y and $R^2$ for a compound corresponds in each case to one row of Table A.

Table 112
Compounds of the formula I-l in which $R^{5a}$ and $R^{5c}$ are bromine, $R^{5b}$ is H, $R^1$ is H and the combination of Y and $R^2$ for a compound corresponds in each case to one row of Table A.

Table 113
Compounds of the formula I-l in which $R^{5a}$ and $R^{5c}$ are fluorine, $R^{5b}$ is H, $R^1$ is H and the combination of Y and $R^2$ for a compound corresponds in each case to one row of Table A.

Table 114
Compounds of the formula I-l in which $R^{5a}$ and $R^{5c}$ are methyl, $R^{5b}$ is H, $R^1$ is H and the combination of Y and $R^2$ for a compound corresponds in each case to one row of Table A.

Table 115
Compounds of the formula I-l in which $R^{5a}$ and $R^{5c}$ are $CF_3$, $R^{5b}$ is H, $R^1$ is H and the combination of Y and $R^2$ for a compound corresponds in each case to one row of Table A.

Table 116
Compounds of the formula I-l in which $R^{5a}$ is chlorine and $R^{5b}$ and $R^{5c}$ are H, $R^1$ is H and the combination of Y and $R^2$ for a compound corresponds in each case to one row of Table A.

Table 117
Compounds of the formula I-l in which $R^{5a}$ is $CF_3$ and $R^{5b}$ and $R^{5c}$ are H, $R^1$ is H and the combination of Y and $R^2$ for a compound corresponds in each case to one row of Table A.

Table 118
Compounds of the formula I-l in which $R^{5a}$, $R^{5b}$ and $R^{5c}$ are chlorine, $R^1$ is H and the combination of Y and $R^2$ for a compound corresponds in each case to one row of Table A.

Table 119
Compounds of the formula I-l in which $R^{5a}$, $R^{5b}$ and $R^{5c}$ are fluorine, $R^1$ is H and the combination of Y and $R^2$ for a compound corresponds in each case to one row of Table A.

Table 120
Compounds of the formula I-l in which $R^{5a}$, $R^{5b}$ and $R^{5c}$ are methyl, $R^1$ is H and the combination of Y and $R^2$ for a compound corresponds in each case to one row of Table A.

Table 121
Compounds of the formula I-m in which $R^{5a}$ and $R^{5c}$ are chlorine, $R^{5b}$ is H, $R^1$ is H and the combination of Y and $R^2$ for a compound corresponds in each case to one row of Table A.

Table 122
Compounds of the formula I-m in which $R^{5a}$ and $R^{5c}$ are bromine, $R^{5b}$ is H, $R^1$ is H and the combination of Y and $R^2$ for a compound corresponds in each case to one row of Table A.

Table 123
Compounds of the formula I-m in which $R^{5a}$ and $R^{5c}$ are fluorine, $R^{5b}$ is H, $R^1$ is H and the combination of Y and $R^2$ for a compound corresponds in each case to one row of Table A.

Table 124
Compounds of the formula I-m in which $R^{5a}$ and $R^{5c}$ are methyl, $R^{5b}$ is H, $R^1$ is H and the combination of Y and $R^2$ for a compound corresponds in each case to one row of Table A.

Table 125
Compounds of the formula I-m in which $R^{5a}$ and $R^{5c}$ are $CF_3$, $R^{5b}$ is H, $R^1$ is H and the combination of Y and $R^2$ for a compound corresponds in each case to one row of Table A.

Table 126
Compounds of the formula I-m in which $R^{5a}$ is chlorine and $R^{5b}$ and $R^{5c}$ are H, $R^1$ is H and the combination of Y and $R^2$ for a compound corresponds in each case to one row of Table A.

Table 127
Compounds of the formula I-m in which $R^{5a}$ is $CF_3$ and $R^{5b}$ and $R^{5c}$ are H, $R^1$ is H and the combination of Y and $R^2$ for a compound corresponds in each case to one row of Table A.

Table 128
Compounds of the formula I-m in which $R^{5a}$, $R^{5b}$ and $R^{5c}$ are chlorine, $R^1$ is H and the combination of Y and $R^2$ for a compound corresponds in each case to one row of Table A.

Table 129
Compounds of the formula I-m in which $R^{5a}$, $R^{5b}$ and $R^{5c}$ are fluorine, $R^1$ is H and the combination of Y and $R^2$ for a compound corresponds in each case to one row of Table A.

Table 130
Compounds of the formula I-m in which $R^{5a}$, $R^{5b}$ and $R^{5c}$ are methyl, $R^1$ is H and the combination of Y and $R^2$ for a compound corresponds in each case to one row of Table A.

Table 131
Compounds of the formula I-n in which $R^{5a}$ and $R^{5c}$ are chlorine, $R^{5b}$ is H, $R^1$ is H and the combination of Y and $R^2$ for a compound corresponds in each case to one row of Table A.

Table 132
Compounds of the formula I-n in which $R^{5a}$ and $R^{5c}$ are bromine, $R^{5b}$ is H, $R^1$ is H and the combination of Y and $R^2$ for a compound corresponds in each case to one row of Table A.

Table 133
Compounds of the formula I-n in which $R^{5a}$ and $R^{5c}$ are fluorine, $R^{5b}$ is H, $R^1$ is H and the combination of Y and $R^2$ for a compound corresponds in each case to one row of Table A.

Table 134
Compounds of the formula I-n in which $R^{5a}$ and $R^{5c}$ are methyl, $R^{5b}$ is H, $R^1$ is H and the combination of Y and $R^2$ for a compound corresponds in each case to one row of Table A.

Table 135
Compounds of the formula I-n in which $R^{5a}$ and $R^{5c}$ are $CF_3$, $R^{5b}$ is H, $R^1$ is H and the combination of Y and $R^2$ for a compound corresponds in each case to one row of Table A.

Table 136
Compounds of the formula I-n in which $R^{5a}$ is chlorine and $R^{5b}$ and $R^{5c}$ are H, $R^1$ is H and the combination of Y and $R^2$ for a compound corresponds in each case to one row of Table A.

Table 137
Compounds of the formula I-n in which $R^{5a}$ is $CF_3$ and $R^{5b}$ and $R^{5c}$ are H, $R^1$ is H and the combination of Y and $R^2$ for a compound corresponds in each case to one row of Table A.

Table 138
Compounds of the formula I-n in which $R^{5a}$, $R^{5b}$ and $R^{5c}$ are chlorine, $R^1$ is H and the combination of Y and $R^2$ for a compound corresponds in each case to one row of Table A.

Table 139
Compounds of the formula I-n in which $R^{5a}$, $R^{5b}$ and $R^{5c}$ are fluorine, $R^1$ is H and the combination of Y and $R^2$ for a compound corresponds in each case to one row of Table A.

Table 140
Compounds of the formula I-n in which $R^{5a}$, $R^{5b}$ and $R^{5c}$ are methyl, $R^1$ is H and the combination of Y and $R^2$ for a compound corresponds in each case to one row of Table A.

Table 141
Compounds of the formula I-o in which $R^{5a}$ and $R^{5c}$ are chlorine, $R^{5b}$ is H, $R^1$ is H and the combination of Y and $R^2$ for a compound corresponds in each case to one row of Table A.

Table 142
Compounds of the formula I-o in which $R^{5a}$ and $R^{5c}$ are bromine, $R^{5b}$ is H, $R^1$ is H and the combination of Y and $R^2$ for a compound corresponds in each case to one row of Table A.

Table 143
Compounds of the formula I-o in which $R^{5a}$ and $R^{5c}$ are fluorine, $R^{5b}$ is H, $R^1$ is H and the combination of Y and $R^2$ for a compound corresponds in each case to one row of Table A.

Table 144
Compounds of the formula I-o in which $R^{5a}$ and $R^{5c}$ are methyl, $R^{5b}$ is H, $R^1$ is H and the combination of Y and $R^2$ for a compound corresponds in each case to one row of Table A.

Table 145
Compounds of the formula I-o in which $R^{5a}$ and $R^{5c}$ are $CF_3$, $R^{5b}$ is H, $R^1$ is H and the combination of Y and $R^2$ for a compound corresponds in each case to one row of Table A.

Table 146
Compounds of the formula I-o in which $R^{5a}$ is chlorine and $R^{5b}$ and $R^{5c}$ are H, $R^1$ is H and the combination of Y and $R^2$ for a compound corresponds in each case to one row of Table A.

Table 147
Compounds of the formula I-o in which $R^{5a}$ is $CF_3$ and $R^{5b}$ and $R^{5c}$ are H, $R^1$ is H and the combination of Y and $R^2$ for a compound corresponds in each case to one row of Table A.

Table 148
Compounds of the formula I-o in which $R^{5a}$, $R^{5b}$ and $R^{5c}$ are chlorine, $R^1$ is H and the combination of Y and $R^2$ for a compound corresponds in each case to one row of Table A.

Table 149
Compounds of the formula I-o in which $R^{5a}$, $R^{5b}$ and $R^{5c}$ are fluorine, $R^1$ is H and the combination of Y and $R^2$ for a compound corresponds in each case to one row of Table A.

Table 150
Compounds of the formula I-o in which $R^{5a}$, $R^{5b}$ and $R^{5c}$ are methyl, $R^1$ is H and the combination of Y and $R^2$ for a compound corresponds in each case to one row of Table A.

Table 151
Compounds of the formula I-p in which $R^{5a}$ and $R^{5c}$ are chlorine, $R^{5b}$ is H, $R^1$ is H and the combination of Y and $R^2$ for a compound corresponds in each case to one row of Table A.

Table 152
Compounds of the formula I-p in which $R^{5a}$ and $R^{5c}$ are bromine, $R^{5b}$ is H, $R^1$ is H and the combination of Y and $R^2$ for a compound corresponds in each case to one row of Table A.

Table 153
Compounds of the formula I-p in which $R^{5a}$ and $R^{5c}$ are fluorine, $R^{5b}$ is H, $R^1$ is H and the combination of Y and $R^2$ for a compound corresponds in each case to one row of Table A.

Table 154
Compounds of the formula I-p in which $R^{5a}$ and $R^{5c}$ are methyl, $R^{5b}$ is H, $R^1$ is H and the combination of Y and $R^2$ for a compound corresponds in each case to one row of Table A.

Table 155
Compounds of the formula I-p in which $R^{5a}$ and $R^{5c}$ are $CF_3$, $R^{5b}$ is H, $R^1$ is H and the combination of Y and $R^2$ for a compound corresponds in each case to one row of Table A.

Table 156
Compounds of the formula I-p in which $R^{5a}$ is chlorine and $R^{5b}$ and $R^{5c}$ are H, $R^1$ is H and the combination of Y and $R^2$ for a compound corresponds in each case to one row of Table A.

Table 157
Compounds of the formula I-p in which $R^{5a}$ is $CF_3$ and $R^{5b}$ and $R^{5c}$ are H, $R^1$ is H and the combination of Y and $R^2$ for a compound corresponds in each case to one row of Table A.

Table 158
Compounds of the formula I-p in which $R^{5a}$, $R^{5b}$ and $R^{5c}$ are chlorine, $R^1$ is H and the combination of Y and $R^2$ for a compound corresponds in each case to one row of Table A.

Table 159
Compounds of the formula I-p in which $R^{5a}$, $R^{5b}$ and $R^{5c}$ are fluorine, $R^1$ is H and the combination of Y and $R^2$ for a compound corresponds in each case to one row of Table A.

Table 160
Compounds of the formula I-p in which $R^{5a}$, $R^{5b}$ and $R^{5c}$ are methyl, $R^1$ is H and the combination of Y and $R^2$ for a compound corresponds in each case to one row of Table A.

Table 161
Compounds of the formula I-q in which $R^{5a}$ and $R^{5c}$ are chlorine, $R^{5b}$ is H, $R^1$ is H and the combination of Y and $R^2$ for a compound corresponds in each case to one row of Table A.

Table 162
Compounds of the formula I-q in which $R^{5a}$ and $R^{5c}$ are bromine, $R^{5b}$ is H, $R^1$ is H and the combination of Y and $R^2$ for a compound corresponds in each case to one row of Table A.

Table 163
Compounds of the formula I-q in which $R^{5a}$ and $R^{5c}$ are fluorine, $R^{5b}$ is H, $R^1$ is H and the combination of Y and $R^2$ for a compound corresponds in each case to one row of Table A.

Table 164
Compounds of the formula I-q in which $R^{5a}$ and $R^{5c}$ are methyl, $R^{5b}$ is H, $R^1$ is H and the combination of Y and $R^2$ for a compound corresponds in each case to one row of Table A.

Table 165
Compounds of the formula I-q in which $R^{5a}$ and $R^{5c}$ are $CF_3$, $R^{5b}$ is H, $R^1$ is H and the combination of Y and $R^2$ for a compound corresponds in each case to one row of Table A.

Table 166
Compounds of the formula I-q in which $R^{5a}$ is chlorine and $R^{5b}$ and $R^{5c}$ are H, $R^1$ is H and the combination of Y and $R^2$ for a compound corresponds in each case to one row of Table A.

Table 167
Compounds of the formula I-q in which $R^{5a}$ is $CF_3$ and $R^{5b}$ and $R^{5c}$ are H, $R^1$ is H and the combination of Y and $R^2$ for a compound corresponds in each case to one row of Table A.

Table 168
Compounds of the formula I-q in which $R^{5a}$, $R^{5b}$ and $R^{5c}$ are chlorine, $R^1$ is H and the combination of Y and $R^2$ for a compound corresponds in each case to one row of Table A.

Table 169
Compounds of the formula I-q in which $R^{5a}$, $R^{5b}$ and $R^{5c}$ are fluorine, $R^1$ is H and the combination of Y and $R^2$ for a compound corresponds in each case to one row of Table A.

Table 170
Compounds of the formula I-q in which $R^{5a}$, $R^{5b}$ and $R^{5c}$ are methyl, $R^1$ is H and the combination of Y and $R^2$ for a compound corresponds in each case to one row of Table A.

Table 171
Compounds of the formula I-r in which $R^{5a}$ and $R^{5c}$ are chlorine, $R^{5b}$ is H, $R^1$ is H and the combination of Y and $R^2$ for a compound corresponds in each case to one row of Table A.

Table 172
Compounds of the formula I-r in which $R^{5a}$ and $R^{5c}$ are bromine, $R^{5b}$ is H, $R^1$ is H and the combination of Y and $R^2$ for a compound corresponds in each case to one row of Table A.

Table 173
Compounds of the formula I-r in which $R^{5a}$ and $R^{5c}$ are fluorine, $R^{5b}$ is H, $R^1$ is H and the combination of Y and $R^2$ for a compound corresponds in each case to one row of Table A.

Table 174
Compounds of the formula I-r in which $R^{5a}$ and $R^{5c}$ are methyl, $R^{5b}$ is H, $R^1$ is H and the combination of Y and $R^2$ for a compound corresponds in each case to one row of Table A.

Table 175
Compounds of the formula I-r in which $R^{5a}$ and $R^{5c}$ are $CF_3$, $R^{5b}$ is H, $R^1$ is H and the combination of Y and $R^2$ for a compound corresponds in each case to one row of Table A.

Table 176
Compounds of the formula I-r in which $R^{5a}$ is chlorine and $R^{5b}$ and $R^{5c}$ are H, $R^1$ is H and the combination of Y and $R^2$ for a compound corresponds in each case to one row of Table A.

Table 177
Compounds of the formula I-r in which $R^{5a}$ is $CF_3$ and $R^{5b}$ and $R^{5c}$ are H, $R^1$ is H and the combination of Y and $R^2$ for a compound corresponds in each case to one row of Table A.

Table 178
Compounds of the formula I-r in which $R^{5a}$, $R^{5b}$ and $R^{5c}$ are chlorine, $R^1$ is H and the combination of Y and $R^2$ for a compound corresponds in each case to one row of Table A.

Table 179
Compounds of the formula I-r in which $R^{5a}$, $R^{5b}$ and $R^{5c}$ are fluorine, $R^1$ is H and the combination of Y and $R^2$ for a compound corresponds in each case to one row of Table A.

Table 180
Compounds of the formula I-r in which $R^{5a}$, $R^{5b}$ and $R^{5c}$ are methyl, $R^1$ is H and the combination of Y and $R^2$ for a compound corresponds in each case to one row of Table A.

Table 181
Compounds of the formula I-s in which $R^{5a}$ and $R^{5c}$ are chlorine, $R^{5b}$ is H, $R^1$ is H and the combination of Y and $R^2$ for a compound corresponds in each case to one row of Table A.

Table 182
Compounds of the formula I-s in which $R^{5a}$ and $R^{5c}$ are bromine, $R^{5b}$ is H, $R^1$ is H and the combination of Y and $R^2$ for a compound corresponds in each case to one row of Table A.

Table 183
Compounds of the formula I-s in which $R^{5a}$ and $R^{5c}$ are fluorine, $R^{5b}$ is H, $R^1$ is H and the combination of Y and $R^2$ for a compound corresponds in each case to one row of Table A.

Table 184
Compounds of the formula I-s in which $R^{5a}$ and $R^{5c}$ are methyl, $R^{5b}$ is H, $R^1$ is H and the combination of Y and $R^2$ for a compound corresponds in each case to one row of Table A.

Table 185
Compounds of the formula I-s in which $R^{5a}$ and $R^{5c}$ are $CF_3$, $R^{5b}$ is H, $R^1$ is H and the combination of Y and $R^2$ for a compound corresponds in each case to one row of Table A.

Table 186
Compounds of the formula I-s in which $R^{5a}$ is chlorine and $R^{5b}$ and $R^{5c}$ are H, $R^1$ is H and the combination of Y and $R^2$ for a compound corresponds in each case to one row of Table A.

Table 187
Compounds of the formula I-s in which $R^{5a}$ is $CF_3$ and $R^{5b}$ and $R^{5c}$ are H, $R^1$ is H and the combination of Y and $R^2$ for a compound corresponds in each case to one row of Table A.

Table 188
Compounds of the formula I-s in which $R^{5a}$, $R^{5b}$ and $R^{5c}$ are chlorine, $R^1$ is H and the combination of Y and $R^2$ for a compound corresponds in each case to one row of Table A.

Table 189
Compounds of the formula I-s in which $R^{5a}$, $R^{5b}$ and $R^{5c}$ are fluorine, $R^1$ is H and the combination of Y and $R^2$ for a compound corresponds in each case to one row of Table A.

Table 190
Compounds of the formula I-s in which $R^{5a}$, $R^{5b}$ and $R^{5c}$ are methyl, $R^1$ is H and the combination of Y and $R^2$ for a compound corresponds in each case to one row of Table A.

Table 191
Compounds of the formula I-t in which $R^{5a}$ and $R^{5c}$ are chlorine, $R^{5b}$ is H, $R^1$ is H and the combination of Y and $R^2$ for a compound corresponds in each case to one row of Table A.

Table 192
Compounds of the formula I-t in which $R^{5a}$ and $R^{5c}$ are bromine, $R^{5b}$ is H, $R^1$ is H and the combination of Y and $R^2$ for a compound corresponds in each case to one row of Table A.

Table 193, $R^1$ is H
Compounds of the formula I-t in which $R^{5a}$ and $R^{5c}$ are fluorine, $R^{5b}$ is H, $R^1$ is H and the combination of Y and $R^2$ for a compound corresponds in each case to one row of Table A.

Table 194
Compounds of the formula I-t in which $R^{5a}$ and $R^{5c}$ are methyl, $R^{5b}$ is H, $R^1$ is H and the combination of Y and $R^2$ for a compound corresponds in each case to one row of Table A.

Table 195
Compounds of the formula I-t in which $R^{5a}$ and $R^{5c}$ are $CF_3$, $R^{5b}$ is H, $R^1$ is H and the combination of Y and $R^2$ for a compound corresponds in each case to one row of Table A.

Table 196
Compounds of the formula I-t in which $R^{5a}$ is chlorine and $R^{5b}$ and $R^{5c}$ are H, $R^1$ is H and the combination of Y and $R^2$ for a compound corresponds in each case to one row of Table A.

Table 197
Compounds of the formula I-t in which $R^{5a}$ is $CF_3$ and $R^{5b}$ and $R^{5c}$ are H, $R^1$ is H and the combination of Y and $R^2$ for a compound corresponds in each case to one row of Table A.

Table 198
Compounds of the formula I-t in which $R^{5a}$, $R^{5b}$ and $R^{5c}$ are chlorine, $R^1$ is H and the combination of Y and $R^2$ for a compound corresponds in each case to one row of Table A.

Table 199
Compounds of the formula I-t in which $R^{5a}$, $R^{5b}$ and $R^{5c}$ are fluorine, $R^1$ is H and the combination of Y and $R^2$ for a compound corresponds in each case to one row of Table A.

Table 200
Compounds of the formula I-t in which $R^{5a}$, $R^{5b}$ and $R^{5c}$ are methyl, $R^1$ is H and the combination of Y and $R^2$ for a compound corresponds in each case to one row of Table A.

Table 201
Compounds of the formula I-u in which $R^{5a}$ and $R^{5c}$ are chlorine, $R^{5b}$ is H, $R^1$ is H and the combination of Y and $R^2$ for a compound corresponds in each case to one row of Table A.

Table 202
Compounds of the formula I-u in which $R^{5a}$ and $R^{5c}$ are bromine, $R^{5b}$ is H, $R^1$ is H and the combination of Y and $R^2$ for a compound corresponds in each case to one row of Table A.

Table 203
Compounds of the formula I-u in which $R^{5a}$ and $R^{5c}$ are fluorine, $R^{5b}$ is H, $R^1$ is H and the combination of Y and $R^2$ for a compound corresponds in each case to one row of Table A.

Table 204
Compounds of the formula I-u in which $R^{5a}$ and $R^{5c}$ are methyl, $R^{5b}$ is H, $R^1$ is H and the combination of Y and $R^2$ for a compound corresponds in each case to one row of Table A.

Table 205
Compounds of the formula I-u in which $R^{5a}$ and $R^{5c}$ are $CF_3$, $R^{5b}$ is H, $R^1$ is H and the combination of Y and $R^2$ for a compound corresponds in each case to one row of Table A.

Table 206
Compounds of the formula I-u in which $R^{5a}$ is chlorine and $R^{5b}$ and $R^{5c}$ are H, $R^1$ is H and the combination of Y and $R^2$ for a compound corresponds in each case to one row of Table A.

Table 207
Compounds of the formula I-u in which $R^{5a}$ is $CF_3$ and $R^{5b}$ and $R^{5c}$ are H, $R^1$ is H and the combination of Y and $R^2$ for a compound corresponds in each case to one row of Table A.

Table 208
Compounds of the formula I-u in which $R^{5a}$, $R^{5b}$ and $R^{5c}$ are chlorine, $R^1$ is H and the combination of Y and $R^2$ for a compound corresponds in each case to one row of Table A.

Table 209
Compounds of the formula I-u in which $R^{5a}$, $R^{5b}$ and $R^{5c}$ are fluorine, $R^1$ is H and the combination of Y and $R^2$ for a compound corresponds in each case to one row of Table A.

Table 210
Compounds of the formula I-u in which $R^{5a}$, $R^{5b}$ and $R^{5c}$ are methyl, $R^1$ is H and the combination of Y and $R^2$ for a compound corresponds in each case to one row of Table A.

Table 211
Compounds of the formula I-v in which $R^{5a}$ and $R^{5c}$ are chlorine, $R^{5b}$ is H, $R^1$ is H and the combination of Y and $R^2$ for a compound corresponds in each case to one row of Table A.

Table 212
Compounds of the formula I-v in which $R^{5a}$ and $R^{5c}$ are bromine, $R^{5b}$ is H, $R^1$ is H and the combination of Y and $R^2$ for a compound corresponds in each case to one row of Table A.

Table 213
Compounds of the formula I-v in which $R^{5a}$ and $R^{5c}$ are fluorine, $R^{5b}$ is H, $R^1$ is H and the combination of Y and $R^2$ for a compound corresponds in each case to one row of Table A.

Table 214
Compounds of the formula I-v in which $R^{5a}$ and $R^{5c}$ are methyl, $R^{5b}$ is H, $R^1$ is H and the combination of Y and $R^2$ for a compound corresponds in each case to one row of Table A.

Table 215
Compounds of the formula I-v in which $R^{5a}$ and $R^{5c}$ are $CF_3$, $R^{5b}$ is H, $R^1$ is H and the combination of Y and $R^2$ for a compound corresponds in each case to one row of Table A.

Table 216
Compounds of the formula I-v in which $R^{5a}$ is chlorine and $R^{5b}$ and $R^{5c}$ are H, $R^1$ is H and the combination of Y and $R^2$ for a compound corresponds in each case to one row of Table A.

Table 217
Compounds of the formula I-v in which $R^{5a}$ is $CF_3$ and $R^{5b}$ and $R^{5c}$ are H, $R^1$ is H and the combination of Y and $R^2$ for a compound corresponds in each case to one row of Table A.

Table 218
Compounds of the formula I-v in which $R^{5a}$, $R^{5b}$ and $R^{5c}$ are chlorine, $R^1$ is H and the combination of Y and $R^2$ for a compound corresponds in each case to one row of Table A.

Table 219
Compounds of the formula I-v in which $R^{5a}$, $R^{5b}$ and $R^{5c}$ are fluorine, $R^1$ is H and the combination of Y and $R^2$ for a compound corresponds in each case to one row of Table A.

Table 220
Compounds of the formula I-v in which $R^{5a}$, $R^{5b}$ and $R^{5c}$ are methyl, $R^1$ is H and the combination of Y and $R^2$ for a compound corresponds in each case to one row of Table A.

Table 221
Compounds of the formula I-w in which $R^{5a}$ and $R^{5c}$ are chlorine, $R^{5b}$ is H, $R^1$ is H and the combination of Y and $R^2$ for a compound corresponds in each case to one row of Table A.

Table 222
Compounds of the formula I-w in which $R^{5a}$ and $R^{5c}$ are bromine, $R^{5b}$ is H, $R^1$ is H and the combination of Y and $R^2$ for a compound corresponds in each case to one row of Table A.

Table 223
Compounds of the formula I-w in which $R^{5a}$ and $R^{5c}$ are fluorine, $R^{5b}$ is H, $R^1$ is H and the combination of Y and $R^2$ for a compound corresponds in each case to one row of Table A.

Table 224
Compounds of the formula I-w in which $R^{5a}$ and $R^{5c}$ are methyl, $R^{5b}$ is H, $R^1$ is H and the combination of Y and $R^2$ for a compound corresponds in each case to one row of Table A.

Table 225
Compounds of the formula I-w in which $R^{5a}$ and $R^{5c}$ are $CF_3$, $R^{5b}$ is H, $R^1$ is H and the combination of Y and $R^2$ for a compound corresponds in each case to one row of Table A.

Table 226
Compounds of the formula I-w in which $R^{5a}$ is chlorine and $R^{5b}$ and $R^{5c}$ are H, $R^1$ is H and the combination of Y and $R^2$ for a compound corresponds in each case to one row of Table A.

Table 227
Compounds of the formula I-w in which $R^{5a}$ is $CF_3$ and $R^{5b}$ and $R^{5c}$ are H, $R^1$ is H and the combination of Y and $R^2$ for a compound corresponds in each case to one row of Table A.

Table 228
Compounds of the formula I-w in which $R^{5a}$, $R^{5b}$ and $R^{5c}$ are chlorine, $R^1$ is H and the combination of Y and $R^2$ for a compound corresponds in each case to one row of Table A.

Table 229
Compounds of the formula I-w in which $R^{5a}$, $R^{5b}$ and $R^{5c}$ are fluorine, $R^1$ is H and the combination of Y and $R^2$ for a compound corresponds in each case to one row of Table A.

Table 230
Compounds of the formula I-w in which $R^{5a}$, $R^{5b}$ and $R^{5c}$ are methyl, $R^1$ is H and the combination of Y and $R^2$ for a compound corresponds in each case to one row of Table A.

Table 231
Compounds of the formula I-x in which $R^{5a}$ and $R^{5c}$ are chlorine, $R^{5b}$ is H, $R^1$ is H and the combination of Y and $R^2$ for a compound corresponds in each case to one row of Table A.

Table 232
Compounds of the formula I-x in which $R^{5a}$ and $R^{5c}$ are bromine, $R^{5b}$ is H, $R^1$ is H and the combination of Y and $R^2$ for a compound corresponds in each case to one row of Table A.

Table 233
Compounds of the formula I-x in which $R^{5a}$ and $R^{5c}$ are fluorine, $R^{5b}$ is H, $R^1$ is H and the combination of Y and $R^2$ for a compound corresponds in each case to one row of Table A.

Table 234
Compounds of the formula I-x in which $R^{5a}$ and $R^{5c}$ are methyl, $R^{5b}$ is H, $R^1$ is H and the combination of Y and $R^2$ for a compound corresponds in each case to one row of Table A.

Table 235
Compounds of the formula I-x in which $R^{5a}$ and $R^{5c}$ are $CF_3$, $R^{5b}$ is H, $R^1$ is H and the combination of Y and $R^2$ for a compound corresponds in each case to one row of Table A.

Table 236
Compounds of the formula I-x in which $R^{5a}$ is chlorine and $R^{5b}$ and $R^{5c}$ are H, $R^1$ is H and the combination of Y and $R^2$ for a compound corresponds in each case to one row of Table A.

Table 237
Compounds of the formula I-x in which $R^{5a}$ is $CF_3$ and $R^{5b}$ and $R^{5c}$ are H, $R^1$ is H and the combination of Y and $R^2$ for a compound corresponds in each case to one row of Table A.

Table 238
Compounds of the formula I-x in which $R^{5a}$, $R^{5b}$ and $R^{5c}$ are chlorine, $R^1$ is H and the combination of Y and $R^2$ for a compound corresponds in each case to one row of Table A.

Table 239
Compounds of the formula I-x in which $R^{5a}$, $R^{5b}$ and $R^{5c}$ are fluorine, $R^1$ is H and the combination of Y and $R^2$ for a compound corresponds in each case to one row of Table A.

Table 240
Compounds of the formula I-x in which $R^{5a}$, $R^{5b}$ and $R^{5c}$ are methyl, $R^1$ is H and the combination of Y and $R^2$ for a compound corresponds in each case to one row of Table A.

Table 241
Compounds of the formula I-y in which $R^{5a}$ and $R^{5c}$ are chlorine, $R^{5b}$ is H, $R^1$ is H and the combination of Y and $R^2$ for a compound corresponds in each case to one row of Table A.

Table 242
Compounds of the formula I-y in which $R^{5a}$ and $R^{5c}$ are bromine, $R^{5b}$ is H, $R^1$ is H and the combination of Y and $R^2$ for a compound corresponds in each case to one row of Table A.

Table 243
Compounds of the formula I-y in which $R^{5a}$ and $R^{5c}$ are fluorine, $R^{5b}$ is H, $R^1$ is H and the combination of Y and $R^2$ for a compound corresponds in each case to one row of Table A.

Table 244
Compounds of the formula I-y in which $R^{5a}$ and $R^{5c}$ are methyl, $R^{5b}$ is H, $R^1$ is H and the combination of Y and $R^2$ for a compound corresponds in each case to one row of Table A.

Table 245
Compounds of the formula I-y in which $R^{5a}$ and $R^{5c}$ are $CF_3$, $R^{5b}$ is H, $R^1$ is H and the combination of Y and $R^2$ for a compound corresponds in each case to one row of Table A.

Table 246
Compounds of the formula I-y in which $R^{5a}$ is chlorine and $R^{5b}$ and $R^{5c}$ are H, $R^1$ is H and the combination of Y and $R^2$ for a compound corresponds in each case to one row of Table A.

Table 247
Compounds of the formula I-y in which $R^{5a}$ is $CF_3$ and $R^{5b}$ and $R^{5c}$ are H, $R^1$ is H and the combination of Y and $R^2$ for a compound corresponds in each case to one row of Table A.

Table 248
Compounds of the formula I-y in which $R^{5a}$, $R^{5b}$ and $R^{5c}$ are chlorine, $R^1$ is H and the combination of Y and $R^2$ for a compound corresponds in each case to one row of Table A.

Table 249
Compounds of the formula I-y in which $R^{5a}$, $R^{5b}$ and $R^{5c}$ are fluorine, $R^1$ is H and the combination of Y and $R^2$ for a compound corresponds in each case to one row of Table A.

Table 250
Compounds of the formula I-y in which $R^{5a}$, $R^{5b}$ and $R^{5c}$ are methyl, $R^1$ is H and the combination of Y and $R^2$ for a compound corresponds in each case to one row of Table A.

Table 251
Compounds of the formula I-z in which $R^{5a}$ and $R^{5c}$ are chlorine, $R^{5b}$ is H, $R^1$ is H and the combination of Y and $R^2$ for a compound corresponds in each case to one row of Table A.

Table 252
Compounds of the formula I-z in which $R^{5a}$ and $R^{5c}$ are bromine, $R^{5b}$ is H, $R^1$ is H and the combination of Y and $R^2$ for a compound corresponds in each case to one row of Table A.

Table 253
Compounds of the formula I-z in which $R^{5a}$ and $R^{5c}$ are fluorine, $R^{5b}$ is H, $R^1$ is H and the combination of Y and $R^2$ for a compound corresponds in each case to one row of Table A.

Table 254
Compounds of the formula I-z in which $R^{5a}$ and $R^{5c}$ are methyl, $R^{5b}$ is H, $R^1$ is H and the combination of Y and $R^2$ for a compound corresponds in each case to one row of Table A.

Table 255
Compounds of the formula I-z in which $R^{5a}$ and $R^{5c}$ are $CF_3$, $R^{5b}$ is H, $R^1$ is H and the combination of Y and $R^2$ for a compound corresponds in each case to one row of Table A.

Table 256
Compounds of the formula I-z in which $R^{5a}$ is chlorine and $R^{5b}$ and $R^{5c}$ are H, $R^1$ is H and the combination of Y and $R^2$ for a compound corresponds in each case to one row of Table A.

Table 257
Compounds of the formula I-z in which $R^{5a}$ is $CF_3$ and $R^{5b}$ and $R^{5c}$ are H, $R^1$ is H and the combination of Y and $R^2$ for a compound corresponds in each case to one row of Table A.

Table 258
Compounds of the formula I-z in which $R^{5a}$, $R^{5b}$ and $R^{5c}$ are chlorine, $R^1$ is H and the combination of Y and $R^2$ for a compound corresponds in each case to one row of Table A.

Table 259
Compounds of the formula I-z in which $R^{5a}$, $R^{5b}$ and $R^{5c}$ are fluorine, $R^1$ is H and the combination of Y and $R^2$ for a compound corresponds in each case to one row of Table A.

Table 260
Compounds of the formula I-z in which $R^{5a}$, $R^{5b}$ and $R^{5c}$ are methyl, $R^1$ is H and the combination of Y and $R^2$ for a compound corresponds in each case to one row of Table A.

Table 261
Compounds of the formula I-aa in which $R^{5a}$ is chlorine, $R^1$ is H and the combination of Y and $R^2$ for a compound corresponds in each case to one row of Table A.

Table 262
Compounds of the formula I-aa in which $R^{5a}$ is bromine, $R^1$ is H and the combination of Y and $R^2$ for a compound corresponds in each case to one row of Table A.

Table 263
Compounds of the formula I-aa in which $R^{5a}$ is fluorine, $R^1$ is H and the combination of Y and $R^2$ for a compound corresponds in each case to one row of Table A.

Table 264
Compounds of the formula I-aa in which $R^{5a}$ is methyl, $R^1$ is H and the combination of Y and $R^2$ for a compound corresponds in each case to one row of Table A.

Table 265
Compounds of the formula I-aa in which $R^{5a}$ is $CF_3$, $R^1$ is H and the combination of Y and $R^2$ for a compound corresponds in each case to one row of Table A.

Table 266
Compounds of the formula I-bb in which $R^{5a}$ is chlorine, $R^1$ is H and the combination of Y and $R^2$ for a compound corresponds in each case to one row of Table A.

Table 267
Compounds of the formula I-bb in which $R^{5a}$ is bromine, $R^1$ is H and the combination of Y and $R^2$ for a compound corresponds in each case to one row of Table A.

Table 268
Compounds of the formula I-bb in which $R^{5a}$ is fluorine, $R^1$ is H and the combination of Y and $R^2$ for a compound corresponds in each case to one row of Table A.

Table 269
Compounds of the formula I-bb in which $R^{5a}$ is methyl, $R^1$ is H and the combination of Y and $R^2$ for a compound corresponds in each case to one row of Table A.

Table 270
Compounds of the formula I-bb in which $R^{5a}$ is $CF_3$, $R^1$ is H and the combination of Y and $R^2$ for a compound corresponds in each case to one row of Table A.

Table 271
Compounds of the formula I-cc in which $R^{5a}$ is chlorine, $R^1$ is H and the combination of Y and $R^2$ for a compound corresponds in each case to one row of Table A.

Table 272
Compounds of the formula I-cc in which $R^{5a}$ is bromine, $R^1$ is H and the combination of Y and $R^2$ for a compound corresponds in each case to one row of Table A.

Table 273
Compounds of the formula I-cc in which $R^{5a}$ is fluorine, $R^1$ is H and the combination of Y and $R^2$ for a compound corresponds in each case to one row of Table A.

Table 274
Compounds of the formula I-cc in which $R^{5a}$ is methyl, $R^1$ is H and the combination of Y and $R^2$ for a compound corresponds in each case to one row of Table A.

Table 275
Compounds of the formula I-cc in which $R^{5a}$ is $CF_3$, $R^1$ is H and the combination of Y and $R^2$ for a compound corresponds in each case to one row of Table A.

Table 276
Compounds of the formula I-dd in which $R^{5a}$ is chlorine, $R^1$ is H and the combination of Y and $R^2$ for a compound corresponds in each case to one row of Table A.

Table 277
Compounds of the formula I-dd in which $R^{5a}$ is bromine, $R^1$ is H and the combination of Y and $R^2$ for a compound corresponds in each case to one row of Table A.

Table 278
Compounds of the formula I-dd in which $R^{5a}$ is fluorine, $R^1$ is H and the combination of Y and $R^2$ for a compound corresponds in each case to one row of Table A.

Table 279
Compounds of the formula I-dd in which $R^{5a}$ is methyl, $R^1$ is H and the combination of Y and $R^2$ for a compound corresponds in each case to one row of Table A.

Table 280
Compounds of the formula I-dd in which $R^{5a}$ is $CF_3$, $R^1$ is H and the combination of Y and $R^2$ for a compound corresponds in each case to one row of Table A.

Table 281
Compounds of the formula I-ee in which $R^{5a}$ is chlorine, $R^1$ is H and the combination of Y and $R^2$ for a compound corresponds in each case to one row of Table A.

Table 282
Compounds of the formula I-ee in which $R^{5a}$ is bromine, $R^1$ is H and the combination of Y and $R^2$ for a compound corresponds in each case to one row of Table A.

Table 283
Compounds of the formula I-ee in which $R^{5a}$ is fluorine, $R^1$ is H and the combination of Y and $R^2$ for a compound corresponds in each case to one row of Table A.

Table 284
Compounds of the formula I-ee in which $R^{5a}$ is methyl, $R^1$ is H and the combination of Y and $R^2$ for a compound corresponds in each case to one row of Table A.

Table 285
Compounds of the formula I-ee in which $R^{5a}$ is $CF_3$, $R^1$ is H and the combination of Y and $R^2$ for a compound corresponds in each case to one row of Table A.

Table 286
Compounds of the formula I-ff in which $R^{5a}$ is chlorine, $R^1$ is H and the combination of Y and $R^2$ for a compound corresponds in each case to one row of Table A.

Table 287
Compounds of the formula I-ff in which $R^{5a}$ is bromine, $R^1$ is H and the combination of Y and $R^2$ for a compound corresponds in each case to one row of Table A.

Table 288
Compounds of the formula I-ff in which $R^{5a}$ is fluorine, $R^1$ is H and the combination of Y and $R^2$ for a compound corresponds in each case to one row of Table A.

Table 289
Compounds of the formula I-ff in which $R^{5a}$ is methyl, $R^1$ is H and the combination of Y and $R^2$ for a compound corresponds in each case to one row of Table A.

Table 290
Compounds of the formula I-ff in which $R^{5a}$ is $CF_3$, $R^1$ is H and the combination of Y and $R^2$ for a compound corresponds in each case to one row of Table A.

Table 291
Compounds of the formula I-gg in which $R^{5a}$ is chlorine, $R^1$ is H and the combination of Y and $R^2$ for a compound corresponds in each case to one row of Table A.

Table 292
Compounds of the formula I-gg in which $R^{5a}$ is bromine, $R^1$ is H and the combination of Y and $R^2$ for a compound corresponds in each case to one row of Table A.

Table 293
Compounds of the formula I-gg in which $R^{5a}$ is fluorine, $R^1$ is H and the combination of Y and $R^2$ for a compound corresponds in each case to one row of Table A.

Table 294
Compounds of the formula I-gg in which $R^{5a}$ is methyl, $R^1$ is H and the combination of Y and $R^2$ for a compound corresponds in each case to one row of Table A.

Table 295
Compounds of the formula I-gg in which $R^{5a}$ is $CF_3$, $R^1$ is H and the combination of Y and $R^2$ for a compound corresponds in each case to one row of Table A.

Table 296
Compounds of the formula I-hh in which $R^{5a}$ is chlorine, $R^1$ is H and the combination of Y and $R^2$ for a compound corresponds in each case to one row of Table A.

Table 297
Compounds of the formula I-hh in which $R^{5a}$ is bromine, $R^1$ is H and the combination of Y and $R^2$ for a compound corresponds in each case to one row of Table A.

Table 298
Compounds of the formula I-hh in which $R^{5a}$ is fluorine, $R^1$ is H and the combination of Y and $R^2$ for a compound corresponds in each case to one row of Table A.

Table 299
Compounds of the formula I-hh in which $R^{5a}$ is methyl, $R^1$ is H and the combination of Y and $R^2$ for a compound corresponds in each case to one row of Table A.

Table 300
Compounds of the formula I-hh in which $R^{5a}$ is $CF_3$, $R^1$ is H and the combination of Y and $R^2$ for a compound corresponds in each case to one row of Table A.

Table 301
Compounds of the formula I-ii in which $R^{5a}$ is chlorine, $R^1$ is H and the combination of Y and $R^2$ for a compound corresponds in each case to one row of Table A.

Table 302
Compounds of the formula I-ii in which $R^{5a}$ is bromine, $R^1$ is H and the combination of Y and $R^2$ for a compound corresponds in each case to one row of Table A.
Table 303
Compounds of the formula I-ii in which $R^{5a}$ is fluorine, $R^1$ is H and the combination of Y and $R^2$ for a compound corresponds in each case to one row of Table A.
Table 304
Compounds of the formula I-ii in which $R^{5a}$ is methyl, $R^1$ is H and the combination of Y and $R^2$ for a compound corresponds in each case to one row of Table A.
Table 305
Compounds of the formula I-ii in which $R^{5a}$ is $CF_3$, $R^1$ is H and the combination of Y and $R^2$ for a compound corresponds in each case to one row of Table A.
Table 306
Compounds of the formula I-jj in which $R^{5a}$ is chlorine, $R^1$ is H and the combination of Y and $R^2$ for a compound corresponds in each case to one row of Table A.
Table 307
Compounds of the formula I-jj in which $R^{5a}$ is bromine, $R^1$ is H and the combination of Y and $R^2$ for a compound corresponds in each case to one row of Table A.
Table 308
Compounds of the formula I-jj in which $R^{5a}$ is fluorine, $R^1$ is H and the combination of Y and $R^2$ for a compound corresponds in each case to one row of Table A.
Table 309
Compounds of the formula I-jj in which $R^{5a}$ is methyl, $R^1$ is H and the combination of Y and $R^2$ for a compound corresponds in each case to one row of Table A.
Table 310
Compounds of the formula I-jj in which $R^{5a}$ is $CF_3$, $R^1$ is H and the combination of Y and $R^2$ for a compound corresponds in each case to one row of Table A.
Table 311
Compounds of the formula I-kk in which $R^{5a}$ is chlorine, $R^1$ is H and the combination of Y and $R^2$ for a compound corresponds in each case to one row of Table A.
Table 312
Compounds of the formula I-kk in which $R^{5a}$ is bromine, $R^1$ is H and the combination of Y and $R^2$ for a compound corresponds in each case to one row of Table A.
Table 313
Compounds of the formula I-kk in which $R^{5a}$ is fluorine, $R^1$ is H and the combination of Y and $R^2$ for a compound corresponds in each case to one row of Table A.
Table 314
Compounds of the formula I-kk in which $R^{5a}$ is methyl, $R^1$ is H and the combination of Y and $R^2$ for a compound corresponds in each case to one row of Table A.
Table 315
Compounds of the formula I-kk in which $R^{5a}$ is $CF_3$, $R^1$ is H and the combination of Y and $R^2$ for a compound corresponds in each case to one row of Table A.
Table 316
Compounds of the formula I-ll in which $R^{5a}$ is chlorine, $R^1$ is H and the combination of Y and $R^2$ for a compound corresponds in each case to one row of Table A.
Table 317
Compounds of the formula I-ll in which $R^{5a}$ is bromine, $R^1$ is H and the combination of Y and $R^2$ for a compound corresponds in each case to one row of Table A.
Table 318
Compounds of the formula I-ll in which $R^{5a}$ is fluorine, $R^1$ is H and the combination of Y and $R^2$ for a compound corresponds in each case to one row of Table A.
Table 319
Compounds of the formula I-ll in which $R^{5a}$ is methyl, $R^1$ is H and the combination of Y and $R^2$ for a compound corresponds in each case to one row of Table A.
Table 320
Compounds of the formula I-ll in which $R^{5a}$ is $CF_3$, $R^1$ is H and the combination of Y and $R^2$ for a compound corresponds in each case to one row of Table A.
Table 321
Compounds of the formula I-mm in which $R^{5a}$ is chlorine, $R^1$ is H and the combination of Y and $R^2$ for a compound corresponds in each case to one row of Table A.
Table 322
Compounds of the formula I-mm in which $R^{5a}$ is bromine, $R^1$ is H and the combination of Y and $R^2$ for a compound corresponds in each case to one row of Table A.
Table 323
Compounds of the formula I-mm in which $R^{5a}$ is fluorine, $R^1$ is H and the combination of Y and $R^2$ for a compound corresponds in each case to one row of Table A.
Table 324
Compounds of the formula I-mm in which $R^{5a}$ is methyl, $R^1$ is H and the combination of Y and $R^2$ for a compound corresponds in each case to one row of Table A.
Table 325
Compounds of the formula I-mm in which $R^{5a}$ is $CF_3$, $R^1$ is H and the combination of Y and $R^2$ for a compound corresponds in each case to one row of Table A.
Table 326
Compounds of the formula I-nn in which $R^{5a}$ is chlorine, $R^1$ is H and the combination of Y and $R^2$ for a compound corresponds in each case to one row of Table A.
Table 327
Compounds of the formula I-nn in which $R^{5a}$ is bromine, $R^1$ is H and the combination of Y and $R^2$ for a compound corresponds in each case to one row of Table A.
Table 328
Compounds of the formula I-nn in which $R^{5a}$ is fluorine, $R^1$ is H and the combination of Y and $R^2$ for a compound corresponds in each case to one row of Table A.
Table 329
Compounds of the formula I-nn in which $R^{5a}$ is methyl, $R^1$ is H and the combination of Y and $R^2$ for a compound corresponds in each case to one row of Table A.
Table 330
Compounds of the formula I-nn in which $R^{5a}$ is $CF_3$, $R^1$ is H and the combination of Y and $R^2$ for a compound corresponds in each case to one row of Table A.
Table 331
Compounds of the formula I-oo in which $R^{5a}$ is chlorine, $R^1$ is H and the combination of Y and $R^2$ for a compound corresponds in each case to one row of Table A.
Table 332
Compounds of the formula I-oo in which $R^{5a}$ is bromine, $R^1$ is H and the combination of Y and $R^2$ for a compound corresponds in each case to one row of Table A.
Table 333
Compounds of the formula I-oo in which $R^{5a}$ is fluorine, $R^1$ is H and the combination of Y and $R^2$ for a compound corresponds in each case to one row of Table A.

Table 334
Compounds of the formula I-oo in which $R^{5a}$ is methyl, $R^1$ is H and the combination of Y and $R^2$ for a compound corresponds in each case to one row of Table A.

Table 335
Compounds of the formula I-oo in which $R^{5a}$ is $CF_3$, $R^1$ is H and the combination of Y and $R^2$ for a compound corresponds in each case to one row of Table A.

Table 336
Compounds of the formula I-pp in which $R^{5a}$ is chlorine, $R^1$ is H and the combination of Y and $R^2$ for a compound corresponds in each case to one row of Table A.

Table 337
Compounds of the formula I-pp in which $R^{5a}$ is bromine, $R^1$ is H and the combination of Y and $R^2$ for a compound corresponds in each case to one row of Table A.

Table 338
Compounds of the formula I-pp in which $R^{5a}$ is fluorine, $R^1$ is H and the combination of Y and $R^2$ for a compound corresponds in each case to one row of Table A.

Table 339
Compounds of the formula I-pp in which $R^{5a}$ is methyl, $R^1$ is H and the combination of Y and $R^2$ for a compound corresponds in each case to one row of Table A.

Table 340
Compounds of the formula I-pp in which $R^{5a}$ is $CF_3$, $R^1$ is H and the combination of Y and $R^2$ for a compound corresponds in each case to one row of Table A.

Table 341
Compounds of the formula I-qq in which $R^{5a}$ is chlorine, $R^1$ is H and the combination of Y and $R^2$ for a compound corresponds in each case to one row of Table A.

Table 342
Compounds of the formula I-qq in which $R^{5a}$ is bromine, $R^1$ is H and the combination of Y and $R^2$ for a compound corresponds in each case to one row of Table A.

Table 343
Compounds of the formula I-qq in which $R^{5a}$ is fluorine, $R^1$ is H and the combination of Y and $R^2$ for a compound corresponds in each case to one row of Table A.

Table 344
Compounds of the formula I-qq in which $R^{5a}$ is methyl, $R^1$ is H and the combination of Y and $R^2$ for a compound corresponds in each case to one row of Table A.

Table 345
Compounds of the formula I-qq in which $R^{5a}$ is $CF_3$, $R^1$ is H and the combination of Y and $R^2$ for a compound corresponds in each case to one row of Table A.

Table 346
Compounds of the formula I-rr in which $R^{5a}$ is chlorine, $R^1$ is H and the combination of Y and $R^2$ for a compound corresponds in each case to one row of Table A.

Table 347
Compounds of the formula I-rr in which $R^{5a}$ is bromine, $R^1$ is H and the combination of Y and $R^2$ for a compound corresponds in each case to one row of Table A.

Table 348
Compounds of the formula I-rr in which $R^{5a}$ is fluorine, $R^1$ is H and the combination of Y and $R^2$ for a compound corresponds in each case to one row of Table A.

Table 349
Compounds of the formula I-rr in which $R^{5a}$ is methyl, $R^1$ is H and the combination of Y and $R^2$ for a compound corresponds in each case to one row of Table A.

Table 350
Compounds of the formula I-rr in which $R^{5a}$ is $CF_3$, $R^1$ is H and the combination of Y and $R^2$ for a compound corresponds in each case to one row of Table A.

Table 351
Compounds of the formula I-ss in which $R^{5a}$ is chlorine, $R^1$ is H and the combination of Y and $R^2$ for a compound corresponds in each case to one row of Table A.

Table 352
Compounds of the formula I-ss in which $R^{5a}$ is bromine, $R^1$ is H and the combination of Y and $R^2$ for a compound corresponds in each case to one row of Table A.

Table 353
Compounds of the formula I-ss in which $R^{5a}$ is fluorine, $R^1$ is H and the combination of Y and $R^2$ for a compound corresponds in each case to one row of Table A.

Table 354
Compounds of the formula I-ss in which $R^{5a}$ is methyl, $R^1$ is H and the combination of Y and $R^2$ for a compound corresponds in each case to one row of Table A.

Table 355
Compounds of the formula I-ss in which $R^{5a}$ is $CF_3$, $R^1$ is H and the combination of Y and $R^2$ for a compound corresponds in each case to one row of Table A.

Table 356
Compounds of the formula I-tt in which $R^{5a}$ is chlorine, $R^1$ is H and the combination of Y and $R^2$ for a compound corresponds in each case to one row of Table A.

Table 357
Compounds of the formula I-tt in which $R^{5a}$ is bromine, $R^1$ is H and the combination of Y and $R^2$ for a compound corresponds in each case to one row of Table A.

Table 358
Compounds of the formula I-tt in which $R^{5a}$ is fluorine, $R^1$ is H and the combination of Y and $R^2$ for a compound corresponds in each case to one row of Table A.

Table 359
Compounds of the formula I-tt in which $R^{5a}$ is methyl, $R^1$ is H and the combination of Y and $R^2$ for a compound corresponds in each case to one row of Table A.

Table 360
Compounds of the formula I-tt in which $R^{5a}$ is $CF_3$, $R^1$ is H and the combination of Y and $R^2$ for a compound corresponds in each case to one row of Table A.

Table 361
Compounds of the formula I-uu in which $R^{5a}$ is chlorine, $R^1$ is H and the combination of Y and $R^2$ for a compound corresponds in each case to one row of Table A.

Table 362
Compounds of the formula I-uu in which $R^{5a}$ is bromine, $R^1$ is H and the combination of Y and $R^2$ for a compound corresponds in each case to one row of Table A.

Table 363
Compounds of the formula I-uu in which $R^{5a}$ is fluorine, $R^1$ is H and the combination of Y and $R^2$ for a compound corresponds in each case to one row of Table A.

Table 364
Compounds of the formula I-uu in which $R^{5a}$ is methyl, $R^1$ is H and the combination of Y and $R^2$ for a compound corresponds in each case to one row of Table A.

Table 365
Compounds of the formula I-uu in which $R^{5a}$ is $CF_3$, $R^1$ is H and the combination of Y and $R^2$ for a compound corresponds in each case to one row of Table A.

Table 366
Compounds of the formula I-vv in which $R^{5a}$ is chlorine, $R^1$ is H and the combination of Y and $R^2$ for a compound corresponds in each case to one row of Table A.

Table 367
Compounds of the formula I-vv in which $R^{5a}$ is bromine, $R^1$ is H and the combination of Y and $R^2$ for a compound corresponds in each case to one row of Table A.

Table 368
Compounds of the formula I-vv in which $R^{5a}$ is fluorine, $R^1$ is H and the combination of Y and $R^2$ for a compound corresponds in each case to one row of Table A.

Table 369
Compounds of the formula I-vv in which $R^{5a}$ is methyl, $R^1$ is H and the combination of Y and $R^2$ for a compound corresponds in each case to one row of Table A.

Table 370
Compounds of the formula I-vv in which $R^{5a}$ is $CF_3$, $R^1$ is H and the combination of Y and $R^2$ for a compound corresponds in each case to one row of Table A.

Table 371
Compounds of the formula I-ww in which $R^{5a}$ is chlorine, $R^1$ is H and the combination of Y and $R^2$ for a compound corresponds in each case to one row of Table A.

Table 372
Compounds of the formula I-ww in which $R^{5a}$ is bromine, $R^1$ is H and the combination of Y and $R^2$ for a compound corresponds in each case to one row of Table A.

Table 373
Compounds of the formula I-ww in which $R^{5a}$ is fluorine, $R^1$ is H and the combination of Y and $R^2$ for a compound corresponds in each case to one row of Table A.

Table 374
Compounds of the formula I-ww in which $R^{5a}$ is methyl, $R^1$ is H and the combination of Y and $R^2$ for a compound corresponds in each case to one row of Table A.

Table 375
Compounds of the formula I-ww in which $R^{5a}$ is $CF_3$, $R^1$ is H and the combination of Y and $R^2$ for a compound corresponds in each case to one row of Table A.

Table 376
Compounds of the formula I-xx in which $R^{5a}$ is chlorine, $R^1$ is H and the combination of Y and $R^2$ for a compound corresponds in each case to one row of Table A.

Table 377
Compounds of the formula I-xx in which $R^{5a}$ is bromine, $R^1$ is H and the combination of Y and $R^2$ for a compound corresponds in each case to one row of Table A.

Table 378
Compounds of the formula I-xx in which $R^{5a}$ is fluorine, $R^1$ is H and the combination of Y and $R^2$ for a compound corresponds in each case to one row of Table A.

Table 379
Compounds of the formula I-xx in which $R^{5a}$ is methyl, $R^1$ is H and the combination of Y and $R^2$ for a compound corresponds in each case to one row of Table A.

Table 380
Compounds of the formula I-xx in which $R^{5a}$ is $CF_3$, $R^1$ is H and the combination of Y and $R^2$ for a compound corresponds in each case to one row of Table A.

Table 381
Compounds of the formula I-yy in which $R^{5a}$ is chlorine, $R^1$ is H and the combination of Y and $R^2$ for a compound corresponds in each case to one row of Table A.

Table 382
Compounds of the formula I-yy in which $R^{5a}$ is bromine, $R^1$ is H and the combination of Y and $R^2$ for a compound corresponds in each case to one row of Table A.

Table 383
Compounds of the formula I-yy in which $R^{5a}$ is fluorine, $R^1$ is H and the combination of Y and $R^2$ for a compound corresponds in each case to one row of Table A.

Table 384
Compounds of the formula I-yy in which $R^{5a}$ is methyl, $R^1$ is H and the combination of Y and $R^2$ for a compound corresponds in each case to one row of Table A.

Table 385
Compounds of the formula I-yy in which $R^{5a}$ is $CF_3$, $R^1$ is H and the combination of Y and $R^2$ for a compound corresponds in each case to one row of Table A.

Table 386
Compounds of the formula I-zz in which $R^{5a}$ is chlorine, $R^1$ is H and the combination of Y and $R^2$ for a compound corresponds in each case to one row of Table A.

Table 387
Compounds of the formula I-zz in which $R^{5a}$ is bromine, $R^1$ is H and the combination of Y and $R^2$ for a compound corresponds in each case to one row of Table A.

Table 388
Compounds of the formula I-zz in which $R^{5a}$ is fluorine, $R^1$ is H and the combination of Y and $R^2$ for a compound corresponds in each case to one row of Table A.

Table 389
Compounds of the formula I-zz in which $R^{5a}$ is methyl, $R^1$ is H and the combination of Y and $R^2$ for a compound corresponds in each case to one row of Table A.

Table 390
Compounds of the formula I-zz in which $R^{5a}$ is $CF_3$, $R^1$ is H and the combination of Y and $R^2$ for a compound corresponds in each case to one row of Table A.

Tables 391 to 400
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is methyl instead of H.

Tables 401 to 410
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is $CF_3$ instead of H.

Tables 411 to 420
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is ethyl instead of H.

Tables 421 to 430
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is $CH_2CF_3$ instead of H.

Tables 431 to 440
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is n-propyl instead of H.

Tables 441 to 450
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is isopropyl instead of H.

Tables 451 to 460

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is n-butyl instead of H.

Tables 461 to 470

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is isobutyl instead of H.

Tables 471 to 480

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is tert-butyl instead of H.

Tables 481 to 490

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is CN instead of H.

Tables 491 to 500

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is methoxy instead of H.

Tables 501 to 510

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is methylcarbonyl instead of H.

Tables 511 to 520

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is phenyl instead of H.

Tables 521 to 530

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is 2-fluorophenyl instead of H.

Tables 531 to 540

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is 3-fluorophenyl instead of H.

Tables 541 to 550

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is 4-fluorophenyl instead of H.

Tables 551 to 560

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is 2-chlorophenyl instead of H.

Tables 561 to 570

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is 3-chlorophenyl instead of H.

Tables 571 to 580

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is 4-chlorophenyl instead of H.

Tables 581 to 590

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is cyclopropyl instead of H.

Tables 591 to 600

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is 3-bromophenyl instead of H.

Tables 601 to 610

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is 4-bromophenyl instead of H.

Tables 611 to 620

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is benzyl instead of H.

Tables 621 to 630

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is 2-phenylethyl instead of H.

Tables 631 to 640

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is $CH_2$-2-F—$C_6H_4$ instead of H.

Tables 641 to 650

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is $CH_2$-3-F—$C_6H_4$ instead of H.

Tables 651 to 660

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is $CH_2$-4-F—$C_6H_4$ instead of H.

Tables 661 to 670

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is $CH_2$-2-Cl—$C_6H_4$ instead of H.

Tables 671 to 680

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is $CH_2$-3-Cl—$C_6H_4$ instead of H.

Tables 681 to 690

Compounds of the formula I-a in which the combination of $R^{5a}$, $R^{5b}$ and $R^{5c}$ is as defined in any of Tables 1 to 10, the combination of Y and R² for a compound corresponds in each case to one row of Table A and R¹ is CH₂-4-Cl—C₆H₄ instead of H.

Tables 691 to 700

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂-cyclopropyl instead of H.

Tables 701 to 710

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂-3-Br—C₆H₄ instead of H.

Tables 711 to 720

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂-4-Br—C₆H₄ instead of H.

Tables 721 to 730

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂-2-MeO—C₆H₄ instead of H.

Tables 731 to 740

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂-3-MeO—C₆H₄ instead of H.

Tables 741 to 750

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂-4-MeO—C₆H₄ instead of H.

Tables 751 to 760

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-2-F—C₆H₄ instead of H.

Tables 761 to 770

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-3-F—C₆H₄ instead of H.

Tables 771 to 780

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-4-F—C₆H₄ instead of H.

Tables 781 to 790

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-2-Cl—C₆H₄ instead of H.

Tables 791 to 800

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-3-Cl—C₆H₄ instead of H.

Tables 801 to 810

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-4-Cl—C₆H₄ instead of H.

Tables 811 to 820

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-2-Br—C₆H₄ instead of H.

Tables 821 to 830

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-3-Br—C₆H₄ instead of H.

Tables 831 to 840

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-4-Br—C₆H₄ instead of H.

Tables 841 to 850

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-2-MeO—C₆H₄ instead of H.

Tables 851 to 860

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-3-MeO—C₆H₄ instead of H.

Tables 861 to 870

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is CH₂CH₂-4-MeO—C₆H₄ instead of H.

Tables 871 to 880

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is a ring A-1 instead of H.

Tables 881 to 890

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is a ring A-2 instead of H.

Tables 891 to 900

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is a ring A-3 instead of H.

Tables 901 to 910

Compounds of the formula I-a in which the combination of R⁵ᵃ, R⁵ᵇ and R⁵ᶜ is as defined in any of Tables 1 to 10, the combination of Y and R² for a compound corresponds in each case to one row of Table A and R¹ is a ring A-4 instead of H.

Tables 911 to 920

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-5 instead of H.

Tables 921 to 930

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-6 instead of H.

Tables 931 to 940

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-7 instead of H.

Tables 941 to 950

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-8 instead of H.

Tables 951 to 960

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-9 instead of H.

Tables 961 to 970

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-10 instead of H.

Tables 971 to 980

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-11 instead of H.

Tables 981 to 990

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-12 instead of H.

Tables 991 to 1000

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-13 instead of H.

Tables 1001 to 1010

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-14 instead of H.

Tables 1011 to 1020

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-15 instead of H.

Tables 1021 to 1030

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-16 instead of H.

Tables 1031 to 1040

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-17 instead of H.

Tables 1041 to 1050

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-18 instead of H.

Tables 1051 to 1060

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-19 instead of H.

Tables 1061 to 1070

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-20 instead of H.

Tables 1071 to 1080

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-21 instead of H.

Tables 1081 to 1090

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-22 instead of H.

Tables 1091 to 1100

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-23 instead of H.

Tables 1101 to 1110

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-24 instead of H.

Tables 1111 to 1120

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-25 instead of H.

Tables 1121 to 1130

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-26 instead of H.

Tables 1131 to 1140

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-27 instead of H.

Tables 1141 to 1150

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a ring A-28 instead of H.

Tables 1151 to 1160

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-1 instead of H.

Tables 1161 to 1170

Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-2 instead of H.

Tables 1171 to 1180
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-3 instead of H.

Tables 1181 to 1190
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-4 instead of H.

Tables 1191 to 1200
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-5 instead of H.

Tables 1201 to 1210
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-6 instead of H.

Tables 1211 to 1220
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-7 instead of H.

Tables 1221 to 1230
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-8 instead of H.

Tables 1231 to 1240
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-9 instead of H.

Tables 1241 to 1250
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-10 instead of H.

Tables 1251 to 1260
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-11 instead of H.

Tables 1261 to 1270
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-12 instead of H.

Tables 1271 to 1280
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-13 instead of H.

Tables 1281 to 1290
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-14 instead of H.

Tables 1291 to 1300
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-15 instead of H.

Tables 1301 to 1310
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-16 instead of H.

Tables 1311 to 1320
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-17 instead of H.

Tables 1321 to 1330
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-18 instead of H.

Tables 1331 to 1340
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-19 instead of H.

Tables 1341 to 1350
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-20 instead of H.

Tables 1351 to 1360
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-21 instead of H.

Tables 1361 to 1370
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-22 instead of H.

Tables 1371 to 1380
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-23 instead of H.

Tables 1381 to 1390
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-24 instead of H.

Tables 1391 to 1400
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-25 instead of H.

Tables 1401 to 1410
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-26 instead of H.

Tables 1411 to 1420
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-27 instead of H.

Tables 1421 to 1430
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2$-A-28 instead of H.

Tables 1431 to 1440
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-1 instead of H.

Tables 14441 to 1450
Compounds of the formula I-a in which the combination of $R^{5a}$, $R^{5b}$ and $R^{5c}$ is as defined in any of Tables 1 to 10, the combination of Y and $R^1$ for a compound corresponds in each case to one row of Table A and $R^1$ is a group $CH_2CH_2$-A-2 instead of H.

Tables 1451 to 1460
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-3 instead of H.

Tables 1461 to 1470
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-4 instead of H.

Tables 1471 to 1480
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-5 instead of H.

Tables 1481 to 1490
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-6 instead of H.

Tables 1491 to 1500
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-7 instead of H.

Tables 1501 to 1510
Compounds of the formula I-a in which the combination of $R^{5a}$, $R^{5b}$ and $R^{5c}$ is as defined in any of Tables 1 to 10, the combination of Y and $R^1$ for a compound corresponds in each case to one row of Table A and $R^1$ is a group $CH_2CH_2$-A-8 instead of H.

Tables 1511 to 1520
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-9 instead of H.

Tables 1521 to 1530
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-10 instead of H.

Tables 1531 to 1540
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-11 instead of H.

Tables 1541 to 1550
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-12 instead of H.

Tables 1551 to 1560
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-13 instead of H.

Tables 1561 to 1570
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-14 instead of H.

Tables 1571 to 1580
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-15 instead of H.

Tables 1581 to 1590
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-16 instead of H.

Tables 1591 to 1600
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-17 instead of H.

Tables 1601 to 1610
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-18 instead of H.

Tables 1611 to 1620
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-19 instead of H.

Tables 1621 to 1630
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-20 instead of H.

Tables 1631 to 1640
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-21 instead of H.

Tables 1641 to 1650
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-22 instead of H.

Tables 1651 to 1660
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-23 instead of H.

Tables 1661 to 1670
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-24 instead of H.

Tables 1671 to 1680
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-25 instead of H.

Tables 1681 to 1690
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-26 instead of H.

Tables 1691 to 1700
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-27 instead of H.

Tables 1701 to 1710
Compounds of the formula I-a in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is a group $CH_2CH_2$-A-28 instead of H.

Tables 1711 to 3030
Compounds of the formula I-b in which the combination of $R^{5a}$, $R^{5b}$ and $R^{5c}$ is as defined in any of Tables 11 to 20, the combination of Y and $R^2$ for a compound corresponds in each case to one row of Table A and $R^1$ is as defined in any of Tables 391 to 1710.

Tables 3031 to 4350
Compounds of the formula I-c in which the combination of $R^{5a}$, $R^{5b}$ and $R^{5c}$ is as defined in any of Tables 21 to 30, the combination of Y and $R^2$ for a compound corresponds in each case to one row of Table A and $R^1$ is as defined in any of Tables 391 to 1710.

Tables 4351 to 5670
Compounds of the formula I-d in which the combination of $R^{5a}$, $R^{5b}$ and $R^{5c}$ is as defined in any of Tables 31 to 40, the combination of Y and $R^2$ for a compound corresponds in each case to one row of Table A and $R^1$ is as defined in any of Tables 391 to 1710.

Tables 5671 to 6990
Compounds of the formula I-e in which the combination of $R^{5a}$, $R^{5b}$ and $R^{5c}$ is as defined in any of Tables 41 to 50, the combination of Y and $R^2$ for a compound corresponds in each case to one row of Table A and $R^1$ is as defined in any of Tables 391 to 1710.

Tables 6991 to 8310
Compounds of the formula I-f in which the combination of $R^{5a}$, $R^{5b}$ and $R^{5c}$ is as defined in any of Tables 51 to 60, the combination of Y and $R^2$ for a compound corresponds in each case to one row of Table A and $R^1$ is as defined in any of Tables 391 to 1710.

Tables 8311 to 9630
Compounds of the formula I-g in which the combination of $R^{5a}$, $R^{5b}$ and $R^{5c}$ is as defined in any of Tables 61 to 70, the combination of Y and $R^2$ for a compound corresponds in each case to one row of Table A and $R^1$ is as defined in any of Tables 391 to 1710.

Tables 9631 to 10950
Compounds of the formula I-h in which the combination of $R^{5a}$, $R^{5b}$ and $R^{5c}$ is as defined in any of Tables 71 to 80, the combination of Y and $R^2$ for a compound corresponds in each case to one row of Table A and $R^1$ is as defined in any of Tables 391 to 1710.

Tables 10951 to 12270
Compounds of the formula I-i in which the combination of $R^{5a}$, $R^{5b}$ and $R^{5c}$ is as defined in any of Tables 81 to 90, the combination of Y and $R^2$ for a compound corresponds in each case to one row of Table A and $R^1$ is as defined in any of Tables 391 to 1710.

Tables 12271 to 13590
Compounds of the formula I-j in which the combination of $R^{5a}$, $R^{5b}$ and $R^{5c}$ is as defined in any of Tables 91 to 100, the combination of Y and $R^2$ for a compound corresponds in each case to one row of Table A and $R^1$ is as defined in any of Tables 391 to 1710.

Tables 13591 to 14910
Compounds of the formula I-k in which the combination of $R^{5a}$, $R^{5b}$ and $R^{5c}$ is as defined in any of Tables 101 to 110, the combination of Y and $R^2$ for a compound corresponds in each case to one row of Table A and $R^1$ is as defined in any of Tables 391 to 1710.

Tables 14911 to 16230
Compounds of the formula I-l in which the combination of $R^{5a}$, $R^{5b}$ and $R^{5c}$ is as defined in any of Tables 111 to 120, the combination of Y and $R^2$ for a compound corresponds in each case to one row of Table A and $R^1$ is as defined in any of Tables 391 to 1710.

Tables 16231 to 17550
Compounds of the formula I-m in which the combination of $R^{5a}$, $R^{5b}$ and $R^{5c}$ is as defined in any of Tables 121 to 130, the combination of Y and $R^2$ for a compound corresponds in each case to one row of Table A and $R^1$ is as defined in any of Tables 391 to 1710.

Tables 17551 to 18870
Compounds of the formula I-n in which the combination of $R^{5a}$, $R^{5b}$ and $R^{5c}$ is as defined in any of Tables 131 to 140, the combination of Y and $R^2$ for a compound corresponds in each case to one row of Table A and $R^1$ is as defined in any of Tables 391 to 1710.

Tables 18871 to 20190
Compounds of the formula I-o in which the combination of $R^{5a}$, $R^{5b}$ and $R^{5c}$ is as defined in any of Tables 141 to 150, the combination of Y and $R^2$ for a compound corresponds in each case to one row of Table A and $R^1$ is as defined in any of Tables 391 to 1710.

Tables 20191 to 21510
Compounds of the formula I-p in which the combination of $R^{5a}$, $R^{5b}$ and $R^{5c}$ is as defined in any of Tables 151 to 160, the combination of Y and $R^2$ for a compound corresponds in each case to one row of Table A and $R^1$ is as defined in any of Tables 391 to 1710.

Tables 21511 to 22830
Compounds of the formula I-q in which the combination of $R^{5a}$, $R^{5b}$ and $R^{5c}$ is as defined in any of Tables 161 to 170, the combination of Y and $R^2$ for a compound corresponds in each case to one row of Table A and $R^1$ is as defined in any of Tables 391 to 1710.

Tables 22831 to 24150
Compounds of the formula I-r in which the combination of $R^{5a}$, $R^{5b}$ and $R^{5c}$ is as defined in any of Tables 171 to 180, the combination of Y and $R^2$ for a compound corresponds in each case to one row of Table A and $R^1$ is as defined in any of Tables 391 to 1710.

Tables 24151 to 25470
Compounds of the formula I-s in which the combination of $R^{5a}$, $R^{5b}$ and $R^{5c}$ is as defined in any of Tables 181 to 190, the combination of Y and $R^2$ for a compound corresponds in each case to one row of Table A and $R^1$ is as defined in any of Tables 391 to 1710.

Tables 25471 to 26790
Compounds of the formula I-t in which the combination of $R^{5a}$, $R^{5b}$ and $R^{5c}$ is as defined in any of Tables 191 to 200, the combination of Y and $R^2$ for a compound corresponds in each case to one row of Table A and $R^1$ is as defined in any of Tables 391 to 1710.

Tables 26791 to 28110
Compounds of the formula I-u in which the combination of $R^{5a}$, $R^{5b}$ and $R^{5c}$ is as defined in any of Tables 201 to 210, the combination of Y and $R^2$ for a compound corresponds in each case to one row of Table A and $R^1$ is as defined in any of Tables 391 to 1710.

Tables 28111 to 29430
Compounds of the formula I-v in which the combination of $R^{5a}$, $R^{5b}$ and $R^{5c}$ is as defined in any of Tables 211 to 220, the combination of Y and $R^2$ for a compound corresponds in each case to one row of Table A and $R^1$ is as defined in any of Tables 391 to 1710.

Tables 29431 to 30750
Compounds of the formula I-w in which the combination of $R^{5a}$, $R^{5b}$ and $R^{5c}$ is as defined in any of Tables 221 to 230, the combination of Y and $R^2$ for a compound corresponds in each case to one row of Table A and $R^1$ is as defined in any of Tables 391 to 1710.

Tables 30751 to 32070
Compounds of the formula I-x in which the combination of $R^{5a}$, $R^{5b}$ and $R^{5c}$ is as defined in any of Tables 231 to 240, the combination of Y and $R^2$ for a compound corresponds in each case to one row of Table A and $R^1$ is as defined in any of Tables 391 to 1710.

Tables 32071 to 33390
Compounds of the formula I-y in which the combination of $R^{5a}$, $R^{5b}$ and $R^{5c}$ is as defined in any of Tables 241 to 250, the combination of Y and $R^2$ for a compound corresponds in each case to one row of Table A and $R^1$ is as defined in any of Tables 391 to 1710.

Tables 33391 to 34710
Compounds of the formula I-z in which the combination of $R^{5a}$, $R^{5b}$ and $R^{5c}$ is as defined in any of Tables 251 to 260, the combination of Y and $R^2$ for a compound corresponds in each case to one row of Table A and $R^1$ is as defined in any of Tables 391 to 1710.

Tables 34711 to 34715
Compounds of the formula I-aa in which $R^{5a}$ is as defined in any of Tables 261 to 265, the combination of Y and $R^2$ for a compound corresponds in each case to one row of Table A and $R^1$ is methyl instead of H.

Tables 34716 to 34720
Compounds of the formula I-aa in which $R^{5a}$ is as defined in any of Tables 261 to 265, the combination of Y and $R^2$ for a compound corresponds in each case to one row of Table A and $R^1$ is $CF_3$ instead of H.

Tables 34721 to 34725
Compounds of the formula I-aa in which $R^{5a}$ is as defined in any of Tables 261 to 265, the combination of Y and $R^2$ for a compound corresponds in each case to one row of Table A and $R^1$ is ethyl instead of H.

Tables 34726 to 34730
Compounds of the formula I-aa in which $R^{5a}$ is as defined in any of Tables 261 to 265, the combination of Y and $R^2$ for a compound corresponds in each case to one row of Table A and $R^1$ is $CH_2CF_3$ instead of H.

Tables 34731 to 34735
Compounds of the formula I-aa in which $R^{5a}$ is as defined in any of Tables 261 to 265, the combination of Y and $R^2$ for a compound corresponds in each case to one row of Table A and $R^1$ is n-propyl instead of H.

Tables 34736 to 34740
Compounds of the formula I-aa in which $R^{5a}$ is as defined in any of Tables 261 to 265, the combination of Y and $R^2$ for a compound corresponds in each case to one row of Table A and $R^1$ is $CH_2CH_2CF_3$ instead of H.

Tables 34741 to 34745
Compounds of the formula I-aa in which $R^{5a}$ is as defined in any of Tables 261 to 265, the combination of Y and $R^2$ for a compound corresponds in each case to one row of Table A and $R^1$ is $CH_2CF_2CF_3$ instead of H.

Tables 34746 to 34750
Compounds of the formula I-aa in which $R^{5a}$ is as defined in any of Tables 261 to 265, the combination of Y and $R^2$ for a compound corresponds in each case to one row of Table A and $R^1$ is isopropyl instead of H.

Tables 34751 to 34755
Compounds of the formula I-aa in which $R^{5a}$ is as defined in any of Tables 261 to 265, the combination of Y and $R^2$ for a compound corresponds in each case to one row of Table A and $R^1$ is n-butyl instead of H.

Tables 34756 to 34760
Compounds of the formula I-aa in which $R^{5a}$ is as defined in any of Tables 261 to 265, the combination of Y and $R^2$ for a compound corresponds in each case to one row of Table A and $R^1$ is $(CH_2)_3CF_3$ instead of H.

Tables 34761 to 34765
Compounds of the formula I-aa in which $R^{5a}$ is as defined in any of Tables 261 to 265, the combination of Y and $R^2$ for a compound corresponds in each case to one row of Table A and $R^1$ is $CH_2$-cyclopropyl instead of H.

Tables 34766 to 34770
Compounds of the formula I-aa in which $R^{5a}$ is as defined in any of Tables 261 to 265, the combination of Y and $R^2$ for a compound corresponds in each case to one row of Table A and $R^1$ is $CH(CH_3)$-cyclopropyl instead of H.

Tables 34771 to 34775
Compounds of the formula I-aa in which $R^{5a}$ is as defined in any of Tables 261 to 265, the combination of Y and $R^2$ for a compound corresponds in each case to one row of Table A and $R^1$ is phenyl instead of H.

Tables 34776 to 34780
Compounds of the formula I-aa in which $R^{5a}$ is as defined in any of Tables 261 to 265, the combination of Y and $R^2$ for a compound corresponds in each case to one row of Table A and $R^1$ is 2-fluorophenyl instead of H.

Tables 34781 to 34785
Compounds of the formula I-aa in which $R^{5a}$ is as defined in any of Tables 261 to 265, the combination of Y and $R^2$ for a compound corresponds in each case to one row of Table A and $R^1$ is 3-fluorophenyl instead of H.

Tables 34786 to 34790
Compounds of the formula I-aa in which $R^{5a}$ is as defined in any of Tables 261 to 265, the combination of Y and $R^2$ for a compound corresponds in each case to one row of Table A and $R^1$ is 4-fluorophenyl instead of H.

Tables 34791 to 34795
Compounds of the formula I-aa in which $R^{5a}$ is as defined in any of Tables 261 to 265, the combination of Y and $R^2$ for a compound corresponds in each case to one row of Table A and $R^1$ is 2-chlorophenyl instead of H.

Tables 34796 to 34800
Compounds of the formula I-aa in which $R^{5a}$ is as defined in any of Tables 261 to 265, the combination of Y and $R^2$ for a compound corresponds in each case to one row of Table A and $R^1$ is 3-chlorophenyl instead of H.

Tables 34801 to 34805
Compounds of the formula I-aa in which $R^{5a}$ is as defined in any of Tables 261 to 265, the combination of Y and $R^2$ for a compound corresponds in each case to one row of Table A and $R^1$ is 4-chlorophenyl instead of H.

Tables 34806 to 34810
Compounds of the formula I-aa in which $R^{5a}$ is as defined in any of Tables 261 to 265, the combination of Y and $R^2$ for a compound corresponds in each case to one row of Table A and $R^1$ is 2-bromophenyl instead of H.

Tables 34811 to 34815
Compounds of the formula I-aa in which $R^{5a}$ is as defined in any of Tables 261 to 265, the combination of Y and $R^2$ for a compound corresponds in each case to one row of Table A and $R^1$ is 3-bromophenyl instead of H.

Tables 34816 to 34820
Compounds of the formula I-aa in which $R^{5a}$ is as defined in any of Tables 261 to 265, the combination of Y and $R^2$ for a compound corresponds in each case to one row of Table A and $R^1$ is 4-bromophenyl instead of H.

Tables 34821 to 34825
Compounds of the formula I-aa in which $R^{5a}$ is as defined in any of Tables 261 to 265, the combination of Y and $R^2$ for a compound corresponds in each case to one row of Table A and $R^1$ is benzyl instead of H.

Tables 34826 to 34830
Compounds of the formula I-aa in which $R^{5a}$ is as defined in any of Tables 261 to 265, the combination of Y and $R^2$ for a compound corresponds in each case to one row of Table A and $R^1$ is 2-phenylethyl instead of H.

Tables 34831 to 34835
Compounds of the formula I-aa in which $R^{5a}$ is as defined in any of Tables 261 to 265, the combination of Y and $R^2$ for a compound corresponds in each case to one row of Table A and $R^1$ is $CH_2$-2-F—$C_6H_4$ instead of H.

Tables 34836 to 34840
Compounds of the formula I-aa in which $R^{5a}$ is as defined in any of Tables 261 to 265, the combination of Y and $R^2$ for a compound corresponds in each case to one row of Table A and $R^1$ is $CH_2$-3-F—$C_6H_4$ instead of H.

Tables 34841 to 34845
Compounds of the formula I-aa in which $R^{5a}$ is as defined in any of Tables 261 to 265, the combination of Y and $R^2$ for a compound corresponds in each case to one row of Table A and $R^1$ is $CH_2$-4-F—$C_6H_4$ instead of H.

Tables 34846 to 34850
Compounds of the formula I-aa in which $R^{5a}$ is as defined in any of Tables 261 to 265, the combination of Y and $R^2$ for a compound corresponds in each case to one row of Table A and $R^1$ is $CH_2$-2-Cl—$C_6H_4$ instead of H.

Tables 34851 to 34855
Compounds of the formula I-aa in which $R^{5a}$ is as defined in any of Tables 261 to 265, the combination of Y and $R^2$ for a compound corresponds in each case to one row of Table A and $R^1$ is $CH_2$-3-Cl—$C_6H_4$ instead of H.

Tables 34856 to 34860
Compounds of the formula I-aa in which $R^{5a}$ is as defined in any of Tables 261 to 265, the combination of Y and $R^2$ for a compound corresponds in each case to one row of Table A and $R^1$ is $CH_2$-4-Cl—$C_6H_4$ instead of H.

Tables 34861 to 34865
Compounds of the formula I-aa in which $R^{5a}$ is as defined in any of Tables 261 to 265, the combination of Y and $R^2$ for a compound corresponds in each case to one row of Table A and $R^1$ is $CH_2$-2-Br—$C_6H_4$ instead of H.

Tables 348661 to 34870
Compounds of the formula I-aa in which $R^{5a}$ is as defined in any of Tables 261 to 265, the combination of Y and $R^2$ for a compound corresponds in each case to one row of Table A and $R^1$ is $CH_2$-3-Br—$C_6H_4$ instead of H.

Tables 34871 to 34875
Compounds of the formula I-aa in which $R^{5a}$ is as defined in any of Tables 261 to 265, the combination of Y and $R^2$ for a compound corresponds in each case to one row of Table A and $R^1$ is $CH_2$-4-Br—$C_6H_4$ instead of H.

Tables 34876 to 34880
Compounds of the formula I-aa in which $R^{5a}$ is as defined in any of Tables 261 to 265, the combination of Y and $R^2$ for a compound corresponds in each case to one row of Table A and $R^1$ is $CH_2$-2-MeO—$C_6H_4$ instead of H.

Tables 34881 to 34885
Compounds of the formula I-aa in which $R^{5a}$ is as defined in any of Tables 261 to 265, the combination of Y and $R^2$ for a compound corresponds in each case to one row of Table A and $R^1$ is $CH_2$-3-MeO—$C_6H_4$ instead of H.

Tables 34886 to 34890
Compounds of the formula I-aa in which $R^{5a}$ is as defined in any of Tables 261 to 265, the combination of Y and $R^2$ for a compound corresponds in each case to one row of Table A and $R^1$ is $CH_2$-4-MeO—$C_6H_4$ instead of H.

Tables 34891 to 34895
Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-2-F—$C_6H_4$ instead of H.

Tables 34896 to 34900

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-3-F—$C_6H_4$ instead of H.

Tables 34901 to 34905

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-4-F—$C_6H_4$ instead of H.

Tables 34906 to 34910

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-2-Cl—$C_6H_4$ instead of H.

Tables 34911 to 34915

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-3-Cl—$C_6H_4$ instead of H.

Tables 34916 to 34920

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-4-Cl—$C_6H_4$ instead of H.

Tables 34921 to 34925

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-2-Br—$C_6H_4$ instead of H.

Tables 34926 to 34930

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-3-Br—$C_6H_4$ instead of H.

Tables 34931 to 34935

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-4-Br—$C_6H_4$ instead of H.

Tables 34936 to 34940

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-2-MeO—$C_6H_4$ instead of H.

Tables 34941 to 34945

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-3-MeO—$C_6H_4$ instead of H.

Tables 34946 to 34950

Compounds of the formula I-aa in which $R^{5a}$ is as defined in any of Tables 261 to 265, the combination of Y and $R^2$ for a compound corresponds in each case to one row of Table A and $R^1$ is $CH_2CH_2$-4-MeO—$C_6H_4$ instead of H.

Tables 34951 to 34955

Compounds of the formula I-aa in which $R^{5a}$ is as defined in any of Tables 261 to 265, the combination of Y and $R^2$ for a compound corresponds in each case to one row of Table A and $R^1$ is a ring A-1 instead of H.

Tables 34956 to 34960

Compounds of the formula I-aa in which $R^{5a}$ is as defined in any of Tables 261 to 265, the combination of Y and $R^2$ for a compound corresponds in each case to one row of Table A and $R^1$ is a ring A-2 instead of H.

Tables 34961 to 34965

Compounds of the formula I-aa in which $R^{5a}$ is as defined in any of Tables 261 to 265, the combination of Y and $R^2$ for a compound corresponds in each case to one row of Table A and $R^1$ is a ring A-3 instead of H.

Tables 34966 to 34970

Compounds of the formula I-aa in which $R^{5a}$ is as defined in any of Tables 261 to 265, the combination of Y and $R^2$ for a compound corresponds in each case to one row of Table A and $R^1$ is a ring A-4 instead of H.

Tables 34971 to 34975

Compounds of the formula I-aa in which $R^{5a}$ is as defined in any of Tables 261 to 265, the combination of Y and $R^2$ for a compound corresponds in each case to one row of Table A and $R^1$ is a ring A-5 instead of H.

Tables 34976 to 34980

Compounds of the formula I-aa in which $R^{5a}$ is as defined in any of Tables 261 to 265, the combination of Y and $R^2$ for a compound corresponds in each case to one row of Table A and $R^1$ is a ring A-6 instead of H.

Tables 34981 to 34985

Compounds of the formula I-aa in which $R^{5a}$ is as defined in any of Tables 261 to 265, the combination of Y and $R^2$ for a compound corresponds in each case to one row of Table A and $R^1$ is a ring A-7 instead of H.

Tables 34986 to 34990

Compounds of the formula I-aa in which $R^{5a}$ is as defined in any of Tables 261 to 265, the combination of Y and $R^2$ for a compound corresponds in each case to one row of Table A and $R^1$ is a ring A-8 instead of H.

Tables 34991 to 34995

Compounds of the formula I-aa in which $R^{5a}$ is as defined in any of Tables 261 to 265, the combination of Y and $R^2$ for a compound corresponds in each case to one row of Table A and $R^1$ is a ring A-9 instead of H.

Tables 34996 to 35000

Compounds of the formula I-aa in which $R^{5a}$ is as defined in any of Tables 261 to 265, the combination of Y and $R^2$ for a compound corresponds in each case to one row of Table A and $R^1$ is a ring A-10 instead of H.

Tables 35001 to 35005

Compounds of the formula I-aa in which $R^{5a}$ is as defined in any of Tables 261 to 265, the combination of Y and $R^2$ for a compound corresponds in each case to one row of Table A and $R^1$ is a ring A-11 instead of H.

Tables 35006 to 35010

Compounds of the formula I-aa in which $R^{5a}$ is as defined in any of Tables 261 to 265, the combination of Y and $R^2$ for a compound corresponds in each case to one row of Table A and $R^1$ is a ring A-12 instead of H.

Tables 35011 to 35015

Compounds of the formula I-aa in which $R^{5a}$ is as defined in any of Tables 261 to 265, the combination of Y and $R^2$ for a compound corresponds in each case to one row of Table A and $R^1$ is a ring A-13 instead of H.

Tables 35016 to 35020

Compounds of the formula I-aa in which $R^{5a}$ is as defined in any of Tables 261 to 265, the combination of Y and $R^2$ for a compound corresponds in each case to one row of Table A and $R^1$ is a ring A-14 instead of H.

Tables 35021 to 35025

Compounds of the formula I-aa in which $R^{5a}$ is as defined in any of Tables 261 to 265, the combination of Y and $R^2$ for a compound corresponds in each case to one row of Table A and $R^1$ is a ring A-15 instead of H.

Tables 35026 to 35030

Compounds of the formula I-aa in which $R^{5a}$ is as defined in any of Tables 261 to 265, the combination of Y and $R^2$ for a compound corresponds in each case to one row of Table A and $R^1$ is a ring A-16 instead of H.

Tables 35031 to 35035

Compounds of the formula I-aa in which $R^{5a}$ is as defined in any of Tables 261 to 265, the combination of Y and $R^2$ for a compound corresponds in each case to one row of Table A and $R^1$ is a ring A-17 instead of H.

Tables 35036 to 35040

Compounds of the formula I-aa in which $R^{5a}$ is as defined in any of Tables 261 to 265, the combination of Y and $R^2$ for a compound corresponds in each case to one row of Table A and $R^1$ is a ring A-18 instead of H.

Tables 35041 to 35045

Compounds of the formula I-aa in which $R^{5a}$ is as defined in any of Tables 261 to 265, the combination of Y and $R^2$ for a compound corresponds in each case to one row of Table A and $R^1$ is a ring A-19 instead of H.

Tables 35046 to 35050

Compounds of the formula I-aa in which $R^{5a}$ is as defined in any of Tables 261 to 265, the combination of Y and $R^2$ for a compound corresponds in each case to one row of Table A and $R^1$ is a ring A-20 instead of H.

Tables 35051 to 35055

Compounds of the formula I-aa in which $R^{5a}$ is as defined in any of Tables 261 to 265, the combination of Y and $R^2$ for a compound corresponds in each case to one row of Table A and $R^1$ is a ring A-21 instead of H.

Tables 35056 to 35060

Compounds of the formula I-aa in which $R^{5a}$ is as defined in any of Tables 261 to 265, the combination of Y and $R^2$ for a compound corresponds in each case to one row of Table A and $R^1$ is a ring A-22 instead of H.

Tables 35061 to 35065

Compounds of the formula I-aa in which $R^{5a}$ is as defined in any of Tables 261 to 265, the combination of Y and $R^2$ for a compound corresponds in each case to one row of Table A and $R^1$ is a ring A-23 instead of H.

Tables 35066 to 35070

Compounds of the formula I-aa in which $R^{5a}$ is as defined in any of Tables 261 to 265, the combination of Y and $R^2$ for a compound corresponds in each case to one row of Table A and $R^1$ is a ring A-24 instead of H.

Tables 35071 to 35075

Compounds of the formula I-aa in which $R^{5a}$ is as defined in any of Tables 261 to 265, the combination of Y and $R^2$ for a compound corresponds in each case to one row of Table A and $R^1$ is a ring A-25 instead of H.

Tables 35076 to 35080

Compounds of the formula I-aa in which $R^{5a}$ is as defined in any of Tables 261 to 265, the combination of Y and $R^2$ for a compound corresponds in each case to one row of Table A and $R^1$ is a ring A-26 instead of H.

Tables 35081 to 35085

Compounds of the formula I-aa in which $R^{5a}$ is as defined in any of Tables 261 to 265, the combination of Y and $R^2$ for a compound corresponds in each case to one row of Table A and $R^1$ is a ring A-27 instead of H.

Tables 35086 to 35090

Compounds of the formula I-aa in which $R^{5a}$ is as defined in any of Tables 261 to 265, the combination of Y and $R^2$ for a compound corresponds in each case to one row of Table A and $R^1$ is a ring A-28 instead of H.

Tables 35091 to 35095

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-1 instead of H.

Tables 35096 to 35100

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-2 instead of H.

Tables 35101 to 35105

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-3 instead of H.

Tables 35106 to 35110

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-4 instead of H.

Tables 35111 to 35115

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-5 instead of H.

Tables 35116 to 35120

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-6 instead of H.

Tables 35121 to 35125

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-7 instead of H.

Tables 35126 to 35130

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-8 instead of H.

Tables 35131 to 35135

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-9 instead of H.

Tables 35136 to 35140

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-10 instead of H.

Tables 35141 to 35145

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-11 instead of H.

Tables 35146 to 35150

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-12 instead of H.

Tables 35151 to 35155

Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-13 instead of H.

Tables 35156 to 35160
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-14 instead of H.
Tables 35161 to 35165
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-15 instead of H.
Tables 35166 to 35170
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-16 instead of H.
Tables 35171 to 35175
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-17 instead of H.
Tables 35176 to 35180
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-18 instead of H.
Tables 35181 to 35185
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-19 instead of H.
Tables 35186 to 35190
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-20 instead of H.
Tables 35191 to 35195
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-21 instead of H.
Tables 35196 to 35200
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-22 instead of H.
Tables 35201 to 35205
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-23 instead of H.
Tables 35206 to 35210
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-24 instead of H.
Tables 35211 to 35215
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-25 instead of H.
Tables 35216 to 35220
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-26 instead of H.
Tables 35221 to 35225
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-27 instead of H.
Tables 35226 to 35230
Compounds of the formula I-aa in which $R^{5a}$ is as defined in any of Tables 261 to 265, the combination of Y and $R^2$ for a compound corresponds in each case to one row of Table A and $R^1$ is a group $CH_2$-A-28 instead of H.
Tables 35231 to 35235
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-1 instead of H.
Tables 35236 to 35240
Compounds of the formula I-aa in which $R^{5a}$ is as defined in any of Tables 261 to 265, the combination of Y and $R^1$ for a compound corresponds in each case to one row of Table A and $R^1$ is a group $CH_2CH_2$-A-2 instead of H.
Tables 35241 to 35245
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-3 instead of H.
Tables 35246 to 35250
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-4 instead of H.
Tables 35251 to 35255
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-5 instead of H.
Tables 35256 to 35260
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-6 instead of H.
Tables 35261 to 35265
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-7 instead of H.
Tables 35266 to 35270
Compounds of the formula I-aa in which $R^{5a}$ is as defined in any of Tables 261 to 265, the combination of Y and $R^1$ for a compound corresponds in each case to one row of Table A and $R^1$ is a group $CH_2CH_2$-A-8 instead of H.
Tables 35271 to 35275
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-9 instead of H.
Tables 35276 to 35280
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-10 instead of H.
Tables 35281 to 35285
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-11 instead of H.

Tables 35286 to 35290
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-12 instead of H.

Tables 35291 to 35295
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-13 instead of H.

Tables 35296 to 35300
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-14 instead of H.

Tables 35301 to 35305
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-15 instead of H.

Tables 35306 to 35310
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-16 instead of H.

Tables 35311 to 35315
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-17 instead of H.

Tables 35316 to 35320
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-18 instead of H.

Tables 35321 to 35325
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-19 instead of H.

Tables 35326 to 35330
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-20 instead of H.

Tables 35331 to 35335
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-21 instead of H.

Tables 35336 to 35340
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-22 instead of H.

Tables 35341 to 35345
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-23 instead of H.

Tables 35346 to 35350
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-24 instead of H.

Tables 35351 to 35355
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-25 instead of H.

Tables 35356 to 35360
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-26 instead of H.

Tables 35361 to 35365
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-27 instead of H.

Tables 35366 to 35370
Compounds of the formula I-aa in which $R^{5a}$ is as defined in any of Tables 261 to 265, the combination of Y and $R^2$ for a compound corresponds in each case to one row of Table A and $R^1$ is a group $CH_2CH_2$-A-28 instead of H.

Tables 35371 to 36030
Compounds of the formula I-bb in which $R^{5a}$ is as defined in any of Tables 266 to 270, the combination of Y and $R^2$ for a compound corresponds in each case to one row of Table A and $R^1$ is as defined in any of Tables 34711 to 35370.

Tables 36031 to 36690
Compounds of the formula I-cc in which $R^{5a}$ is as defined in any of Tables 271 to 275, the combination of Y and $R^2$ for a compound corresponds in each case to one row of Table A and $R^1$ is as defined in any of Tables 34711 to 35370.

Tables 36691 to 37350
Compounds of the formula I-dd in which $R^{5a}$ is as defined in any of Tables 276 to 280, the combination of Y and $R^2$ for a compound corresponds in each case to one row of Table A and $R^1$ is as defined in any of Tables 34711 to 35370.

Tables 37351 to 38010
Compounds of the formula I-ee in which $R^{5a}$ is as defined in any of Tables 281 to 285, the combination of Y and $R^2$ for a compound corresponds in each case to one row of Table A and $R^1$ is as defined in any of Tables 34711 to 35370.

Tables 38011 to 38670
Compounds of the formula I-ff in which $R^{5a}$ is as defined in any of Tables 286 to 290, the combination of Y and $R^2$ for a compound corresponds in each case to one row of Table A and $R^1$ is as defined in any of Tables 34711 to 35370.

Tables 38671 to 39330
Compounds of the formula I-gg in which $R^{5a}$ is as defined in any of Tables 291 to 295, the combination of Y and $R^2$ for a compound corresponds in each case to one row of Table A and $R^1$ is as defined in any of Tables 34711 to 35370.

Tables 39331 to 39990
Compounds of the formula I-hh in which $R^{5a}$ is as defined in any of Tables 296 to 300, the combination of Y and $R^2$ for a compound corresponds in each case to one row of Table A and $R^1$ is as defined in any of Tables 34711 to 35370.

Tables 39991 to 40650
Compounds of the formula I-ii in which $R^{5a}$ is as defined in any of Tables 301 to 305, the combination of Y and $R^2$ for a compound corresponds in each case to one row of Table A and $R^1$ is as defined in any of Tables 34711 to 35370.

Tables 40651 to 41310
Compounds of the formula I-jj in which $R^{5a}$ is as defined in any of Tables 306 to 310, the combination of Y and $R^2$ for a compound corresponds in each case to one row of Table A and $R^1$ is as defined in any of Tables 34711 to 35370.

Tables 41311 to 41970
Compounds of the formula I-kk in which $R^{5a}$ is as defined in any of Tables 311 to 315, the combination of Y and $R^2$ for a compound corresponds in each case to one row of Table A and $R^1$ is as defined in any of Tables 34711 to 35370.
Tables 41971 to 42630
Compounds of the formula I-ll in which $R^{5a}$ is as defined in any of Tables 316 to 320, the combination of Y and $R^2$ for a compound corresponds in each case to one row of Table A and $R^1$ is as defined in any of Tables 34711 to 35370.
Tables 42631 to 43290
Compounds of the formula I-mm in which $R^{5a}$ is as defined in any of Tables 321 to 325, the combination of Y and $R^2$ for a compound corresponds in each case to one row of Table A and $R^1$ is as defined in any of Tables 34711 to 35370.
Tables 43291 to 43950
Compounds of the formula I-nn in which $R^{5a}$ is as defined in any of Tables 326 to 330, the combination of Y and $R^2$ for a compound corresponds in each case to one row of Table A and $R^1$ is as defined in any of Tables 34711 to 35370.
Tables 43951 to 44610
Compounds of the formula I-oo in which $R^{5a}$ is as defined in any of Tables 331 to 335, the combination of Y and $R^2$ for a compound corresponds in each case to one row of Table A and $R^1$ is as defined in any of Tables 34711 to 35370.
Tables 44611 to 45270
Compounds of the formula I-pp in which $R^{5a}$ is as defined in any of Tables 336 to 340, the combination of Y and $R^2$ for a compound corresponds in each case to one row of Table A and $R^1$ is as defined in any of Tables 34711 to 35370.
Tables 45271 to 45930
Compounds of the formula I-qq in which $R^{5a}$ is as defined in any of Tables 341 to 345, the combination of Y and $R^2$ for a compound corresponds in each case to one row of Table A and $R^1$ is as defined in any of Tables 34711 to 35370.
Tables 45931 to 46590
Compounds of the formula I-rr in which $R^{5a}$ is as defined in any of Tables 346 to 350, the combination of Y and $R^2$ for a compound corresponds in each case to one row of Table A and $R^1$ is as defined in any of Tables 34711 to 35370.
Tables 46591 to 47250
Compounds of the formula I-ss in which $R^{5a}$ is as defined in any of Tables 351 to 355, the combination of Y and $R^2$ for a compound corresponds in each case to one row of Table A and $R^1$ is as defined in any of Tables 34711 to 35370.
Tables 47251 to 47910
Compounds of the formula I-tt in which $R^{5a}$ is as defined in any of Tables 356 to 360, the combination of Y and $R^2$ for a compound corresponds in each case to one row of Table A and $R^1$ is as defined in any of Tables 34711 to 35370.
Tables 47911 to 48570
Compounds of the formula I-uu in which $R^{5a}$ is as defined in any of Tables 361 to 365, the combination of Y and $R^2$ for a compound corresponds in each case to one row of Table A and $R^1$ is as defined in any of Tables 34711 to 35370.
Tables 48571 to 49230
Compounds of the formula I-vv in which $R^{5a}$ is as defined in any of Tables 366 to 370, the combination of Y and $R^2$ for a compound corresponds in each case to one row of Table A and $R^1$ is as defined in any of Tables 34711 to 35370.
Tables 49231 to 49890
Compounds of the formula I-ww in which $R^{5a}$ is as defined in any of Tables 371 to 375, the combination of Y and $R^2$ for a compound corresponds in each case to one row of Table A and $R^1$ is as defined in any of Tables 34711 to 35370.
Tables 49891 to 50550
Compounds of the formula I-xx in which $R^{5a}$ is as defined in any of Tables 376 to 380, the combination of Y and $R^2$ for a compound corresponds in each case to one row of Table A and $R^1$ is as defined in any of Tables 34711 to 35370.
Tables 50551 to 51210
Compounds of the formula I-yy in which $R^{5a}$ is as defined in any of Tables 381 to 385, the combination of Y and $R^2$ for a compound corresponds in each case to one row of Table A and $R^1$ is as defined in any of Tables 34711 to 35370.
Tables 51211 to 51870
Compounds of the formula I-zz in which $R^{5a}$ is as defined in any of Tables 386 to 390, the combination of Y and $R^2$ for a compound corresponds in each case to one row of Table A and $R^1$ is as defined in any of Tables 34711 to 35370.
Tables 51871 to 53190
Compounds of the formula I-α in which the combination of $R^{5a}$, $R^{5b}$ and $R^{5c}$ is as defined in any of Tables 1 to 10, the combination of Y and $R^2$ for a compound corresponds in each case to one row of Table A and $R^1$ is as defined in any of Tables 391 to 1710.
Tables 53190 to 53850
Compounds of the formula I-β in which $R^{5a}$ is as defined in any of Tables 261 to 265, the combination of Y and $R^2$ for a compound corresponds in each case to one row of Table A and $R^1$ is as defined in any of Tables 34711 to 35370.

Lengthy table referenced here

US08722673-20140513-T00001

Please refer to the end of the specification for access instructions.

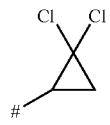

A-1

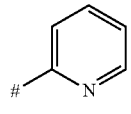

A-2

A-3

A-4

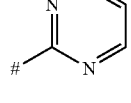

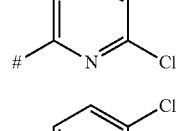

A-5

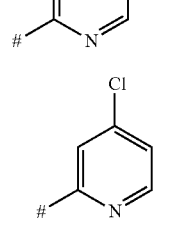

A-6

-continued
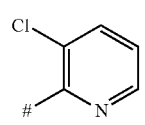 A-7
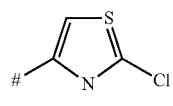 A-8
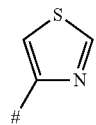 A-9
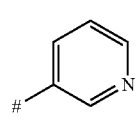 A-10
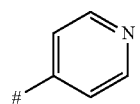 A-11
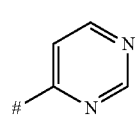 A-12
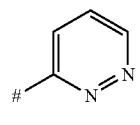 A-13
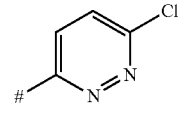 A-14
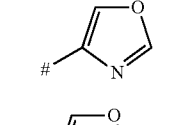 A-15
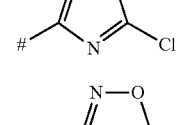 A-16
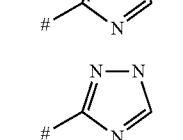 A-17
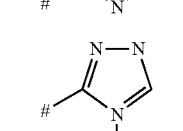 A-18
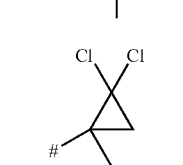 A-19
A-20
-continued
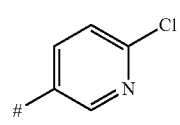 A-21
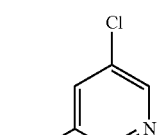 A-22
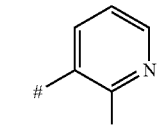 A-23
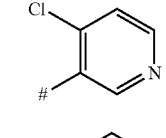 A-24
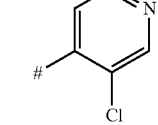 A-25
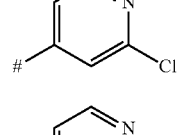 A-26
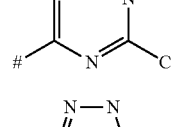 A-27
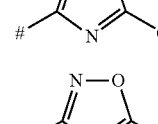 A-28
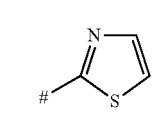 A-29
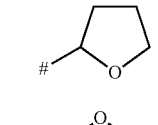 A-30
A-31
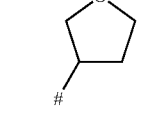 A-32
A-33

Among the above compounds I-a to I-zz and I-α, and I-β, compounds I-a and I-b and especially I-b are particularly preferred.

Compounds of formula I can be prepared by one or more of the following methods and variations as described in schemes 1 to 10. The variables $A^1, A^2, A^3, A^4, B^1, B^3, B^3, X, Y, R^1, R^2, R^4, R^5$, p and q are as defined above for formula I.

Compounds of formula I can be prepared by cycloaddition of styrene compounds of formula 2 with nitrile oxides derived from oximes of formula 3 as outlined in scheme 1. The reaction typically proceeds through the intermediacy of an in situ generated hydroxamic acid chloride by reaction with chlorine, hypochloride, N-succinimide, or chloramine-T. The hydroxamic acid chloride is combined with the oxime in the presence of the styrene 2. Depending on the conditions, amine bases such as pyridine or triethylamine may be necessary. The reaction can be run in a wide variety of solvents including DMF, toluene, dichloromethane, chlorobenzene, acetonitrile or the like.

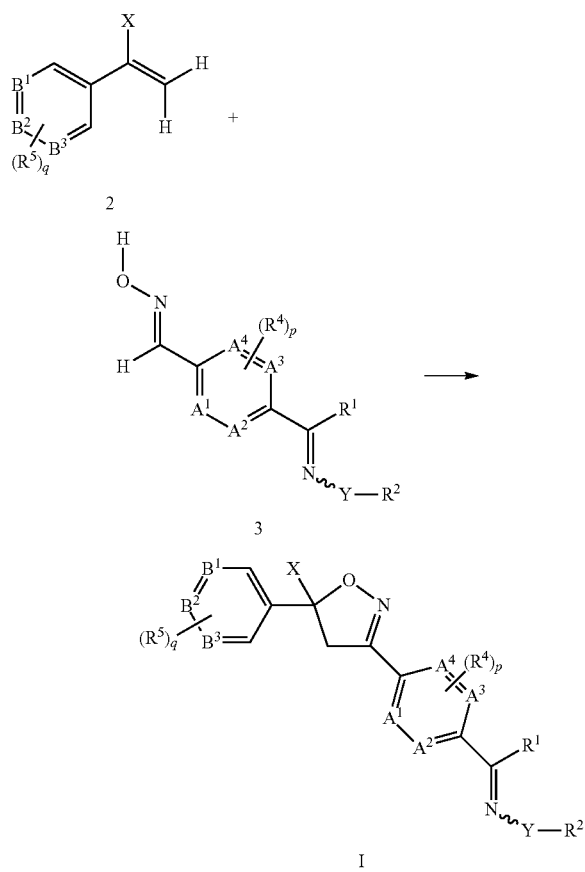

Scheme 1

Compounds of formula I can also be prepared as outlined in scheme 2 by reacting enones of formula 4 with hydroxylamine. The preparation of compounds of type 4 is, for example, described in WO 2007/074789.

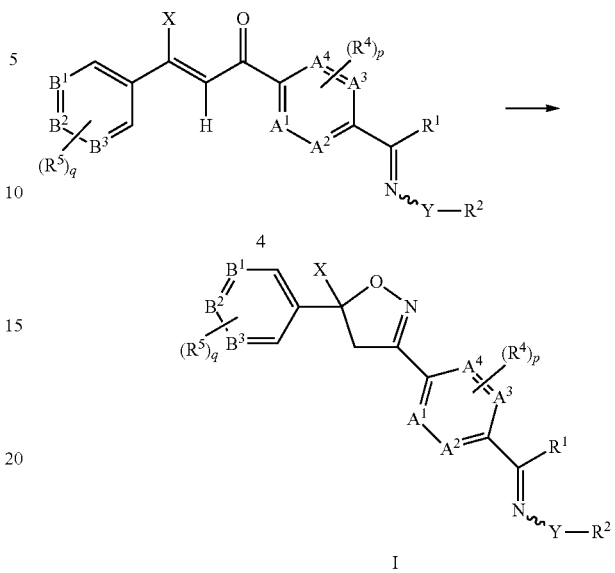

Scheme 2

Compounds of formula I can also be prepared as outlined in scheme 3 by reacting ketones or thioketones of formula 5 with hydroxylamine. The preparation of compounds of type 5 is, for example, described in WO 2007/074789.

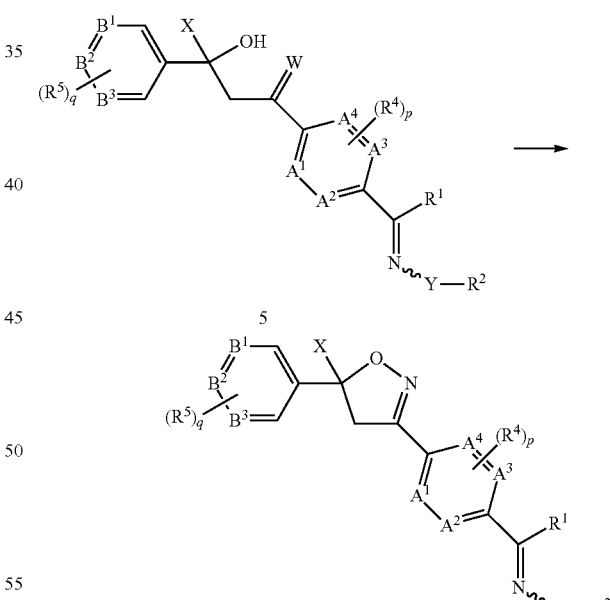

Scheme 3

Compounds of formula I can also be prepared as outlined in scheme 4 by condensation of an hydroxamic acid derivative 6 with a Grignard reagent or an organolithium compound as for example described by Reutrakul et al, e-EROS Encyclopedia of Reagents for Organic Synthesis, 2001, Wiley, Chichester, UK for the oximes and by Danko et al, Pest Management Science, 2006, 62, 229-236 for the hydrazones (Z may be a leaving group like halogen, OR" or SR"). The derived ketoxime 7 is then converted into compounds of formula I by reaction with an alkylating agent as for example described by Huang et al, J. Org. Chem. 2008, 73, 4017-4026.

Scheme 4

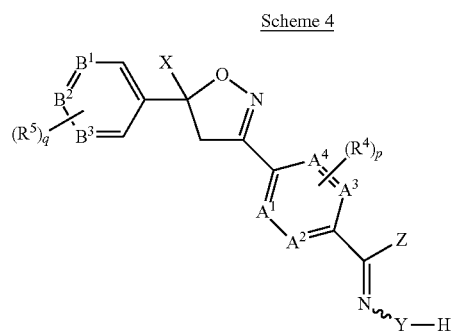

6

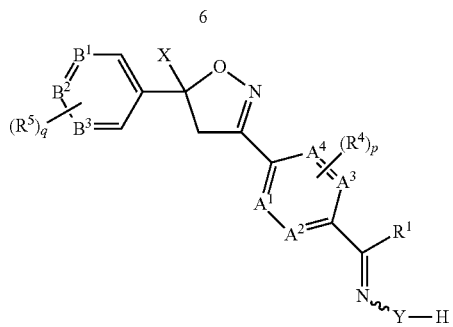

7

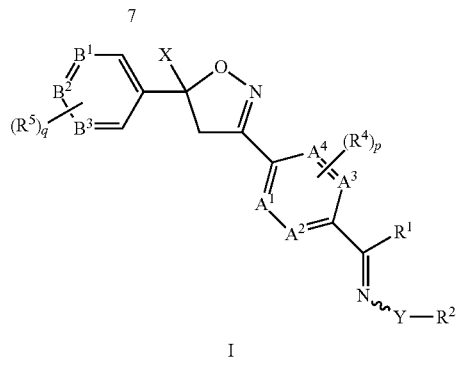

I

Compounds of formula I can also be prepared as outlined in scheme 5 by reaction of an hydrazone 8 with a formylating agent to yield hydrazone 9 as for example described by Brehme et al, Zeitschrift f. Chemie, 1968, 8, 226-227.

Scheme 5

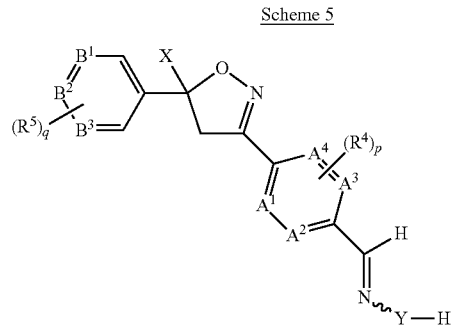

8

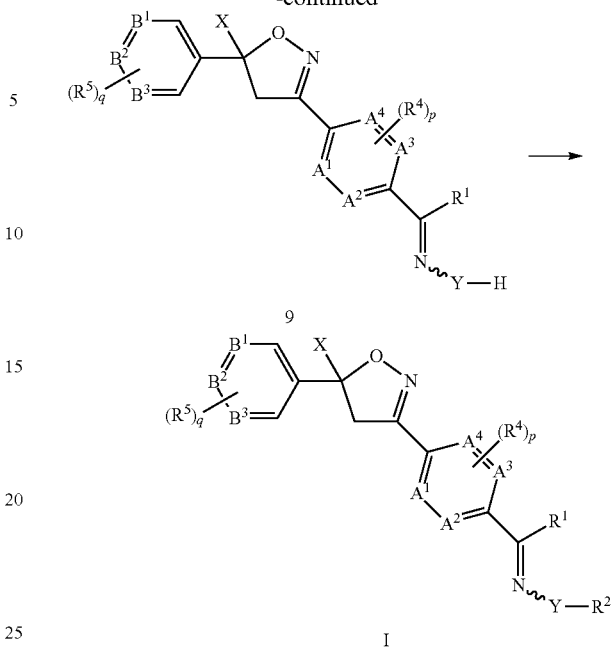

9

I

Compounds of formula I can also be prepared as outlined in scheme 6 by reaction of an aldehyde or ketone 10 with a hydroxylamine derivative as for example described by Stivers et al, WO 2006135763. Alternatively, compounds of formula 1 can also be prepared by reaction of an aldehyde or ketone 10 with a hydrazine derivative as for example described by Fattorusso et al, J. Med. Chem. 2008, 51, 1333-1343. Compounds of formula 10 can be prepared as described for example by Mihara et al, WO 2008/122375.

Scheme 6

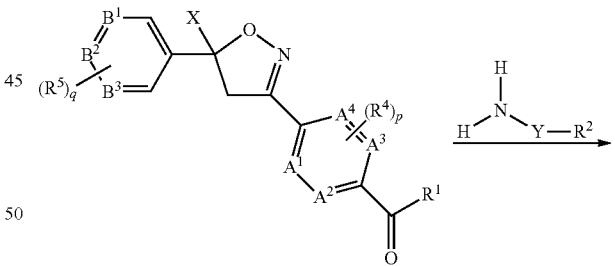

10

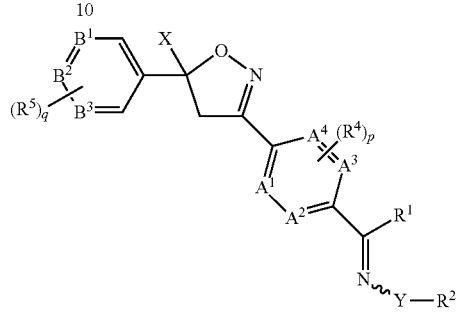

I

Compounds of formula I can also be prepared as outlined in scheme 7 by reaction of an organo lithium reagent or a Grignard reagent 11 with an electrophile as for example described by Fujisawa et al, Chem. Lett. 1983, 51, 1537-1540 for nitro compounds as electrophile or by Ziegler et al, WO 9520569 for hydroxamic acid derivatives. Hydrazone compounds of formula 1 can also be prepared as for example described by Benomar et al, J. Fluorine Chem. 1990, 50, 207-215 (J may be a metal, as for example Li, Na, K or MgX, SnX$_3$; Z may be a leaving group like halogen, OR" or SR")

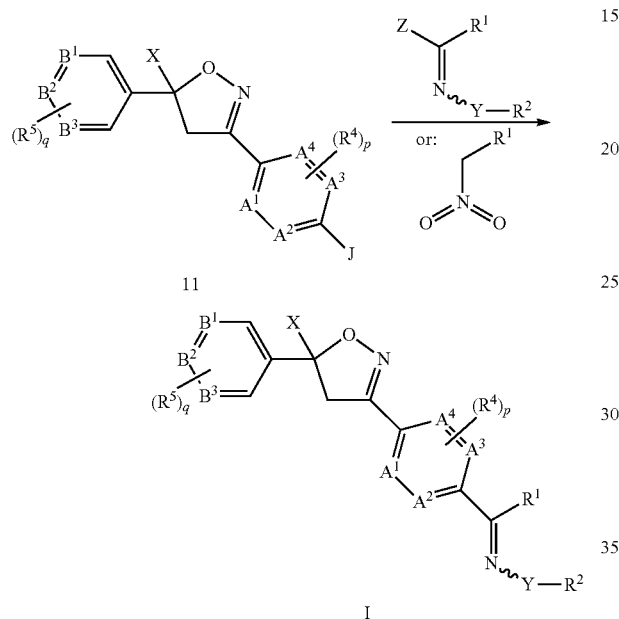

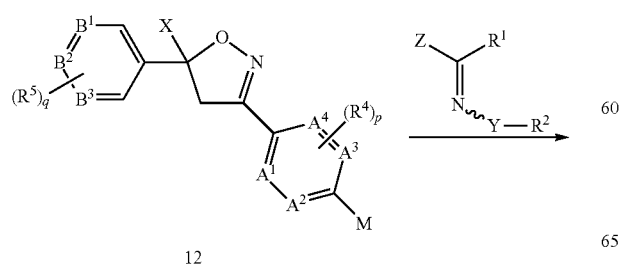

Compounds of formula I can also be prepared as outlined in scheme 8 by reaction of a boronic acid 12 with an electrophile (e.g. a hydroxamic acid chloride) as for example described by Dolliver et al, Can. J. Chem. 2007, 85, 913-922. (M is a boronic acid derivative; Z may be a leaving group like halogen, OR" or SR"). Compounds of formula 11 can be prepared as for example in WO 2005/085216.

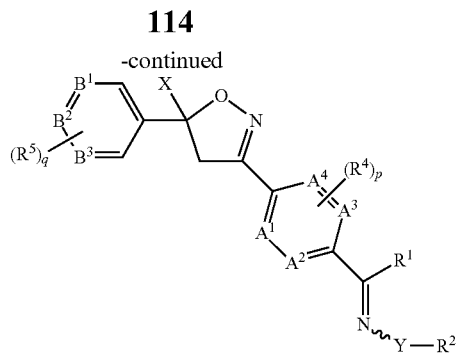

Compounds of formula I can also be prepared as outlined in scheme 9 by reaction of an olefin of formula 13 with a nitrite as for example described by Sugamoto et al, Synlett, 1998, 1270-1272.

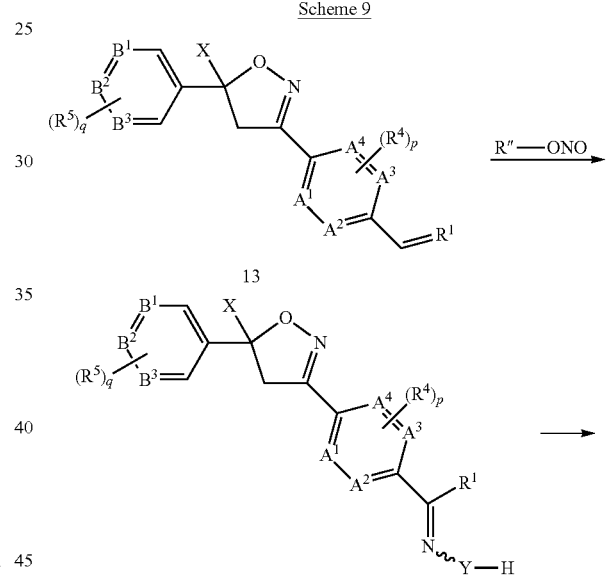

Compounds of formula 3 can be prepared as outlined in scheme 10 by reaction of an aldehyde of formula 15 with hydroxylamine as for example described in WO 2005085216. Compounds of formula 15 can be prepared by metalation of a halogenate of formula 14 (J may be a halogen as for example Cl, Br, I) and reaction with a formylation reagent, or alternatively, palladium catalyzed carbon monoxide insertion as for example described in WO 2005085216. Compounds of formula 14 can be prepared as for example described in WO 2005085216 for the oximes or as for example described by Liu et al, Bioorg. Med. Chem. Lett. 2008, 16, 1096-1102 for the hydrazones.

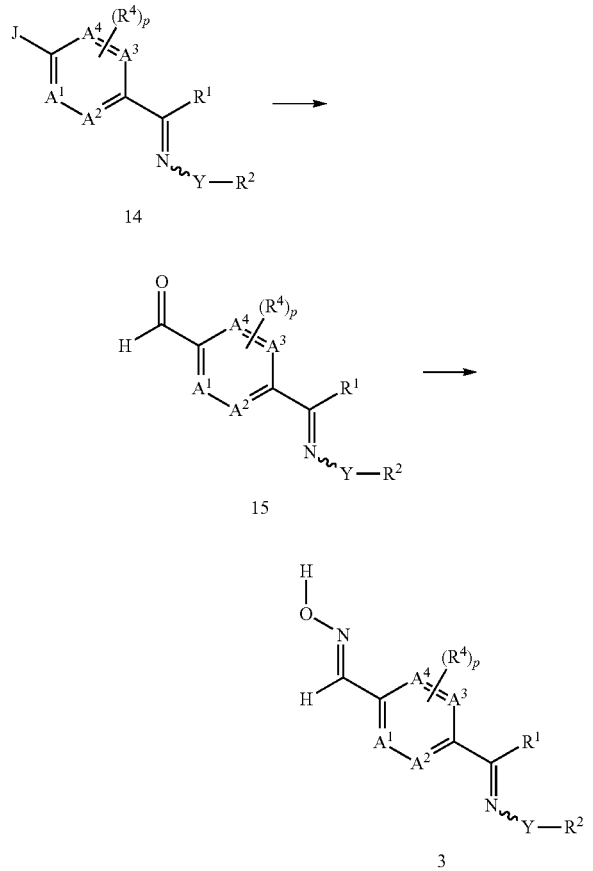

Scheme 10

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

The invention further relates to compounds of formula II which serve as intermediates in the synthesis of compounds I

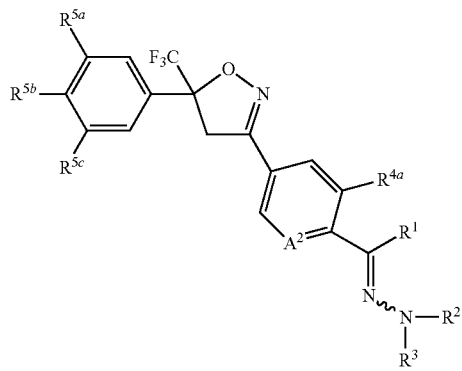

(II)

wherein $A^2$, $R^1$, $R^2$, $R^3$, $R^{4a}$, $R^{5a}$, $R^{5b}$ and $R^{5c}$ have one of the above general or in particular preferred meanings.

The invention further relates to compounds of formula III which also serve as intermediates in the synthesis of compounds I

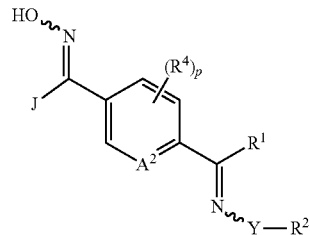

(III)

wherein
$A^2$, Y, $R^1$, $R^2$, $R^4$ and p have one of the above general or in particular preferred meanings; and
J is hydrogen or halogen.

Due to their excellent activity, the compounds of formula I may be used for controlling invertebrate pests.

Accordingly, the present invention also provides an agricultural composition comprising at least one compound of the formula I, as defined above, a stereoisomer thereof and/or at least one agriculturally acceptable salt thereof, and at least one inert liquid and/or solid agriculturally acceptable carrier.

The present invention also provides a veterinary composition comprising at least one compound of the formula I, as defined above, a stereoisomer thereof and/or at least one veterinarily acceptable salt thereof, and at least one inert liquid and/or solid veterinarily acceptable carrier.

Such compositions may contain a single active compound of formula I or a salt thereof or a mixture of several active compounds of formula I or their salts according to the present invention. The composition according to the present invention may comprise an individual isomer or mixtures of isomers as well as individual tautomers or mixtures of tautomers.

The present invention further relates to the use of a compound as defined above, of a stereoisomer and/or of an agriculturally or veterinarily acceptable salt thereof for combating invertebrate pests.

The present invention further relates to the use of a compound as defined above, of a stereoisomer and/or of a veterinarily acceptable salt thereof, for treating or protecting an animal from infestation or infection by invertebrate pests.

Moreover the present invention also provides a method for controlling invertebrate pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from invertebrate pest attack or infestation with a pesticidally effective amount of at least one imine compound of the formula I as defined above, a stereoisomer thereof and/or at least one agriculturally acceptable salt thereof.

Preferably, the method of the invention serves for protecting plants or plant propagation material (such as seed) and the plant which grows therefrom from animal pest attack or infestation and comprises treating the plants or the plant propagation material (such as seed) with a pesticidally effective amount of a compound of the formula I or an agriculturally acceptable salt thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

The invention furthermore relates to plant propagation material (such as seeds), comprising at least one compound of the formula I as defined above, a stereoisomer thereof and/or at least one agriculturally acceptable salt thereof.

The invention also provides a method for treating or protecting an animal from infestation or infection by invertebrate pests which comprises bringing the animal in contact with a pesticidally effective amount of at least one compound of the formula I as defined above, a stereoisomer thereof and/or at least one veterinarily acceptable salt thereof.

The compounds of the formula I and the pesticidical compositions comprising them are effective agents for controlling arthropod pests and nematodes. Invertebrate pests controlled by the compounds of formula I include for example:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocol-letis blancardella, Lobesia botrana, Loxostege sticticalis, Lymantria dispar, Lymantria monacha, Lyonetia clerkella, Malacosoma neustria, Mamestra brassicae, Orgyia pseu-dotsugata, Ostrinia nubilalis, Panolis flammea, Pectinophora gossypiella, Peridroma saucia, Phalera bucephala, Phthorimaea operculella, Phyllocnistis citrella, Pieris bras-sicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Mac-* rosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand, and Viteus vitifolii;

termites (Isoptera), e.g. Calotermes flavicollis, Leucotermes flavipes, Reticulitermes flavipes, Reticulitermes lucifugus and Termes natalensis;

orthopterans (Orthoptera), e.g. Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus;

Arachnoidea, such as arachnids (Acarina), e.g. of the families Argasidae, Ixodidae and Sarcoptidae, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei, and Eriophyidae spp. such as Aculus schlechtendali, Phyllocoptrata oleivora and Eriophyes sheldoni; Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetranychus pacificus, Tetranychus telarius and Tetranychus urticae, Panonychus ulmi, Panonychus citri, and oligonychus pratensis;

Siphonatera, e.g. Xenopsylla cheopsis, Ceratophyllus spp;

The compositions and compounds of formula I are useful for the control of nematodes, especially plant parasitic nematodes such as root knot nematodes, Meloidogyne hapla, Meloidogyne incognita, Meloidogyne javanica, and other Meloidogyne species;

cyst-forming nematodes, Globodera rostochiensis and other Globodera species; Heterodera avenae, Heterodera glycines, Heterodera schachtii, Heterodera trifolii, and other Heterodera species; Seed gall nematodes, Anguina species; Stem and foliar nematodes, Aphelenchoides species; Sting nematodes, Belonolaimus longicaudatus and other Belonolaimus species; Pine nematodes, Bursaphelenchus xylophilus and other Bursaphelenchus species; Ring nematodes, Criconema species, Criconemella species, Criconemoides species, Mesocriconema species; Stem and bulb nematodes, Ditylenchus destructor, Ditylenchus dipsaci and other Ditylenchus species; Awl nematodes, Dolichodorus species; Spiral nematodes, Heliocotylenchus multicinctus and other Heliocotylenchus species; Sheath and sheathoid nematodes, Hemicycliophora species and Hemicriconemoides species; Hirshmanniella species; Lance nematodes, Hoploaimus species; false rootknot nematodes, Nacobbus species; Needle nematodes, Longidorus elongatus and other Longidorus species; Pin nematodes, Paratylen-chus species; Lesion nematodes, Pratylenchus neglectus, Pratylenchus penetrans, Pratylenchus curvitatus, Pratylenchus goodeyi and other Pratylenchus species; Burrowing nematodes, Radopholus similis and other Radopholus species; Reniform nematodes, Rotylenchus robustus and other Rotylenchus species; Scutellonema species; Stubby root nematodes, Trichodorus primitivus and other Trichodorus species, Paratrichodorus species; Stunt nematodes, Tylenchorhynchus claytoni, Tylenchorhynchus dubius and other Tylenchorhynchus species; Citrus nematodes, Tylenchulus species; Dagger nematodes, Xiphinema species; and other plant parasitic nematode species.

In a preferred embodiment of the invention the compounds of formula I are used for controlling insects or arachnids, in particular insects of the orders Lepidoptera, Coleoptera, Thysanoptera and Homoptera and arachnids of the order Acarina. The compounds of the formula I according to the present invention are particularly useful for controlling insects of the order Thysanoptera and Homoptera.

The compounds of formula I or the pesticidal compositions comprising them may be used to protect growing plants and crops from attack or infestation by invertebrate pests, especially insects, acaridae or arachnids by contacting the plant/crop with a pesticidally effective amount of compounds of formula I. The term "crop" refers both to growing and harvested crops.

The compounds of formula I can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineers Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, anti-foaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compounds of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-dispersible granules and water-soluble granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formula I are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having preger-urinated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Other preferred FS formulations of compounds of formula I for seed treatment comprise from 0.5 to 80 wt % of the active ingredient, from 0.05 to 5 wt % of a wetter, from 0.5 to 15 wt % of a dispersing agent, from 0.1 to 5 wt % of a thickener, from 5 to 20 wt % of an anti-freeze agent, from 0.1 to 2 wt % of an anti-foam agent, from 1 to 20 wt % of a pigment and/or a dye, from 0 to 15 wt % of a sticker/adhesion agent, from 0 to 75 wt % of a filler/vehicle, and from 0.01 to 1 wt % of a preservative.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part).

For use against ants, termites, wasps, flies, mosquitos, crickets, or cockroaches, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethyl-formamide, N methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methyl-neodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the active compounds of formula I or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formula I into contact with each other, and "seed dressing" to methods of seed treatment which provide the seeds with an amount of the compounds of formula I, i.e. which generate a seed comprising the compound of formula I. In principle, the treatment can be applied to the seed at any time from the harvest of the seed to the sowing of the seed. The seed can be treated immediately before, or during, the planting of the seed, for example using the "planters box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formula I or veterinarily acceptable salts thereof are in particular also suitable for being used for combating parasites in and on animals.

A further object of the present invention is therefore to provide new methods for controlling parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or veterinarily acceptable salts thereof or a composition comprising it.

The present invention also provides a non-therapeutic method for treating, controlling, preventing and protecting animals against infestation and infection by parasites, which comprises applying to a locus a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises including a parasiticidally effective amount of a compound of formula I or the veterinarily acceptable salts thereof or a composition comprising it.

The invention relates further to the use of compounds of formula I for treating, controlling, preventing or protecting animals against infestation or infection by parasites. The invention relates also to the use of a compound of formula I, or a composition comprising it, for the manufacture of a medicament for the therapeutic treatment of animals against infections or infestations by parasites.

Activity of compounds against agricultural pests does not suggest their suitability for control of endo- and ectoparasites in and on animals which requires, for example, low, nonemetic dosages in the case of oral application, metabolic compatibility with the animal, low toxicity, and a safe handling.

Surprisingly, it has been found that compounds of formula I are suitable for combating endo- and ectoparasites in and on animals.

Compounds of formula I or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating endoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, bugs (Heteropterida): *Cimex lectularius, Cimex hemipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stepha-nurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*, Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp. a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and of the compositions containing them for combating ticks is a further preferred embodiment of the present invention.

The compounds of formula I also are especially useful for combating endoparasites (roundworms nematoda, thorny headed worms and planarians).

The compounds of formula I can be effective through both contact (via soil, glass, wall, bed net, carpet, blankets or animal parts) and ingestion (e.g. baits).

The present invention relates to the therapeutic and the non-therapeutic use of compounds of formula I for controlling and/or combating parasites in and/or on animals.

The compounds of formula I may be used to protect the animals from attack or infestation by parasites by contacting them with a parasitically effective amount of compounds of formula I. As such, "contacting" includes both direct contact (applying the compounds/compositions directly on the parasite, e.g. also at its locus, and optionally also administrating the compounds/composition directly on the animal) and indirect contact (applying the compounds/compositions to the locus of the parasite). The contact of the parasite through application to its locus is an example of a non-therapeutic use of compounds of formula I.

"Locus" as defined above means the habitat, food supply, breeding ground, area, material or environment in which a parasite is growing or may grow outside of the animal. The compounds of the invention can also be applied preventively to places at which occurrence of the pests or parasites is expected.

Administration to the animal can be carried out both prophylactically and therapeutically.

Administration of the active compounds is carried out directly or in the form of suitable preparations, orally, topically/dermally or parenterally.

For oral administration to warm-blooded animals, the compounds of formula I may be formulated as animal feeds, animal feed premixes, animal feed concentrates, pills, solutions, pastes, suspensions, drenches, gels, tablets, boluses and capsules. In addition, the compounds of formulae I may be administered to the animals in their drinking water. For oral administration, the dosage form chosen should provide the animal with 0.01 mg/kg to 100 mg/kg of animal body weight per day of the compounds of formula I, preferably with 0.5 mg/kg to 100 mg/kg of animal body weight per day.

Alternatively, the compounds of formula I may be administered to animals parenterally, for example, by intraruminal, intramuscular, intravenous or subcutaneous injection. The compounds of formula I may be dispersed or dissolved in a physiologically acceptable carrier for subcutaneous injection. Alternatively, the compounds of formula I may be formulated into an implant for subcutaneous administration. In addition the compounds of formula I may be transdermally administered to animals. For parenteral administration, the dosage form chosen should provide the animal with 0.01 mg/kg to 100 mg/kg of animal body weight per day of the compounds of formula I.

The compounds of formula I may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compounds of formula I. In addition, the compounds of formula I may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents are water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable Hydrophobic Phases (Oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable Emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compounds of formula I.

Generally, it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I are applied dermally/topically.

In a further preferred embodiment, the topical application is conducted in the form of compound-containing shaped articles such as collars, medallions, ear tags, bands for fixing at body parts, and adhesive strips and foils.

Generally, it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

Compositions to be used according to this invention may also contain other active ingredients, for example other pesticides, insecticides, herbicides, fungicides, other pesticides, or bactericides, fertilizers such as ammonium nitrate, urea, potash, and super-phosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formula I or the compositions comprising them in the use form as pesticides with other pesticides frequently results in a broader pesticidal spectrum of action.

The following list M of pesticides together with which the compounds according to the invention can be used and with which potential synergistic effects might be produced, is intended to illustrate the possible combinations, but not to impose any limitation:

M.1. Organo(thio)phosphates: acephate, azamethiphos, azinphos-ethyl, azinphosmethyl, chlorethoxyfos, chlorfenvinphos, chlormephos, chlorpyrifos, chlorpyrifosmethyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5, Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide; (R)-, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbannoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4) 4-[5-(3,5-Dichlorophenyl)-5-trifluoromethyl-4,5-dihydro-isoxazol-3-yl]-N-[(methoxyimino)methyl]-2-methyl-benzamide (M22.5), 4-[5-(3-Chloro-5-trifluoromethylphenyl)-5-trifluoromethyl-4,5-dihydro-isoxazol-3-yl]-2-methyl-N-[(2,2,2-trifluoroethyl-carbamoyl)-methyl]-benzamide (M22.6), 4-[5-(3-Chloro-5-trifluoromethylphenyl)-5-trifluoromethyl-4,5-dihydro-isoxazol-3-yl]-naphthalene-1-carboxylic acid [(2,2,2-trifluoroethylcarbamoyl)-methyl]-amide (M22.7) and 5-[5-(3,5-Dichloro-4-fluorophenyl)-5-trifluoromethyl-4,5-dihydro-isoxazol-3-yl]-2-[1,2,4]triazol-1-yl-benzonitrile (M22.8);

M.23. Anthranilamide compounds: chloranthraniliprole, cyantraniliprole,
5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1),
5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2),
5-Bromo-2-(3-chloro-pyridin-2-yl)-2H-pyrazole-3-carboxylic acid [2-bromo-4-cyano-6-(1-cyclopropyl-ethylcarbannoyl)-phenyl]-amide (M23.3),
5-Bromo-2-(3-chloro-pyridin-2-yl)-2H-pyrazole-3-carboxylic acid [2-bromo-4-chloro-6-(1-cyclopropyl-ethylcarbannoyl)-phenyl]-amide (M23.4),
5-Bromo-2-(3-chloro-pyridin-2-yl)-2H-pyrazole-3-carboxylic acid [2,4-dichloro-6-(1-cyclopropyl-ethylcarbannoyl)-phenyl]-amide (M23.5),
5-Bromo-2-(3-chloro-pyridin-2-yl)-2H-pyrazole-3-carboxylic acid [4-chloro-2-(1-cyclopropyl-ethylcarbannoyl)-6-methyl-phenyl]-amide (M23.6),
N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7),
N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8),
N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9),
N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10),
N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and
N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoropropyl)malononitrile ($CF_2H$—$CF_2$—$CF_2$—$CF_2$—$CH_2$—$C(CN)_2$—$CH_2$—$CH_2$—$CF_3$) (M24.1) and 2-(2,2,3,3,4,4,5,5-octafluoropentyl)-2-(3,3,4,4,4-pentafluorobutyl)-malonodinitrile ($CF_2H$—$CF_2$—$CF_2$—$CF_2$—$CH_2$—$C(CN)_2$—$CH_2$—$CH_2$—$CF_2$—$CF_3$) (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds:
4-{[(6-Bromopyrid-3-yl)methyl](2-fluoroethyl)amino}furan-2(5H)-on (M26.1),
4-{[(6-Fluoropyrid-3-yl)methyl](2,2-difluoroethyl)amino}furan-2(5H)-on (M26.2),
4-{[(2-Chloro1,3-thiazolo-5-yl)methyl](2-fluoroethyl)amino}furan-2(5H)-on (M26.3),
4-{[(6-Chloropyrid-3-yl)methyl](2-fluoroethyl)amino}furan-2(5H)-on (M26.4),
4-{[(6-Chloropyrid-3-yl)methyl](2,2-difluoroethyl)amino}furan-2(5H)-on (M26.5),
4-{[(6-Chloro-5-fluoropyrid-3-yl)methyl](methyl)amino}furan-2(5H)-on (M26.6),
4-{[(5,6-Dichloropyrid-3-yl)methyl](2-fluoroethyl)amino}furan-2(5H)-on (M26.7),
4-{[(6-Chloro-5-fluoropyrid-3-yl)methyl](cyclopropyl)amino}furan-2(5H)-on (M26.8),
4-{[(6-Chloropyrid-3-yl)methyl](cyclopropyl)amino}furan-2(5H)-on (M26.9) and
4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N-R-2,2-dihalo-1-R"cyclopropanecarboxamide-2-(2,6-dichloro-α,α,α-trifluoro-p-tolyl) hydrazone or N-R-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779. AKD 1022 and its preparation have been described in U.S. Pat. No. 6,300,348. The anthranilamides M23.1 to M23.6 have been described in WO 2008/72743 and WO 200872783, those M23.7 to M23.12 in WO2007/043677. The phthalamide M 21.1 is known from WO 2007/101540. The alkynylether compound M27.1 is described e.g. in JP 2006131529. Organic sulfur compounds have been described in WO 2007060839. The isoxazoline compounds M 22.1 to M 22.8 have been described in e.g. WO2005/085216, WO 2007/079162, WO 2007/026965, WO 2009/126668 and WO2009/051956. The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 02/089579, WO 02/090320, WO 02/090321, WO 04/006677, WO 05/068423, WO 05/068432 and WO 05/063694.

Fungicidal mixing partners are those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, fluoxastrobin, kresoxim-methyl, metominostrobin, orysastrobin, picoxystrobin or trifloxystrobin, sulfenic acid derivatives such as captafol, captan, dichlofluanid, folpet, tolylfluanid, cinnemamides and analogs such as dimethomorph, flumetover or flumorph.

The invertebrate pest, i.e. arthropodes and nematodes, the plant, soil or water in which the plant is growing can be contacted with the present compound(s) of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

Moreover, invertebrate pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

"Locus" means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formula I can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 25 g to 600 g per hectare, more desirably from 50 g to 500 g per hectare.

In the treatment of seed, the application rates of the active ingredients are generally from 0.1 g to 10 kg per 100 kg of seed, preferably from 1 g to 5 kg per 100 kg of seed, in particular from 1 g to 200 g per 100 kg of seed.

The present invention is now illustrated in further detail by the following examples.

I. PREPARATION EXAMPLES

Example 1

4-[5-(3,5-Dichloro-phenyl)-5-trifluoromethyl-4,5-dihydro-isoxazol-3-yl]-2-methyl-benzaldehyde oxime (Compound 1-1 of table C.1)

Step 1: Synthesis of 4-[5-(3,5-Dichloro-phenyl)-5-trifluoromethyl-4,5-dihydro-isoxazol-3-yl]-2-methyl-benzaldehyde A mixture of 3-(4-bromo-3-methyl-phenyl)-5-(3,5-dichloro-phenyl)-5-trifluoromethyl-4,5-dihydro-isoxazole (14.20 g, 31.34 mmol), triethyl silane (10.3 mL, 7.53 g, 62.8 mmol), sodium carbonate (5.43 g, 39.3 mmol), palladium bis(diphenylphosphine)-ferrocene dichloride $CH_2Cl_2$-complex (1.28 g, 1.57 mmol) and DMF (250 mL) were stirred under an atmosphere of carbon monoxide at 65° C. over night. After cooling to room temperature, the solvent was evaporated and the residue taken up in MTBE (methyl-tert-butyl ether), filtered and the filtrate was concentrated in vacuum. Purification of the residue on silica gel afforded the title compound (9.60 g, 76%).

HPLC-MS: 4.971 min, M=402.0.

Step 2: Synthesis of 4-[5-(3,5-Dichloro-phenyl)-5-trifluoromethyl-4,5-dihydro-isoxazol-3-yl]-2-methyl-benzaldehyde oxime A solution of 4-[5-(3,5-dichloro-phenyl)-5-trifluoromethyl-4,5-dihydro-isoxazol-3-yl]-2-methyl-benzaldehyde (i.e. the product of Step 1, 5.00 g), hydroxylamine hydrochloride (1.30 g) and concentrated hydrochloric acid (1 mL, 1.05 g) in MeOH (methanol) (37.5 mL) was stirred at 70° C. for 4 h. After cooling, the mixture was freed from all volatiles by evaporation and partitioned between MTBE and water. The organic layer was separated and dried. Chromatography over silica gel yielded the title compound (4.70 g, 91%).

HPLC-MS: 4.187 min, M=417.1.

$^1$H-NMR (400 MHz, $CDCl_3$): δ=2.44 (s, 3H), 2.90 (br. s, 1H), 3.81 (d, 1H), 4.15 (d, 1H), 7.47-7.58 (m, 4H), 7.80 (d, 1H), 8.35 (s, 1H), 11.10 (br. s, 1H) ppm.

Example 2

2-Chloro-4-[5-(3,5-dichloro-phenyl)-5-trifluoromethyl-4,5-dihydro-isoxazol-3-yl]-benzaldehyde oxime (Compound 5-1 of table C.5)

Step 1: Synthesis of 2-Chloro-4-[5-(3,5-dichloro-phenyl)-5-trifluoromethyl-4,5-dihydro-isoxazol-3-yl]-benzoic acid methyl ester A mixture of 3-(4-bromo-3-chloro-phenyl)-5-(3,5-dichloro-phenyl)-5-trifluoromethyl-4,5-dihydro-isoxazole (4.00 g), palladium bis(diphenylphosphine) dichloride $CH_2Cl_2$-complex (0.69 g), palladium acetate (0.14 g), sodium acetate (1.03 g), and methanol (50 mL) was placed in an autoclave, charged with 5 bar of carbon monoxide and stirred at 100° C. for 16 h. After cooling, the autoclave was opened and the reaction mixture was filtered. The filtrate was concentrated in vacuum and the residue was purified by flash chromatography on silica gel to obtain the title compound (2.2 g, 58%).

HPLC-MS: 4.285 min, M=451.95.

Step 2: Synthesis of 2-Chloro-4-[5-(3,5-dichloro-phenyl)-5-trifluoromethyl-4,5-dihydro-isoxazol-3-yl]-benzaldehyde To a solution of 2-chloro-4-[5-(3,5-dichloro-phenyl)-5-trifluoromethyl-4,5-dihydro-isoxazol-3-yl]-benzoic acid methyl ester (i.e. the product of Step 1, 2.20 g) in $CH_2Cl_2$ was added a solution of diisobutyl aluminium hydride (1 M in $CH_2Cl_2$, 10.7 mL) at −78° C. and kept at this temperature for 30 min. MeOH (25 mL) was added carefully and the mixture was allowed to warm to room temp, when aqueous K—Na-tartrate solution was added. The layers were separated and the aqueous phase was extracted with $CH_2Cl_2$, combined organic layers were washed with water, dried ($Na_2SO_4$) and evaporated. The residue was purified by flash chromatography on silica gel to obtain the title compound (1.35 g, 66%) and 2-chloro-4-[5-(3,5-dichloro-phenyl)-5-trifluoromethyl-4,5-dihydro-isoxazol-3-yl]-benzyl alcohol (0.49 g, 24%).

HPLC-MS: 4.238 min, M=421.85.

$^1$H-NMR (400 MHz, $CDCl_3$): δ=3.73 (d, 1H), 4.10 (d, 1H), 7.43 (m, 1H), 7.50 (s, 2H), 7.62 (d, 1H), 7.76 (s, 1H), 7.98 (d, 1H), 10.48 (s, 1H) ppm.

Step 3: Synthesis of 2-Chloro-4-[5-(3,5-dichloro-phenyl)-5-trifluoromethyl-4,5-dihydro-isoxazol-3-yl]-benzaldehyde oxime To a solution of 2-chloro-4-[5-(3,5-dichloro-phenyl)-5-trifluoromethyl-4,5-dihydro-isoxazol-3-yl]-benzaldehyde (i.e. the product of Step 2, 1.20 g) in methanol (5 mL) was added hydroxylamine hydrochloride (296 mg) and a catalytic amount of concentrated hydrochloric acid. The mixture was stirred at 70° C. for 3 h and concentrated in vacuum. Water was added and the mixture was extracted with ethyl acetate. Combined organic layers were dried ($Na_2SO_4$) and evaporated to obtain the title compound (1.2 g, 97%).

HPLC-MS: 4.090 min, M=436.95.

Example 3

4-[5-(3,5-Dichloro-phenyl)-5-trifluoromethyl-4,5-dihydro-isoxazol-3-yl]-2-methyl-benzaldehyde oxime-O-acetate (Compound 1-3 of table C.1)

To a solution of 4-[5-(3,5-dichloro-phenyl)-5-trifluoromethyl-4,5-dihydro-isoxazol-3-yl]-2-methyl-benzaldehyde oxime (i.e. the product of Step 2, Example 1, 200 mg) and triethylamine (73 μL, 53 mg) in THF (tetrahydrofuran) (10 mL) was added acetyl chloride (36 μL, 40 mg) via syringe at room temperature. The mixture was stirred over night, concentrated in vacuum and purified by flash chromatography on silica gel to yield the title compound (177 mg, 80%).

$^1$H-NMR (400 MHz, $CDCl_3$): δ=2.25 (s, 3H), 2.51 (s, 3H), 3.71 (d, 1H), 4.10 (d, 1H), 7.43 (m, 1H), 7.51 (m, 3H), 7.58 (d, 1H), 7.94 (d, 1H), 8.62 (s, 1H) ppm.

Example 4

4-[5-(3,5-Dichloro-phenyl)-5-trifluoromethyl-4,5-dihydro-isoxazol-3-yl]-2-methyl-benzaldehyde oxime-O-propionate (Compound 1-4 of table C.1)

To a solution of 4-[5-(3,5-dichloro-phenyl)-5-trifluoromethyl-4,5-dihydro-isoxazol-3-yl]-2-methyl-benzaldehyde oxime (i.e. the product of Step 2, Example 1, 200 mg) and triethylamine (73 μL, 53 mg) in THF (10 mL) was added propionyl chloride (44 μL, 47 mg) via syringe at room temperature. The mixture was stirred over night, concentrated in vacuum and purified by flash chromatography on silica gel to yield the title compound (80 mg, 37%).
$^1$H-NMR (400 MHz, CDCl$_3$): δ=1.26 (t, 3H), 2.45-2.59 (m, 5H), 3.70 (d, 1H), 4.10 (d, 1H), 7.43 (m, 1H), 7.51 (m, 3H), 7.59 (d, 1H), 7.93 (d, 1H), 8.61 (s, 1H) ppm.

Example 5

2-[1-{4-[5-(3,5-Dichloro-phenyl)-5-trifluoromethyl-4,5-dihydro-isoxazol-3-yl]-2-methyl-phenyl}-meth-(E)-ylideneaminooxy]-N-(2,2,2-trifluoro-ethyl)-acetamide (Compound 1-9 of table C.1)

Step 1: Synthesis of [1-{4-[5-(3,5-Dichloro-phenyl)-5-trifluoromethyl-4,5-dihydro-isoxazol-3-yl]-2-methyl-phenyl}-meth-(E)-ylideneaminooxy]-acetic acid tert-butyl ester (Compound 1-13 of table C.1)

A mixture of 4-[5-(3,5-dichloro-phenyl)-5-trifluoromethyl-4,5-dihydro-isoxazol-3-yl]-2-methyl-benzaldehyde (i.e. the product of Step 1, Example 1, 1.00 g), amino-oxy-acetic-acid-tert-butyl-ester (403 mg), p-toluene sulfonic acid (43 mg) and toluene (20 mL) were heated to reflux for 30 min. After cooling, the mixture was washed with water, and the organic layer was dried over Na$_2$SO$_4$. After evaporation the residue was purified by flash chromatography on silica gel to yield the title compound (745 mg, 56%)
HPLC-MS: 4.873 min, m/z=531.05.
$^1$H-NMR (400 MHz, CDCl$_3$): δ=1.50 (s, 9H), 2.44 (s, 3H), 3.69 (d, 1H), 4.09 (d, 1H), 7.42 (m, 1H), 7.44-7.53 (m, 4H), 7.74 (d, 1H), 8.44 (s, 1H) ppm.

Step 2: Synthesis of [1-{4-[5-(3,5-Dichloro-phenyl)-5-trifluoromethyl-4,5-dihydro-isoxazol-3-yl]-2-methyl-phenyl}-meth-(E)-ylideneaminooxy]-acetic acid (Compound I-12 of table C.1)

A solution of [1-{4-[5-(3,5-dichloro-phenyl)-5-trifluoromethyl-4,5-dihydro-isoxazol-3-yl]-2-methyl-phenyl}-meth-(E)-ylideneaminooxy]-acetic acid tert-butyl ester (i.e the product of Step 1, 531 mg) in CH$_2$Cl$_2$ (20 mL) was treated with formic acid (0.25 mL, 0.30 g) and stirred at room temperature over night. Trifluoroacetic acid (0.50 g) was added and the mixture stirred until tlc (thin layer chromatography) indicated completion of the reaction. The organic layer was washed with water three times, dried (Na$_2$SO$_4$) and evaporated to give the title compound (502 mg, 80%) that was used in the next step without further purification. NMR indicated the absence of the tert butyl ester.

Step 3: Synthesis of 2-[1-{4-[5-(3,5-Dichloro-phenyl)-5-trifluoromethyl-4,5-dihydro-isoxazol-3-yl]-2-methyl-phenyl}-meth-(E)-ylideneaminooxy]-N-(2,2,2-trifluoroethyl)-acetamide To a solution of [1-{4-[5-(3,5-dichloro-phenyl)-5-trifluoromethyl-4,5-dihydro-isoxazol-3-yl]-2-methyl-phenyl}-meth-(E)-ylideneaminooxy]-acetic acid (i.e. the product of Step 2, 200 mg) in CH$_2$Cl$_2$ (12 mL) was added 1-(3-dimethylaminopropyl)-3-ethyl carbodiimide hydrochloride (130 mg). After 15 min, 2,2,2-trifluoroethyl amine (64 μL, 80 mg) and N,N-4-dimethylaminopyridine (80 mg) was added and the mixture was stirred at room temperature over night. After concentration in vacuum, the residue was purified by flash chromatography on silica gel to obtain the title compound (100 mg, 43%).
HPLC-MS: 4.328, m/z=556.05.
$^1$H-NMR (400 MHz, CDCl$_3$): δ=2.44 (s, 3H), 3.69 (d, 1H), 4.01 (m, 2H), 4.10 (d, 1H), 6.61 (br t, 1H), 7.42 (m, 1H), 7.44-7.58 (m, 4H), 7.73 (d, 1H), 8.46 (s, 1H) ppm.

Example 6

1-{4-[5-(3,5-Dichloro-phenyl)-5-trifluoromethyl-4,5-dihydro-isoxazol-3-yl]-2-methyl-phenyl}-ethanone oxime (Compound 1-17 of table C.1)

Step 1: Synthesis of 1-{4-[5-(3,5-Dichloro-phenyl)-5-trifluoromethyl-4,5-dihydro-isoxazol-3-yl]-2-methyl-phenyl}-ethanone A mixture of 3-(4-bromo-3-methyl-phenyl)-5-(3,5-dichloro-phenyl)-5-trifluoromethyl-4,5-dihydro-isoxazole (500 mg), 1,4-butandiol-monovinyl-ether (385 mg), palladium on charcoal (10%, 23 mg), 1,3-bis(diphenylphosphino) propane (259 mg) and n-butanol (3 mL) were refluxed over night. Ethyl acetate (30 mL) and aqueous acetic acid (1 M, 20 mL) were added, and left at room temperature for 1 h. After separation of the layers, the organic layer was washed with HCl (1 M, 10 mL), dried (Na$_2$SO$_4$) and concentrated in vacuum. The residue was purified by flash chromatography on silica gel to yield the title compound (270 mg, 60%).
HPLC-MS: 4.224, m/z=415.60.
$^1$H-NMR (500 MHz, CDCl$_3$): δ=2.54 (s, 3H), 2.60 (s, 3H), 3.70 (d, 1H), 4.11 (d, 1H), 7.41 (m, 1H), 7.51 (m, 3H), 7.59 (m, 1H), 7.73 (s, 1H) ppm.

Step 2: Synthesis of 1-{4-[5-(3,5-Dichloro-phenyl)-5-trifluoromethyl-4,5-dihydro-isoxazol-3-yl]-2-methyl-phenyl}-ethanone oxime To a solution of 1-{4-[5-(3,5-Dichloro-phenyl)-5-trifluoromethyl-4,5-dihydro-isoxazol-3-yl]-2-methyl-phenyl}-ethanone (i.e the product of Step 1, 250 mg) in methanol (10 mL) was added acetic acid (1 drop) and hydroxylamine hydrochloride (44 mg) and the mixture was stirred at room temperature over night. After concentration in vacuum, the residue was taken up in ethyl acetate and washed with water. The organic layer was separated, dried (Na$_2$SO$_4$) and concentrated in vacuum. The residue was purified by flash chromatography on silica gel to yield the title compound (37 mg, 14%).
HPLC-MS: 4.191, m/z=431.05

Example 7

4-[5-(3,5-Dichloro-phenyl)-5-trifluoromethyl-4,5-dihydro-isoxazol-3-yl]-N-hydroxy-2-methyl-benzimidic acid methyl ester (Compounds 1-30 and 1-31 of table C.1)

Step 1: Synthesis of 4-[5-(3,5-Dichloro-phenyl)-5-trifluoromethyl-4,5-dihydro-isoxazol-3-I]-2-methyl-benzoic acid methyl ester A mixture of 3-(4-bromo-3-methyl-phenyl)-5-(3,5-dichloro-phenyl)-5-trifluoromethyl-4,5-dihydro-isoxazole (5.00 g), palladium bis(diphenylphosphine) dichloride $CH_2Cl_2$-complex (0.80 g), palladium acetate (0.20 g), sodium acetate (1.35 g), and methanol (50 mL) was placed in an autoclave, charged with 5 bar of carbon monoxide and stirred at 100° C. for 16 h. After cooling, the autoclave was opened and the reaction mixture was filtered. The filtrate was concentrated in vacuum and the residue was purified by flash chromatography on silica gel to obtain the title compound (3.46 g, 73%).

HPLC-MS: 4.523 min, M=432.05.

Step 2: Synthesis of 4-[5-(3,5-Dichloro-phenyl)-5-trifluoromethyl-4,5-dihydro-isoxazol-3-yl]-2-methyl-thiobenzoic acid O-methyl ester A solution of 4-[5-(3,5-dichloro-phenyl)-5-trifluoromethyl-4,5-dihydro-isoxazol-3-I]-2-methyl-benzoic acid methyl ester (i.e. the product of Step 1, 3.40 g) and P4510 (3.497 g) in xylenes (100 mL) was heated to reflux for 16 h. Then P4510 (1 g) was added and heated for another 4 h. After cooling, the mixture was concentrated in vacuum and the residue was purified by flash chromatography on silica gel to provide the title compound (3.28 g, 93%).

HPLC-MS: 4.770 min, M=447.95.

Step 3: Synthesis of 4-[5-(3,5-Dichloro-phenyl)-5-trifluoromethyl-4,5-dihydro-isoxazol-3-yl]-N-hydroxy-2-methyl-benzimidic acid methyl ester To a solution of 4-[5-(3,5-dichloro-phenyl)-5-trifluoromethyl-4,5-dihydro-isoxazol-3-yl]-2-methyl-thiobenzoic acid O-methyl ester (i.e. the product of Step 2, 300 mg) in ethanol (10 mL) was added hydroxylammonium chloride (51 mg) and triethyl amine (0.23 mL, 0.17 g) and stirred at room temperature over night. Water was added and the mixture was extracted with $CH_2Cl_2$ three times. Combined organic layers were dried ($Na_2SO_4$) and concentrated in vacuum. The residue was purified by flash chromatography on silica gel to yield the title compounds (94 mg of 1-30 and 124 mg of 1-31, together 73%).

Isomer 1-30:

HPLC-MS: 4.163, m/z=447.05.

$^1$H-NMR (400 MHz, $CDCl_3$): δ=2.35 (s, 3H), 3.69 (d, 1H), 3.87 (s, 3H), 4.08 (d, 1H), 7.33 (d, 1H), 7.42 (m, 1H), 7.50-7.60 (m, 4H) ppm.

Isomer 1-31:

HPLC-MS: 3.901, m/z=447.05.

$^1$H-NMR (400 MHz, $CDCl_3$): δ=2.63 (s, 3H), 3.71 (d, 1H), 3.92 (s, 3H), 4.10 (d, 1H), 7.44 (m, 1H), 7.50-7.58 (m, 4H), 7.97 (d, 1H) ppm.

Example 8

Pyridine-2-carboxylic acid [1-{4-[5-(3,5-dichloro-phenyl)-5-trifluoromethyl-4,5-dihydro-isoxazol-3-yl]-2-methyl-phenyl}-meth-(E)-ylidene]-hydrazide (Compound 1-45 of table C.1)

A solution of 4-[5-(3,5-dichloro-phenyl)-5-trifluoromethyl-4,5-dihydro-isoxazol-3-yl]-2-methyl-benzaldehyde (i.e. the product of Step 1, 500 mg), concentrated hydrochloric acid (5 drops) and 2-picolyl hydrazine (188 mg) in methanol (20 mL) were heated at reflux for 5 h. The mixture was concentrated and the residue was triturated with water. Filtration yielded the title compound (289 mg, 45%).

HPLC-MS: 4.104, m/z=521.00.

Example 9

1-{4-[5-(3,5-Dichloro-phenyl)-5-trifluoromethyl-4,5-dihydro-isoxazol-3-yl]-2-methyl-phenyl}-3-methyl-butan-1-one oxime (Compound 1-55 of table C.1)

Step 1: Synthesis of 1-{4-[5-(3,5-Dichloro-phenyl)-5-trifluoromethyl-4,5-dihydro-isoxazol-3-yl]-2-methyl-phenyl}-3-methyl-butan-1-ol To a solution of 3-(4-bromo-3-methyl-phenyl)-5-(3,5-dichloro-phenyl)-5-trifluoromethyl-4,5-dihydro-isoxazole (500 mg) in ether (20 mL) was added tert-butyllithium (1.5 mL of a 1.6 M solution in pentane) at −78° C. After 10 min at this temperature, $MgBr_2$ (0.15 M in THF, 10.3 mL) was added dropwise and left for another 15 min. Valeraldehyde (141 μL, 114 mg) was added and the mixture was stirred at −78° C. for 1 h before it was allowed to warm to room temperature over night. Saturated aqueous $NH_4Cl$ solution was added and the mixture was extracted with MTBE. The organic layer was separated, dried ($Na_2SO_4$) and concentrated in vacuum. The residue was purified by flash chromatography on silica gel to yield the title compound (230 mg, 45%).

HPLC-MS: 3.935, m/z=460.00.

Step 2: Synthesis of 1-{4-[5-(3,5-Dichloro-phenyl)-5-trifluoromethyl-4,5-dihydro-isoxazol-3-yl]-2-methyl-phenyl}-3-methyl-butan-1-one To a solution of 1-{4-[5-(3,5-Dichloro-phenyl)-5-trifluoromethyl-4,5-dihydro-isoxazol-3-yl]-2-methyl-phenyl}-3-methyl-butan-1-ol (i.e. the product of Step 1, 1.20 g) in $CH_2Cl_2$ (50 mL) was added Dess-Martin-Periodinan (CAS [87413-09-0], 1.216 g) in small portions. After 30 min at room temperature, saturated aqueous $NaHCO_3$ and $Na_2S_2O_4$ solutions were added and the mixture was extracted with $CH_2Cl_2$. The organic layer was washed with water, dried ($Na_2SO_4$) and concentrated in vacuum. The residue was purified by flash chromatography on silica gel to yield the title compound (1.05 g, 88%).

HPLC-MS: 4.220, m/z=458.05.

Step 3: Synthesis of 1-{4-[5-(3,5-Dichloro-phenyl)-5-trifluoromethyl-4,5-dihydro-isoxazol-3-yl]-2-methyl-phenyl}-3-methyl-butan-1-one-oxime To a solution of 1-{4-[5-(3,5-dichloro-phenyl)-5-trifluoromethyl-4,5-dihydro-isoxazol-3-yl]-2-methyl-phenyl}-3-methyl-butan-1-one (i.e. the product of Step 2, 228 mg) in methanol (14.3 mL) was added hydroxylamine hydrochloride (38 mg) and a catalytic amount of concentrated hydrochloric acid. The mixture was stirred at 70° C. for 4 h and concentrated in vacuum. Water was added and the mixture was extracted with ethyl acetate. Combined organic layers were dried ($Na_2SO_4$) and evaporated. Flash chromatography of the residue on silica gel obtained the title compound (94 mg, 40%).

HPLC-MS: 4.663, m/z=473.10.

Example 10

(Z)- and (E)-{4-[5-(3,5-Dichloro-phenyl)-5-trifluoromethyl-4,5-dihydro-isoxazol-3-yl]-2-methyl-phenyl}-[hydroxyimino]-acetic acid methyl ester (Compounds 1-42 and 1-43 of table C.1)

Step 1: Synthesis of {4-[5-(3,5-Dichloro-phenyl)-5-trifluoromethyl-4,5-dihydro-isoxazol-3-yl]-2-methyl-phenyl}-oxo-acetic acid methyl ester To a solution of 3-(4-bromo-3-methyl-phenyl)-5-(3,5-dichloro-phenyl)-5-trifluoromethyl-4,5-dihydro-isoxazole (1.00 g) in THF (40 mL) was added tert-butyllithium (16.2 mL of a 1.6 M solution in pentane) at −78° C. After 10 min at this temperature, $MgBr_2$ (0.15 M in THF, 10.3 mL) was added dropwise and left for another 15 min. Oxalic acid methylester chloride (284 mg) was added and the mixture was stirred at −78° C. for 1 h before it was allowed to warm to room temperature over night. Saturated aqueous $NH_4Cl$ solution was added and the mixture was extracted with MTBE. The organic layer was separated, dried ($Na_2SO_4$) and concentrated in vacuum. The residue was purified by flash chromatography on silica gel to yield the title compound (167 mg, 16%).
HPLC-MS: 4.467, m/z=460.05.

Step 2: Synthesis of (Z)- and (E)-{4-[5-(3,5-Dichloro-phenyl)-5-trifluoromethyl-4,5-dihydro-isoxazol-3-yl]-2-methyl-phenyl}-[hydroxyimino]-acetic acid methyl ester To a solution of {4-[5-(3,5-dichloro-phenyl)-5-trifluoromethyl-4,5-dihydro-isoxazol-3-yl]-2-methyl-phenyl}-oxo-acetic acid methyl ester (i.e. the product of Step 1, 140 mg) in methanol (14.3 mL) was added hydroxylamine hydrochloride (32 mg) and a catalytic amount of concentrated hydrochloric acid. The mixture was stirred at 70° C. for 4 h and concentrated in vacuum. Water was added and the mixture was extracted with ethyl acetate. Combined organic layers were dried ($Na_2SO_4$) and evaporated. Flash chromatography of the residue on silica gel obtained the title compounds (19 mg of 1-42 and 43 mg of 1-43, together 43%).
Isomer 1-42
HPLC-MS: 3.987, m/z=475.00.
$^1$H-NMR (500 MHz, $CDCl_3$): δ=2.18 (s, 3H), 3.69 (d, 1H), 3.88 (s, 3H), 4.10 (d, 1H), 7.38 (m, 1H), 7.43 (s, 1H), 7.47-7.60 (m, 4H), 10.50 (br. s, 1H) ppm.
Isomer 1-43
HPLC-MS: 3.856, m/z=475.00.
$^1$H-NMR (500 MHz, $CDCl_3$): δ=2.22 (s, 3H), 3.70 (d, 1H), 3.84 (s, 3H), 4.10 (d, 1H), 7.21 (d, 1H), 7.38 (m, 1H), 7.43 (s, 1H), 7.51 (s, 2H), 7.53 (d, 1H), 7.59 (s, 1H), 9.95 (br. s, 1H) ppm.

Example 11

[1-{4-[5-(3,5-Dichloro-phenyl)-5-trifluoromethyl-4,5-dihydro-isoxazol-3-yl]-2-methyl-phenyl}-methylidene]-hydrazine (Compound 1-46 of table C.1)

A solution of 4-[5-(3,5-dichloro-phenyl)-5-trifluoromethyl-4,5-dihydro-isoxazol-3-yl]-2-methyl-benzaldehyde (i.e. the product of Step 1, Example 1, 500 mg), concentrated hydrochloric acid (5 drops) and hydrazine hydrate (86 mg) in methanol (20 mL) were heated at reflux for 5 h. The mixture was concentrated and the residue was triturated with water. Filtration yielded the title compound (317 mg, 61%).
$^1$H-NMR (360 MHz, $CDCl_3$): δ=2.59 (s, 3H), 3.72 (d, 1H), 4.11 (d, 1H), 7.44 (m, 1H), 7.50-7.62 (m, 4H), 8.14 (d, 1H), 8.98 (s, 1H) ppm.

Example 12

2-Chloro-4-[5-(3,5-dichloro-phenyl)-5-trifluoromethyl-4,5-dihydro-isoxazol-3-yl]-benzaldehyde oxime (Compound 5-1 of table C.5)

Step 1: Synthesis of 2-Chloro-4-[5-(3,5-dichloro-phenyl)-5-trifluoromethyl-4,5-dihydro-isoxazol-3-yl]-benzoic acid methyl ester A mixture of 3-(4-bromo-3-chloro-phenyl)-5-(3,5-dichloro-phenyl)-5-trifluoromethyl-4,5-dihydro-isoxazole (4.00 g), palladium bis(diphenylphosphine) dichloride $CH_2Cl_2$-complex (0.69 g), palladium acetate (0.14 g), sodium acetate (1.03 g), and methanol (50 mL) was placed in an autoclave, charged with 5 bar of carbon monoxide and stirred at 100° C. for 16 h. After cooling, the autoclave was opened and the reaction mixture was filtered. The filtrate was concentrated in vacuum and the residue was purified by flash chromatography on silica gel to obtain the title compound (2.2 g, 58%).
HPLC-MS: 4.285 min, M=451.95

Step 2: Synthesis of 2-Chloro-4-[5-(3,5-dichloro-phenyl)-5-trifluoromethyl-4,5-dihydro-isoxazol-3-yl]-benzaldehyde To a solution of 2-chloro-4-[5-(3,5-dichloro-phenyl)-5-trifluoromethyl-4,5-dihydro-isoxazol-3-yl]-benzoic acid methyl ester (i.e. the product of Step 1, 2.20 g) in $CH_2Cl_2$ was added a solution of diisobutyl aluminium hydride (1 M in $CH_2Cl_2$, 10.7 mL) at −78° C. and kept at this temperature for 30 min. MeOH (25 mL) was added carefully and the mixture was allowed to warm to room temp, when aqueous K—Na-tartrate solution was added. The layers were separated and the aqueous phase was extracted with $CH_2Cl_2$, combined organic layers were washed with water, dried ($Na_2SO_4$) and evaporated. The residue was purified by flash chromatography on silica gel to obtain the title compound (1.35 g, 66%) and 2-chloro-4-[5-(3,5-dichloro-phenyl)-5-trifluoromethyl-4,5-dihydro-isoxazol-3-yl]-benzyl alcohol (0.49 g, 24%).
HPLC-MS: 4.238 min, M=421.85.
$^1$H-NMR (400 MHz, $CDCl_3$): δ=3.73 (d, 1H), 4.10 (d, 1H), 7.43 (m, 1H), 7.50 (s, 2H), 7.62 (d, 1H), 7.76 (s, 1H), 7.98 (d, 1H), 10.48 (s, 1H) ppm.

Step 3: Synthesis of 2-Chloro-4-[5-(3,5-dichloro-phenyl)-5-trifluoromethyl-4,5-dihydro-isoxazol-3-yl]-benzaldehyde oxime To a solution of 2-chloro-4-[5-(3,5-dichloro-phenyl)-5-trifluoromethyl-4,5-dihydro-isoxazol-3-yl]-benzaldehyde (i.e.

the product of Step 2, 1.20 g) in methanol (5 mL) was added hydroxylamine hydrochloride (296 mg) and a catalytic amount of concentrated hydrochloric acid. The mixture was stirred at 70° C. for 3 h and concentrated in vacuum. Water was added and the mixture was extracted with ethyl acetate. Combined organic layers were dried (Na₂SO₄) and evaporated to obtain the title compound (1.2 g, 97%).

HPLC-MS: 4.053 min, M=436.95.

The following examples were synthesized analogously.

C.1 Compound Examples 1

Compound examples 1-1 to 1-60 correspond to compounds of formula C.1:

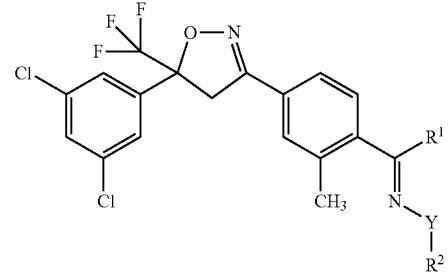

(C.1)

wherein $R^1$, $R^2$ and Y of each synthesized compound is defined in one row of table C.1 below.

TABLE C.1

| Compound Ex. | $R^1$ | $R^2$ | Y | $R_t$ (min) | [M + H] |
|---|---|---|---|---|---|
| 1-1 | H | H | O | 4.007 | 417.00 |
| 1-2 | H | CH₃ | O | 3.941 | 431.00 |
| 1-3 | H | C(=O)CH₃ | O | see example 3 | |
| 1-4 | H | C(=O)CH₂CH₃ | O | see example 4 | |
| 1-5 | H | CH₂CN | O | 4.459 | 455.95 |
| 1-6 | H | CH₂CF₃ | O | 4.514 | 484.05 |
| 1-7 | H | CH₂—C(=O)NH—CH₂CH₃ | O | 4.062 | 502.00 |
| 1-8 | H | CH₂—C(=O)NH—CH(CH₃)₂ | O | 4.325 | 516.05 |
| 1-9 | H | CH₂—C(=O)NH—CH₂CF₃ | O | 4.328 | 556.05 |
| 1-10 | H | CH₂—C(=O)NH—CH₂$^{cyclo}$C₃H₅ | O | 4.334 | 528.05 |
| 1-11 | H | CH₂—C(=O)NH—CH₂C≡CH | O | 4.178 | 512.05 |
| 1-12 | H | CH₂—C(=O)OH | O | 3.953 | 475.00 |
| 1-13 | H | CH₂—C(=O)O—C(CH₃)₃ | O | 4.873 | 531.05 |
| 1-14 | H | CH₂—C(=O)NH—CH₃ | O | 4.091 | 488.05 |
| 1-15 | H | CH₂C(=O)NH—CH₂-4-Cl—C₆H₄ | O | 4.411 | 698.00 |
| 1-16 | H | CH₂C(=O)N-morpholine | O | 4.162 | 544.05 |
| 1-17 | CH₃ | H | O | 4.191 | 431.05 |
| 1-18 | CH₃ | CH₃ Z-Isomer | O | 4.436 | 445.00 |
| 1-19 | CH₃ | CH₃ E-Isomer | O | 4.299 | 445.00 |
| 1-20 | CH₃ | CH₂CF₃ | O | 4.806 | 498.95 |
| 1-21 | CH₃ | CH₂—C(=O)NH—CH₂CH₃ Z-Iso | O | 4.075 | 516.00 |
| 1-22 | CH₃ | CH₂—C(=O)NH—CH₂CH₃ E-Iso | O | 4.983 | 516.00 |
| 1-23 | CH₃ | CH₂—C(=O)NH—CH₂CF₃ Z-Iso | O | 4.216 | 570.00 |
| 1-24 | CH₃ | CH₂—C(=O)NH—CH₂CF₃ E-Iso | O | 4.221 | 570.00 |
| 1-25 | CH₃ | CH₂—C(=O)NH—CH₂$^{cyclo}$C₃H₅ | O | 4.358 | 542.00 |
| 1-26 | CH₃ | CH₂—C(=O)OH | O | 4.952 | 489.00 |
| 1-27 | CH₃ | CH₂—C(=O)NH—CH₃ Z-Isomer | O | 3.932 | 502.00 |
| 1-28 | CH₃ | CH₂—C(=O)NH—CH₃ E-Isomer | O | 3.953 | 502.00 |
| 1-29 | CN | H | O | 4.083 | 442.00 |
| 1-30 | OCH₃ | H Z-Isomer | O | 4.163 | 447.05 |
| 1-31 | OCH₃ | H E-Isomer | O | 3.901 | 447.05 |
| 1-32 | OCH₃ | CH₃ Z-Isomer | O | 4.525 | 461.05 |
| 1-33 | OCH₃ | CH₃ E-Isomer | O | 4.227 | 461.05 |
| 1-34 | OCH₃ | CH₂CH₃ Z-Isomer | O | 4.786 | 475.10 |
| 1-35 | OCH₃ | CH₂CH₃ E-Isomer | O | 4.470 | 475.10 |
| 1-36 | OCH₃ | CH₂CH₂CH₃ | O | 4.657 | 489.10 |
| 1-37 | OCH₃ | CH₂—C₆H₅ Z-Isomer | O | 4.726 | 537.05 |
| 1-38 | OCH₃ | CH₂—C₆H₅ E-Isomer | O | 4.507 | 537.05 |
| 1-39 | OCH₃ | CH₂CF₃ | O | 4.357 | 526.00 |
| 1-40 | OCH₃ | CH(CH₃)₂ Z-Isomer | O | 4.815 | 489.10 |
| 1-41 | OCH₃ | CH(CH₃)₂ E-Isomer | O | 4.636 | 489.10 |
| 1-42 | C(=O)CH₃ | H Isomer A | O | 3.987 | 475.00 |
| 1-43 | C(=O)CH₃ | H Isomer B | O | 3.856 | 475.00 |
| 1-44 | H | C(=NH)—NH₂ | NH | 3.545 | 458.00 |
| 1-45 | H | C(=O)-2-pyridyl Z-Isomer | NH | 4.104 | 521.00 |
| 1-46 | H | H | NH | see example 11 | |
| 1-47 | H | CH₂CF₃ | NH | 4.483 | 484.05 |
| 1-48 | H | C(=O)NH—CH₂CF₃ | NH | 4.281 | 541.00 |
| 1-49 | H | C(=NH)—N(CH₃)₂ | NH | 3.603 | 486.00 |
| 1-50 | CH₃ | C(=O)-2-pyridyl Z-Isomer | NH | 3.754 | 535.05 |
| 1-51 | CH₃ | C(=O)-2-pyridyl E-Isomer | NH | 3.782 | 535.05 |
| 1-52 | CH₃ | H | NH | 3.186 | 430.05 |
| 1-53 | H | C(=NH)—NH₂ | NCH₃ | 3.557 | 472.00 |
| 1-54 | CH₂CH(CH₃)₂ | C(=O)—CF₃ | NH | 4.635 | 568.00 |
| 1-55 | CH₂CH(CH₃)₂ | H | O | 4.663 | 473.10 |
| 1-56 | CH₂CH(CH₃)₂ | CH₃ | O | 4.261 | 487.00 |

TABLE C.1-continued

| Compound Ex. | R¹ | R² | Y | $R_t$ (min) | [M + H] |
|---|---|---|---|---|---|
| 1-57 | H | C(=NH)—NH—O₅H₁₁ | NH | 4.169 | 528.15 |
| 1-58 | H | C(=NH)—NH—CH₃ | NH | 3.707 | 472.05 |
| 1-59 | H | C(=O)NH-3-thiolyl-1,1-dioxide | NH | 4.092 | 577.05 |
| 1-60 | H | C(=O)—NH—CH₃ | NH | 4.193 | 473.05 |

C.2 Compound Examples 2

Compound example 2-1 corresponds to compound formula C.2:

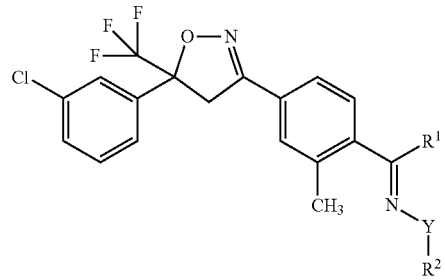

(formula C.2)

wherein R¹, R², and Y of each synthesized compound is defined in one row of table C.2 below.

TABLE C.2

| Compound Ex. | R¹ | R² | Y | $R_t$ (min) | [M + H] |
|---|---|---|---|---|---|
| 2-1 | H | H | O | 3.653 | 383.05 |

C.3 Compound Examples 3

Compound example 3-1 corresponds to compound formula C.3:

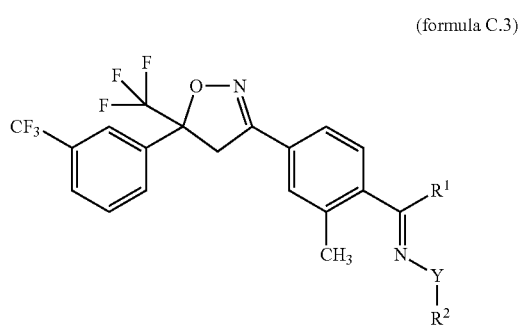

(formula C.3)

wherein R¹, R² and Y of each synthesized compound is defined in one row of table C.3 below.

TABLE C.3

| Compound Ex. | R¹ | R² | Y | $R_t$ (min) | [M + H] |
|---|---|---|---|---|---|
| 3-1 | H | H | O | 3.704 | 417.05 |

C.4 Compound Examples 4

Compound example 4-1 corresponds to compound formula C.4:

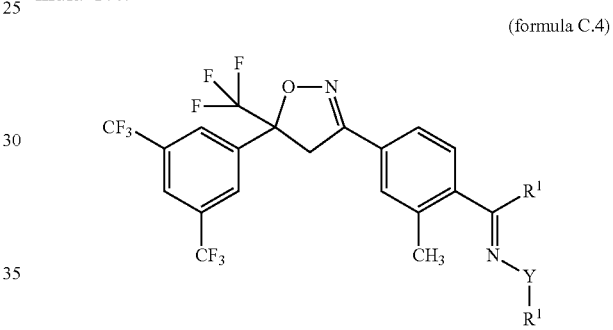

(formula C.4)

wherein R¹, R² and Y of each synthesized compound is defined in one row of table C.4 below.

TABLE C.4

| Compound Ex. | R¹ | R² | Y | $R_t$ (min) | [M + H] |
|---|---|---|---|---|---|
| 4-1 | H | H | O | 4.113 | 485.10 |

C.5 Compound Examples 5

Compound examples 5-1, 5-8, 5-10, 5-12 and 5-48 correspond to compound formula C.5:

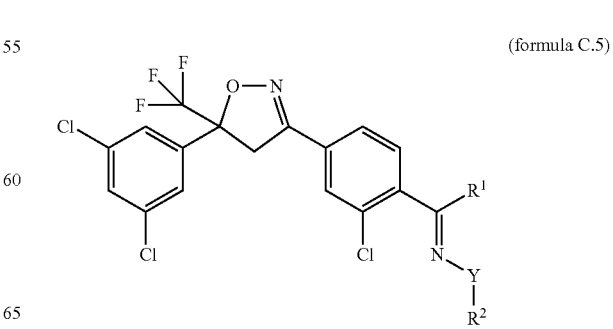

(formula C.5)

wherein $R^1$, $R^2$ and Y of each synthesized compound is defined in one row of table C.5 below.

TABLE C.5

| Compound Ex. | $R^1$ | $R^2$ | Y | $R_t$ (min) | [M + H] |
|---|---|---|---|---|---|
| 5-1 | H | H | O | 4.090 | 436.95 |
| 5-8 | H | CH$_2$—C(=O)NH—CH(CH$_3$)$_2$ | O | 4.650 | 536.05 |
| 5-10 | H | CH$_2$—C(=O)NH—CH$_2$$^{cyclo}$C$_3$H$_5$ | O | 4.522 | 533.95 |
| 5-12 | H | CH$_2$—C(=O)OH | O | 4.418 | 494.95 |
| 5-48 | H | C(=O)NH—CH$_2$CF$_3$ | NH | 4.167 | 560.95 |

C.6 Compound Examples 6

Compound examples 6-1 and 6-48 correspond to compound formula C.6:

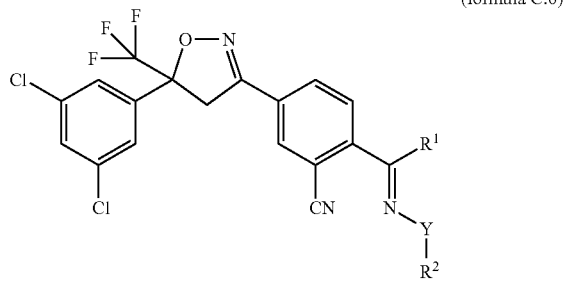
(formula C.6)

wherein $R^1$, $R^2$ and Y of each synthesized compound is defined in one row of table C.6 below.

TABLE C.6

| Compound Ex. | $R^1$ | $R^2$ | Y | $R_t$ (min) | [M + H] |
|---|---|---|---|---|---|
| 6-1 | H | H | O | 3.778 | 428.20 |
| 6-48 | H | C(=O)NH—CH$_2$CF$_3$ | NH | 4.394 | 552.00 |

C.7 Compound Examples 7

Compound examples 7-1 and 7-48 correspond to compound formula C.7:

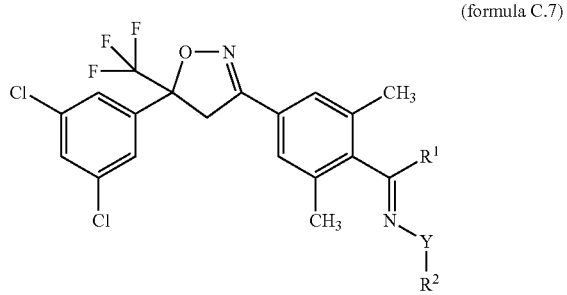
(formula C.7)

wherein $R^1$, $R^2$ and Y of each synthesized compound is defined in one row of table C.7 below.

TABLE C.7

| Compound Ex. | $R^1$ | $R^2$ | Y | $R_t$ (min) | [M + H] |
|---|---|---|---|---|---|
| 7-1 | H | H | O | 4.455 | 430.95 |
| 7-48 | H | C(=O)NH—CH$_2$CF$_3$ | NH | 4.563 | 555.05 |

C.8 Compound Examples 8

Compound example 8-1 corresponds to compound formula C.8:

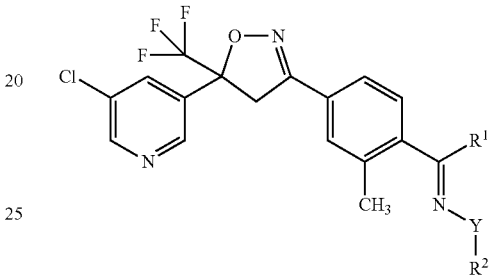
(formula C.8)

wherein $R^1$, $R^2$ and Y of each synthesized compound is defined in one row of table C.8 below.

TABLE C.8

| Compound Ex. | $R^1$ | $R^2$ | Y | $R_t$ (min) | [M + H] |
|---|---|---|---|---|---|
| 8-1 | H | H | O | 3.272 | 384.05 |

II. Evaluation of Pesticidal Activity

The activity of the compounds of formula I of the present invention could be demonstrated and evaluated by the following biological test.

If not otherwise specified the test solutions were prepared as follow:

The active compound was dissolved at the desired concentration in a mixture of 1:1 (vol:vol) distilled water:acteon. The test solution was prepared the day it was used and in general at concentrations of ppm (wt/vol).

B.1 Cotton Aphid (*Aphis gossypii*)

The active compounds were formulated in cyclohexanone as a 10,000 ppm solution supplied in tubes. The tubes were inserted into an automated electrostatic sprayer equipped with an atomizing nozzle and served as stock solutions for which lower dilutions were made in 50% acetone:50% water (v/v). A nonionic surfactant (Kinetic®) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25°

C. and 20-40% relative humidity. Aphid mortality on the treated plants, relative to mortality on untreated control plants, was determined after 5 days.

In this test, the compounds 1-16 and 1-44 at 300 ppm, respectively, showed a mortality of at least 75% in comparison with untreated controls.

B.2 Cowpea Aphid (*Aphis craccivora*)

Potted cowpea plants colonized with approximately 100-150 aphids of various stages were sprayed after the pest population had been recorded. Population reduction was assessed after 24, 72, and 120 hours.

In this test, the compound 1-16 at 500 ppm showed a mortality of at least 75% in comparison with untreated controls.

B.3 Diamond Back Moth (*Plutella xylostella*)

Leaves of Chinese cabbage were dipped in test solution and air-dried. Treated leaves were placed in petri dished lined with moist filter paper. Mortality was recorded 24, 72, and 120 hours after treatment.

In this test, the compounds 1-2, 1-4, 1-5, 1-6, 1-7, 1-8, 1-9, 1-10, 1-11, 1-13, 1-14, 1-16, 1-17, 1-18, 1-21, 1-23, 1-24, 1-29, 1-30, 1-31, 1-32, 1-33, 1-34, 1-35, 1-36, 1-38, 1-39, 1-41, 1-43, 1-47, 1-48, 1-49, 1-51, 1-52, 1-53, 1-54 and 1-55 at 300 ppm, respectively, showed a mortality of at least 75% in comparison with untreated controls.

B.4 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 µl, using a custom built micro atomizer, at two replications. After application, microtiter plates were incubated at about 28±1° C. and about 80±5% relative humidity for 5 days. Egg and larval mortality was then visually assessed.

In this test, the compounds 1-3, 1-5, 1-7, 1-10, 1-11, 1-14, 1-15, 1-16, 1-18, 1-22, 1-23, 1-29, 1-30, 1-31, 1-33, 1-35, 1-36, 1-39, 1-41, 1-44, 1-47, 1-48, 1-49, 1-52, 1-53 and 1-56 at 2500 ppm, respectively, showed a mortality of at least 75% in comparison with untreated controls.

B.5 Orchid Thrips (*Dichromothrips corbetti*)

*Dichromothrips corbetti* adults used for bioassay were obtained from a colony maintained continuously under laboratory conditions. For testing purposes, the test compound was diluted to a concentration of 300 ppm (wt compound: vol diluent) in a 1:1 mixture of acetone:water (vol:vol), plus 0.01% vol/vol Kinetic® surfactant.

Thrips potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with 10-15 adult thrips. The petri dishes were then covered with lids. All test arenas were held under continuous light and a temperature of about 28° C. for duration of the assay. After 4 days, the numbers of live thrips was counted on each flower, and along inner walls of each petri dish. The level of thrips mortality was extrapolated from pre-treatment thrips numbers.

In this test, the compounds 1-17, 1-29, 1-33, 1-35, 1-36, 1-39 and 1-48 at 300 ppm, respectively, showed a mortality of at least 75% in comparison with untreated controls.

B.6 Rice Green Leafhopper (*Nephotettix virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds 1-4 and 1-48 at 500 ppm, respectively, showed a mortality of at least 75% in comparison with untreated controls.

B.7 Rice Brown Plant Hopper (*Nilaparvata lugens*)

Rice seedlings were cleaned and washed 24 hours before spraying. The active compounds were formulated in 50:50 acetone:water (vol:vol) and 0.1% vol/vol surfactant (EL 620) is added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds 1-4, 1-35 and 1-39 at 500 ppm, respectively, showed a mortality of at least 75% in comparison with untreated controls.

B.8 Silverleaf Whitefly (*Bemisia argentifolii*)

The active compounds were formulated in cyclohexanone as a 10,000 ppm solution supplied in tubes. The tubes were inserted into an automated electrostatic sprayer equipped with an atomizing nozzle and served as stock solutions for which lower dilutions were made in 50% acetone:50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds 1-12, 1-14, 1-15, 1-41 and 1-48 at 300 ppm, respectively, showed a mortality of at least 75% in comparison with untreated controls.

B.9 Southern Armyworm (*Spodoptera eridania*)

The active compounds were formulated in cyclohexanone as a 10,000 ppm solution supplied in tubes. The tubes were inserted into an automated electrostatic sprayer equipped with an atomizing nozzle and served as stock solutions for which lower dilutions are made in 50% acetone:50% water (v/v). A nonionic surfactant (Kinetic®) was included in the solution at a volume of 0.01% (v/v).

Lima bean plants (variety Sieva) were grown 2 plants to a pot and selected for treatment at the 1$^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds 1-2, 1-3, 1-4, 1-5, 1-6, 1-7, 1-8, 1-9, 1-10, 1-11, 1-13, 1-14, 1-15, 1-16, 1-29, 1-30, 1-31, 1-32, 1-33, 1-34, 1-35, 1-36, 1-37, 1-38, 1-39, 1-41, 1-48 and 1-49 at 300 ppm, respectively, showed a mortality of at least 75% in comparison with untreated controls.

B.10 Red Spider Mite (*Tetranychus kanzawai*)

The active compound was dissolved at the desired concentration in a mixture of 1:1 (v/v) distilled water:acetone. Surfactant (Alkamuls® EL 620) at the rate of 0.1% (v/v) was added. The test solution was prepared the day it was used.

Potted cowpea beans of 7-10 days of age were cleaned with tap water and sprayed with 5 ml of the test solution using air driven hand atomizer. The treated plants were allowed to air dry and afterwards inoculated with 20 or more mites by clipping a cassava leaf section with known mite population. Treated plants were placed inside a holding room at about 25-27° C. and about 50-60% relative humidity. Mortality was assessed by counting the live mites 72 HAT. Percent mortality was assessed after 72 h.

The active compounds were dissolved at the desired concentration in a mixture of 1:1 (v/v) acetone:water. The test solutions were prepared the day they were used.

In this test, the compounds 1-8, 1-14, 1-37 and 1-48 at 500 ppm, respectively, showed a mortality of at least 75% in comparison with untreated controls.

B.11 Vetch Aphid (*Megoura viciae*)

For evaluating control of vetch aphid (*Megoura viciae*) through contact or systemic means the test unit consisted of 24-well-microtiter plates containing broad bean leaf disks. The compounds were formulated using a solution containing 75% v/v water and 25% v/v DMSO. Different concentrations of formulated compounds were sprayed onto the leaf disks at 2.5 µl, using a custom built micro atomizer, at two replications. After application, the leaf disks were air-dried and 5-8 adult aphids were placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds 1-3, 1-5, 1-8, 1-12, 1-29, 1-31, 1-39 and 1-48 at 2500 ppm, respectively, showed a mortality of at least 75% in comparison with untreated controls.

B.12 Tobacco Budworm (*Heliothis virescens*) I

For evaluating control of tobacco budworm (*Heliothis virescens*) the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 µl, using a custom built micro atomizer, at two replications. After application, microtiter plates are incubated at about 28±1° C. and about 80±5% relative humidity for 5 days. Egg and larval mortality is then visually assessed.

In this test, the compounds 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-26, 1-27, 1-28, 1-29, 1-30, 1-31, 1-32, 1-33, 1-34, 1-35, 1-36, 1-39, 1-40, 1-41, 1-42, 1-43, 1-44, 1-45, 1-47, 1-48, 1-49, 1-51, 1-52, 1-53, 1-54, 1-55 and 1-56, at 2500 ppm, respectively showed a mortality of at least 75% in comparison with untreated controls.

B.13 Boll Weevil (*Anthonomus grandis*)

For evaluating control of boll weevil (*Anthonomus grandis*) the test unit consisted of 24-well-microtiter plates containing an insect diet and 20-30 *A. grandis* eggs. The compounds were formulated using a solution containing 75% v/v water and 25% v/v DMSO. Different concentrations of formulated compounds were sprayed onto the insect diet at 20 µl, using a custom built micro atomizer, at two replications. After application, microtiter plates were incubated at about 23±1° C. and about 50±5% relative humidity for 5 days. Egg and larval mortality was then visually assessed.

In this test, the compounds 1-3, 1-4, 1-7, 1-8, 1-9, 1-10, 1-11, 1-14, 1-16, 1-17, 1-18, 1-29, 1-30, 1-31, 1-32, 1-33, 1-34, 1-35, 1-36, 1-39, 1-41, 1-43, 1-45, 1-47, 1-48, 1-52, 1-53, 1-54, 1-55 and 1-56 at 2500 ppm, respectively, showed a mortality of at least 75% in comparison with untreated controls.

B.14 Western Flower Thrips (*Frankliniella occidentalis*)

Serial dilutions of each technical grade AI were made in pure acetone. 0.5 ml of the treatment solution was deposited into the bottom of a glass vial (scintillation vial). The cap was screwed back onto the vial and inverted for about five seconds. The cap was subsequently removed and the vial laid on its side and rolled constantly, on a hot dog roller, until all the acetone had flashed off and the inner surface of the vial was dry. Cotton leave discs were also dipped simultaneously into the treatment solutions and allowed to dry. After the vials were dried, the leave discs were placed into the vials to serve as a food/water source for the thrips. Each treatment was replicated 5-fold. Western flower thrips were aspirated into the vials, approximately 5 larvae or adults/vial. Following treatment application the vials were held in a holding room under fluorescent light and constant 26° C. Thrips mortality was assessed at 2 DAT (days after treatment), counting all thrips both dead and alive.

In this test, the compound 1-48 at 300 ppm showed a mortality of at least 75% in comparison with untreated controls.

BA. Animal Health

General Test Conditions of Animal Health Assays

If not otherwise specified, the tests were conducted as glass vial contact assays. Glass vials (20 ml scintillation vials) were used. Treatment solutions were mixed with technical grade chemicals diluted in acetone. Treatment solutions needed for the assays included generally 1 and 10 ppm (0.01 and 0.1 µg/cm$^2$, respectively), but optionally also 100 and/or 1000 ppm for first tier vials. As commercial standard, alphacypermethrin was run at 1 ppm. As solvent control, acetone was used for the assay. Treatment solution was pipetted into the bottom of each vial. Each vial was turned on its side and placed onto a commercial grade hot dog roller without applying heat. The uncapped vials were allowed to roll to allow for the acetone treatment to vent off. After drying, the vials were placed into the compartmented vial shipping boxes. The workstation was prepared by chilling the table and plastic Petri dishes with the inside wall coated with Fluon. A weigh boat of 10% sugar water saturated cotton dental pellets was also prepared. The animal pests were collected into a tube with a rechargeable insect vacuum. The tube of animal pests was placed in a laboratory refrigerator until the animal pests were incapacitated. The animal pests were emptied into chilled Petri dish. A small cotton dental pellet was soaked in water or in 10 wt % sugar water, whereas the excess solution was gently squeezed out. The cotton dental pellet was placed into the bottom of each vial. For the test, the animal pests were added to each vial and then the cap was loosely put on the vial to allow for ventilation. The test vials were hold at ambient room temperature in compartmented boxes. In general, the animal pests were observed for incapacitation at least at 4, 24, and 48 hours after infestation, or for a longer period if required. Mortality was defined as an insect incapable of coordinated movement when agitated.

BA.1 Acrobat Ant Workers (*Crematogaster* sp.)

Treatment solutions were mixed with test compound diluted in acetone at concentrations of 10 and 100 ppm. Collected ants for placement in the vials were typically not chilled prior to infesting vials. Data were collected at 1, 2, and 4 days after infestation.

In this test, the compound 1-48 at 100 ppm showed 48 h after treatment a mortality of at least 75% in comparison with untreated controls.

BA.2 Brown Dog Tick Adults (*Rhipicephalus sanguineus*)

Treatment solutions were mixed with test compound diluted in acetone at concentrations of 10 and 100 ppm. No food or water source was provided in the vials. Data were collected out to 5 days after infestation. Ticks were evaluated by rolling the vials on a preheated hotdog roller. Tick activity was stimulated within approx. 1-2 minutes.

In this test, the compound 1-48 at 100 ppm showed 3 DAT (days after treatment) a mortality of at least 75% in comparison with untreated controls.

BA.6 Yellowfever Mosquito Adults (*Aedes aegypti*)

BA.6.a Larval Mosquito Water Treatment Assay

The assay was conducted in 6-well polystyrene plates using one plate per treatment rate. Stock solutions were prepared at 100 and 1000 ppm. Screen rates were at 1 and 10 ppm. Distilled water was added to each well, control wells were treated with acetone. Temephos (Abate technical) was used as the standard at 0.1 ppm. Ten early 4th-instar yellowfever mosquito larvae (*Aedes aegypti*) in water were added to each well. One drop of liver powder solution (6 g in 100 ml distilled water) was added to each well as a food source daily. Plates were maintained at 22-25° C. and 25-50% RH (relative humidity) and observed daily for dead larvae and pupae at 1, 2, 3, and 5 days after treatment. Dead larvae and all pupae were removed daily. Mortality was defined as an insect incapable of coordinated movement when agitated.

In this test, the compounds 1-14 and 1-48 at 1 ppm, respectively, showed at 5 DAT (days of treatment) a mortality of at least 75% in comparison with untreated controls.

LENGTHY TABLES

The patent contains a lengthy table section. A copy of the table is available in electronic form from the USPTO web site (http://seqdata.uspto.gov/?pageRequest=docDetail&DocID=US08722673B2). An electronic copy of the table will also be available from the USPTO upon request and payment of the fee set forth in 37 CFR 1.19(b)(3).

We claim:

1. A compound of formula (I)

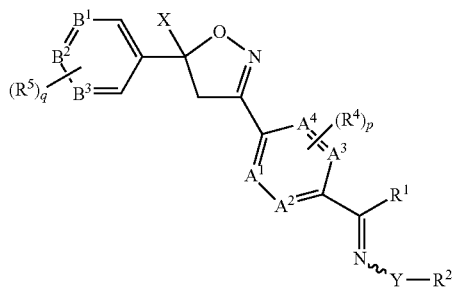

(I)

wherein $A^1$, $A^2$, $A^3$ and $A^4$ are CH;

$B^1$, $B^2$ and $B^3$ are CH;

X is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl and $C_3$-$C_6$-halocycloalkyl;

Y is O, N—$R^3$, $S(O)_n$ or a chemical bond;

$R^1$ is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_1$-$C_{10}$-alkylthio; $C_1$-$C_{10}$-haloalkylthio; $C_1$-$C_{10}$-alkylsulfinyl; $C_1$-$C_{10}$-haloalkylsulfinyl; $C_1$-$C_{10}$-alkylsulfonyl; $C_1$-$C_{10}$-haloalkylsulfonyl; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; phenyl which may be substituted by 1, 2, 3, 4 or 5 radicals $R^{10}$; and a C-bound 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

$R^2$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$;

—N($R^8$)$R^9$; —N($R^8$)C(=O)$R^6$; —Si($R^{14}$)$_2$$R^{13}$; —O$R^7$; —S$R^7$; —S(O)$_m$$R^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

with the proviso that $R^2$ is not —$OR^7$ if Y is O;

or $R^1$ and $R^2$, together with the atoms to which they are bound, form a partially unsaturated 5- or 6-membered heterocyclic ring which, apart from the nitrogen atom of the imine group and the group Y if this is different from a chemical bond, optionally contains 1 or 2 further heteroatoms or heteroatom groups selected from the group consisting of N, O, S, NO, SO and $SO_2$, as ring members, where the heterocyclic ring may carry 1, 2 or 3 substituents $R^6$;

$R^3$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$;

—$N(R^8)R^9$; —$Si(R^{14})_2R^{13}$; —$OR^7$; —$SR^7$; —$S(O)_mR^7$; —$S(O)_nN(R^8)R^9$; —$C(=O)R^6$; —$C(=O)OR^7$; —$C(=O)N(R^8)R^9$; —$C(=S)R^6$; —$C(=S)OR^7$; —$C(=S)N(R^8)R^9$; —$C(=NR^8)R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or $R^2$ and $R^3$ together form a group =$CR^{11}R^{12}$; =$S(O)_mR^7$; =$S(O)_mN(R^8)R^9$; =$NR^8$; or =$NOR^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or $NR^{18}$ and/or 1 or 2 of the $CH_2$ groups of the alkylene chain may be replaced by a group C=O, C=S and/or C=$NR^{18}$; and/or the alkylene chain may be substituted by one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

each $R^4$ is independently selected from the group consisting of halogen; cyano; azido; nitro; —SCN; $SF_5$; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_6$-alkenyl which may be partially or fully halogenated and/or may be substituted by one or more radicals $R^6$; $C_2$-$C_6$-alkynyl which may be partially or fully halogenated and/or may be substituted by one or more radicals $R^6$; —$Si(R^{14})_2R^{13}$; —$OR^7$; —$OS(O)_nR^7$; —$SR^7$; —$S(O)_mR^7$; —$S(O)_nN(R^8)R^9$; —$N(R^8)R^9$; —$N(R^8)C(=O)R^6$; —$C(=O)R^6$; —$C(=O)OR^7$; —$C(=NR^8)H$; —$C(=NR^8)R^6$; —$C(=O)N(R^8)R^9$; $C(=S)N(R^8)R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or two radicals $R^4$ bound on adjacent carbon atoms may be together a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —$C(=O)OCH_2$—, —$O(CH_2)O$—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —$C(=S)SCH_2$—, —$S(CH_2)S$—, —$CH_2CH_2NR^8$—, —$CH_2$CH=N—, —CH=CH—$NR^8$—, —OCH=N— and —SCH=N—, thus forming, together with the carbon atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more $CH_2$ groups of the above groups may be replaced by a C=O group;

each $R^5$ is independently selected from the group consisting of halogen, cyano, azido, nitro, —SCN, $SF_5$, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $C_2$-$C_6$-alkenyl which may be partially or fully halogenated and/or may be substituted by one or more radicals $R^6$, $C_2$-$C_6$-alkynyl which may be partially or fully halogenated and/or may be substituted by one or more radicals $R^6$, —$Si(R^{14})_2R^{13}$, —$OR^7$, —$OS(O)_nR^7$, —$SR^7$, —$S(O)_mR^7$, —$S(O)_nN(R^8)R^9$, —$N(R^8)R^9$, $N(R^8)C(=O)R^6$, —$C(=O)R^6$, —$C(=O)OR^7$, —$C(=S)R^6$, —$C(=S)OR^7$, —$C(=NR^8)R^6$, —$C(=O)N(R^8)R^9$, —$C(=S)N(R^8)R^9$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

each $R^6$ is independently selected from the group consisting of cyano, azido, nitro, —SCN, $SF_5$, $C_3$-$C_8$-cycloalkyl, $C_3$-$C_8$-halocycloalkyl, —$Si(R^{14})_2R^{13}$, —$OR^7$, —$OSO_2R^7$, —$SR^7$, —$S(O)_mR^7$, —$S(O)_nN(R^8)R^9$, —$N(R^8)R^9$, —$C(=O)N(R^8)R^9$, —$C(=S)N(R^8)R^9$, —$C(=O)OR^7$, —$C(=O)R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

and, in case $R^6$ is bound to a cycloalkyl group or to a heterocyclic ring formed by $R^1$ and $R^2$ together with the atoms to which they are bound, $R^6$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$; and in groups —C(=O)$R^6$, —C(=S)$R^6$, —C(=N$R^8$)$R^6$ and —N($R^8$)C(=O)$R^6$, $R^6$ may additionally be selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

or two geminally bound radicals $R^6$ together form a group selected from the group consisting of =C$R^{11}R^{12}$, =S(O)$_m R^7$, =S(O)$_m$N($R^8$)$R^9$, =N$R^8$, =NO$R^7$ and =NN$R^8$;

or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

each $R^7$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2 R^{13}$, —S$R^8$, —S(O)$_m R^7$, —S(O)$_n$N($R^8$)$R^9$, —N($R^8$)$R^9$, —N=C$R^{15}R^{16}$, —C(=O)$R^{17}$, —C(=O)N($R^8$)$R^9$, —C(=S)N($R^8$)$R^9$, —C(=O)O$R^{17}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

with the proviso that $R^7$ is not $C_1$-$C_6$-alkoxy or $C_1$-$C_6$-haloalkoxy if it is bound to an oxygen atom;

each $R^8$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —S(O)$_m R^{20}$, —S(O)$_n$N($R^{21}$)$R^{22}$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

each $R^9$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals le, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —S(O)$_m R^{20}$, —S(O)$_n$N($R^{21}$)$R^{22}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or $R^8$ and $R^9$ together form a group =C$R^{11}R^{12}$;

or $R^8$ and $R^9$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and $SO_2$, as ring members, where the heterocyclic ring may be substituted by one or more radicals $R^{10}$;

each $R^{10}$ is independently selected from the group consisting of halogen, cyano, azido, nitro, —SCN, $SF_5$, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$, $C_2$-$C_{10}$-alkenyl which may be partially or fully halogenated and/or may be substituted by one or more radicals $R^{19}$, $C_2$-$C_{10}$-alkynyl which may be partially or fully halogenated and/or may be substituted by one or more radicals $R^{19}$, —Si($R^{14}$)$_2 R^{13}$, —O$R^{20}$, —OS(O)$_n R^{20}$, —S$R^{20}$, —S(O)$_m R^{20}$, —S(O)$_n$N($R^{21}$)$R^{22}$, —N($R^{21}$)$R^{22}$, C(=O)$R^{19}$, —C(=O)O$R^{20}$, —C(=N$R^{21}$)$R^{22}$, —C(=O)N($R^{21}$)$R^{22}$, —C(=S)N($R^{21}$)$R^{22}$, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from the group consisting of N, O, S, NO, SO and $SO_2$, as ring members, which may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —$C(=O)OCH_2$—, —$O(CH_2)O$—, —$SCH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —$C(=S)SCH_2$—, —$S(CH_2)S$—, —$CH_2CH_2NR^{21}$—, —$CH_2CH$=N—, —CH=CH—$NR^{21}$—, —OCH=N— and —SCH=N—, thus forming, together with the atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more $CH_2$ groups of the above groups may be replaced by a C=O group;

$R^{11}$, $R^{12}$ are, independently of each other and independently of each occurrence, selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy, $C_1$-$C_6$-haloalkoxy, —$C(=O)R^{19}$, —$C(=O)OR^{20}$, —$C(=NR^{21})R^{22}$, —$C(=O)N(R^{21})R^{22}$, —$C(=S)N(R^{21})R^{22}$, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, which may be substituted by one or more radicals $R^{10}$;

$R^{13}$, $R^{14}$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^{15}$, $R^{16}$ are, independently of each other and independently of each occurrence, selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, which may be substituted by one or more radicals $R^{10}$;

each $R^{17}$ is independently selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy -$C_1$-$C_o$-alkyl, phenyl and benzyl;

each $R^{18}$ is independently $R^3$;

each $R^{19}$ is independently selected from the group consisting of cyano, azido, nitro, —SCN, $SF_5$, $C_3$-$C_8$-cycloalkyl, $C_3$-$C_8$-halocycloalkyl, —$Si(R^{14})_2R^{13}$, —$OR^{20}$, —$OSO_2R^{20}$, —$SR^{20}$, —$S(O)_mR^{20}$, —$S(O)_nN(R^{21})R^{22}$, —$N(R^{21})R^{22}$, —$C(=O)N(R^{21})R^{22}$, —$C(=S)N(R^{21})R^{22}$, —$C(=O)OR^{20}$, —$C(=O)R^{20}$, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-alkoxy and $C_1$-$C_6$-haloalkoxy;

and, in case $R^{19}$ is bound to a cycloalkyl group, $R^{19}$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_o$-alkynyl and $C_2$-$C_6$-haloalkynyl; and in groups —$C(=O)R^{19}$, $R^{19}$ may additionally be selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, and $C_2$-$C_6$-haloalkynyl;

or two geminally bound radicals $R^{19}$ together form a group selected from the group consisting of =$CR^{11}R^{12}$, =$S(O)_mR^{20}$, =$S(O)_mN(R^{21})R^{22}$, =$NR^{21}$, =$NOR^{20}$ and =$NNR^{21}$;

or two radicals $R^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

each $R^{20}$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$Si(R^{14})_2R^{13}$, $C_1$-$C_6$-alkylaminosulfonyl, amino, $C_1$-$C_6$-alkylamino, di-($C_1$-$C_6$-alkyl)-amino, $C_1$-$C_6$-alkylcarbonyl, $C_1$-$C_6$-haloalkylcarbonyl, aminocarbonyl, $C_1$-$C_6$-alkylaminocarbonyl, di-($C_1$-$C_6$-alkyl)-aminocarbonyl, $C_1$-$C_6$-alkoxycarbonyl, $C_1$-$C_6$-haloalkoxycarbonyl, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

with the proviso that $R^{20}$ is not $C_1$-$C_6$-alkoxy or $C_1$-$C_6$-haloalkoxy if it is bound to an oxygen atom;

$R^{21}$ and $R^{22}$ are independently of each other and independently of each occurence selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and $SO_2$, as ring members, where the heterocyclic ring may be substituted by one or more radicals selected from the group consisting of halogen, $C_1$-$C_6$-alkyl, $C_1$-$C_6$-haloalkyl, $C_1$-$C_6$-alkoxy and $C_1$-$C_6$-haloalkoxy;

each m is independently 1 or 2;
each n is independently 0, 1 or 2;
p is 0, 1, 2, 3 or 4; and
q is 0, 1 2, 3, 4 or 5;
or a stereoisomer or an agriculturally or veterinarily acceptable salt thereof.

2. The compound according to claim 1, wherein $A^4$ is CH.

3. The compound according to claim 1, wherein X is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$alkyl, $C_3$-$C_6$-cycloalkyl and $C_3$-$C_6$-halocycloalkyl.

4. The compound according to claim 3, wherein X is selected from the group consisting of $C_1$-$C_4$-alkyl, $C_1$-$C_4$-haloalkyl, $C_3$-$C_6$-cycloalkyl and $C_3$-$C_6$-halocycloalkyl.

5. The compound according to claim 1, wherein $R^1$ is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or $R^1$ and $R^2$ together are —$CH_2CH_2$—, —$CH_2CH_2CH_2$— or —$CR^{61}$=$CR^{61}$—.

6. The compound according to claim 5, wherein $R^1$ is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$.

7. The compound according to claim 6, wherein $R^1$ is selected from the group consisting of hydrogen; cyano; $C_1$-$C_6$-alkyl; $C_1$-$C_4$-haloalkyl; $C_1$-$C_4$-alkoxy; $C_1$-$C_4$-haloalkoxy; and —C(=O)$R^6$.

8. The compound of claim 1, wherein $R^2$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —N($R^8$)$R^9$; —N($R^8$)C(=O)$R^6$; —Si($R^{14}$)$_2R^{13}$; —O$R^7$; —S$R^7$; —S(O)$_mR^7$; —S(O)$_nN(R^8)R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$ phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or $R^1$ and $R^2$ together are —$CH_2CH_2$—, —$CH_2CH_2CH_2$— or —$CR^{61}$=$CR^{61}$—;

or $R^2$ and $R^3$ together form a group =$CR^{11}R^{12}$; =$S(O)_mR^7$; =$S(O)_mN(R^8)R^9$; =$NR^8$; or =$NOR^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or $NR^{18}$ and/or 1 or 2 of the $CH_2$ groups of the alkylene chain may be replaced by a group C=O, C=S and/or C=$NR^{18}$; and/or the alkylene chain may be substituted by one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^{10}$.

9. The compound of claim 1, wherein R$^2$ is selected from the group consisting of hydrogen; C$_1$-C$_{10}$-alkyl which may be partially or fully halogenated and/or may be substituted by one or more radicals R$^6$; C$_3$-C$_8$-cycloalkyl which may be partially or fully halogenated and/or may be substituted by one or more radicals R$^6$; C$_2$-C$_{10}$-alkenyl which may be partially or fully halogenated and/or may be substituted by one or more radicals R$^6$; C$_2$-C$_{10}$-alkynyl which may be partially or fully halogenated and/or may be substituted by one or more radicals R$^6$; —C(=O)R$^6$; —C(=O)OR$^7$; —C(=O)N(R$^8$)R$^9$; —C(=S)R$^6$; —C(=S)OR$^7$; —C(=S)N(R$^8$)R$^9$; —C(=NR$^8$)R$^6$, phenyl which may be substituted by 1, 2, 3, 4 or 5 radicals R$^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^{10}$.

10. The compound of claim 1, wherein R$^2$ is selected from the group consisting of hydrogen; C$_1$-C$_4$-alkyl; C$_1$-C$_4$-haloalkyl; a methyl group substituted by a radical R$^{6a}$ selected from the group consisting of CN, phenyl which may carry 1, 2 or 3 substituents R$^{10a}$, —C(=O)R$^{6b}$; —C(=O)N(R$^{8a}$)R$^{9a}$ and —C(=O)OR$^{7a}$; —C(=O)R$^{6c}$; —C(=O)N(R$^{8a}$)R$^{9a}$; and
—C(=NR$^{8a}$)R$^{6d}$,
where
R$^{6b}$ and R$^{6c}$ are independently selected from the group consisting of C$_1$-C$_4$-alkyl, C$_1$-C$_4$-haloalkyl, phenyl, benzyl and a 5- or 6-membered saturated, partially unsaturated or aromatic heterocyclic ring containing 1, 2 or 3 heteroatoms or heteroatom groups selected from the group consisting of N, O, S, NO, SO and SO$_2$, as ring members, where the phenyl or heterocyclyl rings in the three last-mentioned radicals may carry 1, 2 or 3 substituents selected from the group consisting of halogen, CN, C$_1$-C$_4$-alkyl, C$_1$-C$_4$-haloalkyl, C$_1$-C$_4$-alkoxy and C$_1$-C$_4$-haloalkoxy;
R$^{6d}$ is selected from N(R$^{8a}$)R$^{9a}$;
R$^{7a}$ is selected from the group consisting of hydrogen, C$_1$-C$_4$-alkyl, C$_1$-C$_4$-haloalkyl, phenyl, benzyl and a 5- or 6-membered saturated, partially unsaturated or aromatic heterocyclic ring containing 1, 2 or 3 heteroatoms or heteroatom groups selected from the group consisting of N, O, S, NO, SO and SO$_2$, as ring members, where the phenyl or heterocyclyl rings in the three last-mentioned radicals may carry 1, 2 or 3 substituents selected from the group consisting of halogen, CN, C$_1$-C$_4$-alkyl, C$_1$-C$_4$-haloalkyl, C$_1$-C$_4$-alkoxy and C$_1$-C$_4$-haloalkoxy;
each R$^{8a}$ is independently selected from the group consisting of hydrogen, cyano, C$_1$-C$_6$-alkyl which may be partially or fully halogenated and/or may be substituted by one or more radicals R$^{19}$, C$_2$-C$_4$-alkenyl which may be partially or fully halogenated and/or may be substituted by one or more radicals R$^{19}$, C$_3$-C$_6$-cycloalkyl, C$_3$-C$_6$-halocycloalkyl, C$_3$-C$_6$-cycloalkyl-C$_1$-C$_4$-alkyl, C$_3$-C$_6$-halocycloalkyl-C$_1$-C$_4$-alkyl —S(O)$_m$R$^{20}$, —S(O)$_n$N(R$^{21}$)R$^{22}$, phenyl, benzyl and a 5- or 6-membered saturated, partially unsaturated or aromatic heterocyclic ring containing 1, 2 or 3 heteroatoms or heteroatom groups selected from the group consisting of N, O, S, NO, SO and SO$_2$, as ring members, where the phenyl or heterocyclyl rings in the three last-mentioned radicals may carry 1, 2 or 3 substituents selected from the group consisting of halogen, CN, C$_1$-C$_4$-alkyl, C$_1$-C$_4$-haloalkyl, C$_1$-C$_4$-alkoxy and C$_1$-C$_4$-haloalkoxy;
each R$^{9a}$ is independently selected from the group consisting of hydrogen, cyano, C$_1$-C$_6$-alkyl which may be partially or fully halogenated and/or may be substituted by one or more radicals R$^{19}$, C$_2$-C$_4$-alkenyl which may be partially or fully halogenated and/or may be substituted by one or more radicals R$^{19}$, C$_3$-C$_6$-cycloalkyl, C$_3$-C$_6$-halocycloalkyl, C$_3$-C$_6$-cycloalkyl-C$_1$-C$_4$-alkyl, C$_3$-C$_6$-halocycloalkyl-C$_1$-C$_4$-alkyl, —S(O)$_m$R$^{20}$, —S(O)$_n$N(R$^{21}$)R$^{22}$, phenyl, benzyl and a 5- or 6-membered saturated, partially unsaturated or aromatic heterocyclic ring containing 1, 2 or 3 heteroatoms or heteroatom groups selected from the group consisting of N, O, S, NO, SO and SO$_2$, as ring members, where the phenyl or heterocyclyl rings in the three last-mentioned radicals may carry 1, 2 or 3 substituents selected from the group consisting of halogen, CN, C$_1$-C$_4$-alkyl, C$_1$-C$_4$-haloalkyl, C$_1$-C$_4$-alkoxy and C$_1$-C$_4$-haloalkoxy; and
R$^{10a}$ is selected from the group consisting of halogen, CN, C$_1$-C$_4$-alkyl, C$_1$-C$_4$-haloalkyl, C$_1$-C$_4$-alkoxy and C$_1$-C$_4$-haloalkoxy;
where R$^{19}$ is as defined in claim 1; or
R$^{8a}$ and R$^{9a}$ together form a group =CR$^{11}$R$^{12}$; or
R$^{8a}$ and R$^{9a}$, together with the nitrogen atom to which they are bound, form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and SO$_2$, as ring members, where the heterocyclic ring may be substituted by one or more radicals R$_{10}$.

11. The compound of claim 1, wherein the combination of Y—R$^2$ is NR$^3$—C(=O)—N(R$^8$)R$^9$, where
R$^3$ is selected from the group consisting of hydrogen, C$_1$-C$_4$-alkyl, C$_1$-C$_4$-haloalkyl, C$_1$-C$_4$-alkylcarbonyl, C$_1$-C$_4$-haloalkylcarbonyl, C$_1$-C$_4$-alkoxycarbonyl and C$_1$-C$_4$-haloalkoxycarbonyl;
R$^9$ is selected from the group consisting of hydrogen, cyano, C$_1$-C$_4$-alkyl, C$_1$-C$_4$-haloalkyl, cyclopropyl, C$_1$-C$_4$-alkylcarbonyl, C$_1$-C$_4$-haloalkylcarbonyl, C$_1$-C$_4$-alkoxycarbonyl and C$_1$-C$_4$-haloalkoxycarbonyl; and
R$^8$ is selected from the group consisting of CN, C$_1$-C$_6$-alkyl; C$_1$-C$_6$-haloalkyl; C$_1$-C$_4$-alkyl which carries one radical R$^{19}$; C$_2$-C$_6$-alkenyl; C$_2$-C$_6$-haloalkenyl; C$_2$-C$_4$-alkenyl which is substituted by one radical R$^{19}$; C$_3$-C$_6$-cycloalkyl; C$_3$-C$_6$-halocycloalkyl; C$_3$-C$_6$-cycloalkyl-C$_1$-C$_4$-alkyl; C$_3$-C$_6$-halocycloalkyl-C$_1$-C$_4$-alkyl; —S(O)$_m$R$^{20}$; —S(O)$_n$N(R$^{21}$)R$^{22}$; phenyl; benzyl and a 5- or 6-membered saturated, partially unsaturated or aromatic heterocyclic ring containing 1, 2 or 3 heteroatoms or heteroatom groups selected from the group consisting of N, O, S, NO, SO and SO$_2$, as ring members, where the phenyl or heterocyclyl rings in the three last-mentioned radicals may carry 1, 2 or 3 substituents selected from the group consisting of halogen, CN, C$_1$-C$_4$-alkyl, C$_1$-C$_4$-haloalkyl, C$_1$-C$_4$-alkoxy and C$_1$-C$_4$-haloalkoxy.

12. The compound according to claim 1, wherein R$^3$ is selected from the group consisting of hydrogen; cyano; C$_1$-C$_{10}$-alkyl which may be partially or fully halogenated and/or may be substituted by one or more radicals R$^6$; C$_3$-C$_8$-cycloalkyl which may be partially or fully halogenated and/or may be substituted by one or more radicals R$^6$; C$_2$-C$_{10}$-alkenyl which may be partially or fully halogenated and/or may be substituted by one or more radicals R$^6$; C$_2$-C$_{10}$-alkynyl which may be partially or fully halogenated and/or may be substituted by one or more radicals $R^6$; —N($R^8$)$R^9$; —Si($R^{14}$)$_2R^{13}$; —O$R^7$; —S$R^7$; —S(O)$_mR^7$; —S(O)$_nN(R^8)R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;

or $R^2$ and $R^3$ together form a group =C$R^{11}R^{12}$; =S(O)$_mR^7$; =S(O)$_mN(R^8)R^9$; =N$R^8$; or =NO$R^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or N$R^{18}$ and/or 1 or 2 of the CH$_2$ groups of the alkylene chain may be replaced by a group C=O, C=S and/or C=N$R^{18}$; and/or the alkylene chain may be substituted by one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$.

13. The compound according claim 1, wherein $R^3$ is selected from the group consisting of hydrogen; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$;

$C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^h$); and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$.

14. The compound of claim 1, wherein $R^3$ is selected from the group consisting of hydrogen; $C_1$-$C_6$-alkyl and $C_1$-$C_4$-haloalkyl.

15. The compound according to claim 1, wherein each $R^4$ is independently selected from the group consisting of halogen; cyano; nitro; —SCN; SF$_5$; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_6$-alkenyl which may be partially or fully halogenated and/or may be substituted by one or more radicals $R^6$; $C_2$-$C_6$-alkynyl which may be partially or fully halogenated and/or may be substituted by one or more radicals $R^6$; —Si($R^{14}$)$_2R^{13}$; —O$R^7$; —OS(O)$_nR^7$; —S$R^7$; —S(O)$_mR^7$; —S(O)$_nN(R^8)R^9$; —N($R^8$)$R^9$; —N($R^8$)C(=O)$R^6$; C(=O)$R^6$; —C(=O)O$R^7$; —C(=N$R^8$)H; —C(=N$R^8$)$R^6$; —C(=O)N($R^8$)$R^9$; C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;

or two radicals $R^4$ bound on adjacent carbon atoms may be together a group selected from the group consisting of —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$N$R^8$—, —CH$_2$CH=N—, —CH=CH—N$R^8$—, —OCH=N—, and —SCH=N—, thus forming, together with the carbon atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more CH$_2$ groups of the above groups may be replaced by a C=O group.

16. The compound according to claim 1, wherein each $R^4$ is independently selected from the group consisting of halogen; cyano; nitro; —SCN; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; —O$R^7$; —OS(O)$_nR^7$; —S$R^7$; —S(O)$_mR^7$; —S(O)$_nN(R^8)R^9$; —N($R^8$)$R^9$; C(=O)$R^6$; —C(=O)O$R^7$; —C(=N$R^8$)$R^6$; —C(=O)N($R^8$)$R^9$; and —C(=S)N($R^8$)$R^9$.

17. The compound according claim 1, wherein $R^4$ is selected from the group consisting of halogen; cyano, $C_1$-$C_4$-alkyl and $C_1$-$C_4$-haloalkyl.

18. The compound of claim 1, wherein each $R^5$ is independently selected from the group consisting of halogen, cyano, nitro, —SCN, SF$_5$, $C_1$-$C_6$-alkyl, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $C_2$-$C_6$-alkenyl which may be partially or fully halogenated and/or may be substituted by one or more radicals $R^6$, $C_2$-$C_6$-alkynyl which may be partially or fully halogenated and/or may be substituted by one or more radicals $R^6$, Si($R^{14}$)$_2R^{13}$, O$R^7$, OS(O)$_nR^7$, S(O)$_mR^7$, N$R^8R^9$, N($R^8$)C(=O)$R^6$, C(=O)$R^6$, C(=O)O$R^7$, C(=N$R^8$)$R^6$, C(=S)N$R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$.

19. The compound according claim 1, wherein $R^5$ is selected from the group consisting of halogen and $C_1$-$C_4$-haloalkyl.

20. The compound according to claim 1, having the formula I-1

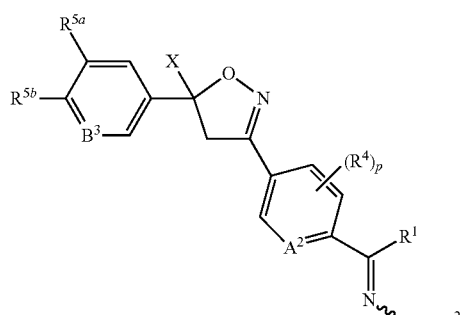

(I-1)

wherein $A^2$ is CH;

$B^3$ is $CR^{5c}$;

$R^{5a}$, $R^{5c}$ are, independently of each other, selected from the group consisting of hydrogen, halogen, cyano, nitro, SCN, $SF_5$, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $OR^7$, $SR^7$, $S(O)_mR^7$, $NR^8R^9$, $C(=O)R^6$, —$C(=O)OR^7$, $C(=NR^8)R^6$, $C(=S)NR^6$; and $R^{5b}$ is selected from the group consisting of hydrogen, halogen, cyano, nitro, —SCN, $SF_5$, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $C_2$-$C_6$-alkenyl which may be partially or fully halogenated and/or may be substituted by one or more radicals $R^6$, $C_2$-$C_6$-alkynyl which may be partially or fully halogenated and/or may be substituted by one or more radicals $R^6$, $Si(R^{14})_2R^{13}$, $OR^7$, $SR^7$, $OS(O)_nR^7$, $S(O)_mR^7$, $NR^8R^9$, $N(R^8)C(=O)R^6$, $C(=O)R^6$, $C(=O)OR^7$, $C(=NR^8)R^6$, $C(=S)NR^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$.

21. The compound of claim 20, wherein $R^{5a}$, $R^{5b}$ and $R^{5c}$ are, independently of each other, selected from the group consisting of hydrogen, halogen, cyano, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy.

22. The compound of claim 1, having the formula I-1.1

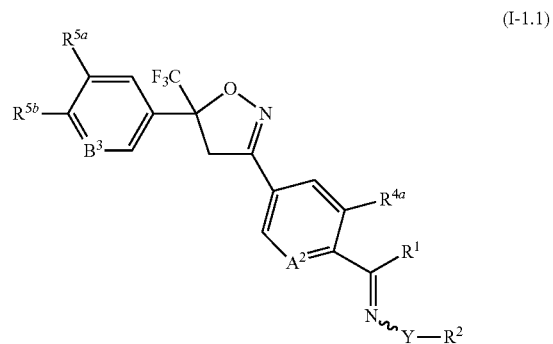

(I-1.1)

wherein $A^2$ is CH;

$B^3$ is $CR^{5c}$; and $R^{4a}$ is selected from the group consisting of hydrogen, halogen, cyano, nitro, —SCN, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, —$OR^7$, —$OS(O)_nR^7$, —$SR^7$, —$S(O)_mR^7$, —$S(O)_nN(R^8)R^9$, —$N(R^8)R^9$, —$N(R^8)C(=O)R^6$, $C(=O)R^6$, —$C(=O)OR^7$, —$C(=NR^8)R^6$, —$C(=O)N(R^8)R^9$, —$C(=S)N(R^8)R^9$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

$R^5$, $R^{5b}$ and $R^{5c}$ are, independently of each other, selected from the group consisting of hydiogen, halogen, cyano, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy.

23. The compound of claim 22, wherein $R^{4a}$ is selected from the group consisting of hydrogen, halogen, cyano, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy.

24. The compound of claim 1, wherein Y is O, $NR^3$ or a chemical bond.

25. The compound of claim 1 having the formula I-1.1.1

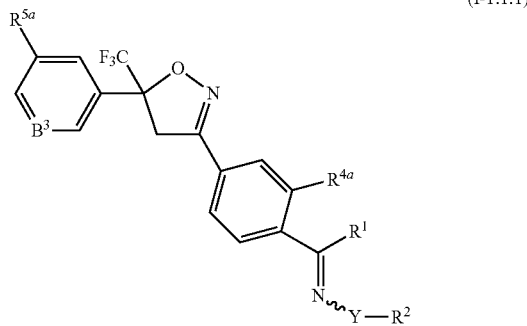

(I-1.1.1)

wherein $R^{4a}$ is selected from the group consisting of hydrogen, halogen, cyano, nitro, —SCN, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, —$OR^7$, —$OS(O)_nR^7$, —$SR^7$, —$S(O)_mR^7$, —$S(O)_nN(R^8)R^9$, —$N(R^8)R^9$, —$N(R^8)C(=O)R^6$, $C(=O)R^6$, —$C(=O)OR^7$, —$C(=NR^8)R^6$, —$C(=O)N(R^8)R^9$, —$C(=S)N(R^8)R^9$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

$R^{5a}$, $R^{5c}$ are, independently of each other, selected from the group consisting of hydrogen, halogen, cyano, nitro, SCN, $SF_5$, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $OR^7$, $SR^7$, $S(O)_mR^7$, $NR^8R^9$, $C(=O)R^6$, —$C(=O)OR^7$, $C(=NR^8)R^6$, $C(=S)NR^6$; and $B^3$ is $CR^{5c}$.

26. An agricultural composition comprising at least one compound of claim 1 and at least one inert liquid and/or solid agriculturally acceptable carrier.

27. A veterinary composition comprising at least one compound of claim 1 and at least one inert liquid and/or solid veterinarily acceptable carrier.

28. A method for controlling invertebrate pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from invertebrate pest attack or infestation with a pesticidally effective amount of at least one compound of claim 1.

29. A method for protecting plants from attack or infestation by invertebrate pests, which method comprises treating the plants with a pesticidally effective amount of at least one compound of claim 1.

30. A method for protecting plant propagation material and/or the plants which grow therefrom from attack or infestation by invertebrate pests, which method comprises treating the plant propagation material with a pesticidally effective amount of at least one compound of claim 1.

31. Plant propagation material treated with at least one compound of claim 1.

32. A method for treating or protecting an animal from infestation or infection by invertebrate pests which comprises bringing the animal in contact with a pesticidally effective amount of at least one compound of claim 1.

* * * * *

UNITED STATES PATENT AND TRADEMARK OFFICE
CERTIFICATE OF CORRECTION

PATENT NO. : 8,722,673 B2  
APPLICATION NO. : 13/140989  
DATED : May 13, 2014  
INVENTOR(S) : Karsten Koerber et al.

Page 1 of 1

It is certified that error appears in the above-identified patent and that said Letters Patent is hereby corrected as shown below:

In the Claims

In claim 1,
- col. 162, line 20, delete "le" and insert therefore --$R^{19}$--;
- col. 163, line 63, delete "$C_1$-$C_o$-alkyl" and insert therefore --$C_1$-$C_6$-alkyl--;
- col. 164, line 17, delete "$C_1$-alkoxy" and insert therefore --$C_1$-$C_6$-alkoxy--; and lines 21-22, delete "$C_2$-$C_o$-alkynyl" and insert therefore --$C_2$-$C_6$-alkynyl--.

In claim 11,
- col. 168, line 37, delete "$C_1$-$C_4$-alkoxyearbonyl" and insert therefore --$C_1$-$C_4$-alkoxycarbonyl--.

In claim 13,
- col. 169, line 50, delete "$R^h$" and insert therefore --$R^{10}$--.

In claim 22,
- col. 172, line 35, delete "$R^5$" and insert therefore --$R^{5a}$--; and line 36, delete "hydiogen" and insert therefore --hydrogen--.

Signed and Sealed this  
Seventh Day of July, 2015

Michelle K. Lee  
*Director of the United States Patent and Trademark Office*